US011738095B2

(12) United States Patent
Chung et al.

(10) Patent No.: US 11,738,095 B2
(45) Date of Patent: Aug. 29, 2023

(54) CYANINE-CONTAINING COMPOUNDS FOR CANCER IMAGING AND TREATMENT

(71) Applicants: Emory University, Atlanta, GA (US); Georgia State University Research Foundation, Inc., Atlanta, GA (US)

(72) Inventors: Leland W. K. Chung, Beverly Hills, CA (US); Lucjan Strekowski, Stone Mountain, GA (US); Chunmeng Shi, Chongqing (CN); Maged Henary, Lawrenceville, GA (US); Gabor Patonay, Conyers, GA (US); James J. Krutak, Colorado Springs, CO (US); Xiaojian Yang, Shannxi (CN); Guodong Zhu, Atlanta, GA (US); Ruoxiang Wang, Los Angeles, CA (US); Haiyen E. Zhau, Beverly Hills, CA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/422,948

(22) Filed: Feb. 2, 2017

(65) Prior Publication Data

US 2017/0354747 A1     Dec. 14, 2017

Related U.S. Application Data

(63) Continuation of application No. 14/815,591, filed on Jul. 31, 2015, now abandoned, which is a continuation of application No. 14/656,173, filed on Mar. 12, 2015, now abandoned, which is a continuation of application No. 12/668,460, filed as application No. PCT/US2008/069631 on Jul. 10, 2008, now abandoned.

(60) Provisional application No. 60/959,413, filed on Jul. 13, 2007.

(51) Int. Cl.
| | | |
|---|---|---|
| *A61K 49/00* | (2006.01) | |
| *A61K 31/404* | (2006.01) | |
| *G01N 33/50* | (2006.01) | |
| *C07D 209/60* | (2006.01) | |
| *C07D 209/92* | (2006.01) | |
| *C07D 209/10* | (2006.01) | |

(52) U.S. Cl.
CPC ............ *A61K 49/00* (2013.01); *A61K 31/404* (2013.01); *C07D 209/10* (2013.01); *C07D 209/60* (2013.01); *C07D 209/92* (2013.01); *G01N 33/5008* (2013.01)

(58) Field of Classification Search
CPC .. A61K 49/00; A61K 31/404; A61K 49/0032; G01N 33/5008; C07D 209/60; C07D 209/92; C07D 209/10
See application file for complete search history.

(56) References Cited

U.S. PATENT DOCUMENTS

| | | | |
|---|---|---|---|
| 5,453,505 A | 9/1995 | Lee et al. | |
| 5,804,389 A | 9/1998 | Tada | |
| 5,986,086 A | 11/1999 | Brush et al. | |
| 6,051,532 A | 4/2000 | Burberry et al. | |
| 6,180,085 B1 * | 1/2001 | Achilefu ............ | A61K 41/0033 424/1.11 |
| 6,191,290 B1 | 2/2001 | Safavy | |
| 6,214,812 B1 | 4/2001 | Karpeisky et al. | |
| 6,593,148 B1 | 7/2003 | Narayanan | |
| 6,747,151 B2 | 6/2004 | Rajagopalan et al. | |
| 6,747,159 B2 | 6/2004 | Caputo et al. | |
| 6,944,493 B2 | 9/2005 | Alam et al. | |
| 6,989,140 B2 | 1/2006 | Tidmarsh et al. | |
| 6,989,149 B2 | 1/2006 | Glenn, Jr. et al. | |
| 7,011,817 B2 | 3/2006 | Achilefu et al. | |
| 7,056,952 B1 | 6/2006 | Joannou | |
| 7,060,654 B2 | 6/2006 | Kasperchik et al. | |
| 7,198,778 B2 | 4/2007 | Achilefu et al. | |
| 7,244,232 B2 | 7/2007 | Connelly et al. | |
| 7,344,699 B2 | 3/2008 | Lappin et al. | |
| 7,799,955 B2 | 9/2010 | Joannou | |
| 8,255,432 B2 | 8/2012 | Ackerman et al. | |
| 9,610,370 B2 | 4/2017 | Chung et al. | |
| 9,675,620 B2 | 6/2017 | Shih et al. | |
| 9,771,625 B2 | 9/2017 | Shih et al. | |
| 10,125,099 B2 | 11/2018 | Shih et al. | |

(Continued)

FOREIGN PATENT DOCUMENTS

| | | | | |
|---|---|---|---|---|
| CN | 102099059 A | | 6/2011 | |
| CN | 101518528 B | * | 2/2014 | ........... A61K 31/404 |

(Continued)

OTHER PUBLICATIONS

Frangioni, Current Opinion in Chemical Biology, 2003, 7, p. 626-634. (Year: 2003).*
Chen et al., Journal of Photochemistry and Photobiology A: Chemistry, 2006, 181, p. 79-85 (Year: 2006).*
Adler, et al., "Pharmacological treatment of frontotemporal dementia: treatment response to the MAO-A inhibitor moclobemide", International Journal of Geriatric Psychiatry, vol. 18, No. 7, Jul. 1, 2003, p. 653-655.
Jhaveri, et al., "Noscapine inhibits tumor growth in TMZ-resistant gliomas." Cancer Letters, New York, NY, US, vol. 312, No. 2, Aug. 15, 2011, p. 245-252.

(Continued)

*Primary Examiner* — Michael G. Hartley
*Assistant Examiner* — Leah H Schlientz
(74) *Attorney, Agent, or Firm* — Ellenoff Grossman & Schole LLP; James M. Smedley, Esq.

(57) ABSTRACT

This invention relates generally to cyanine-containing compounds; pharmaceutical compositions comprising cyanine-containing compounds; and methods of using cyanine-containing compounds for cancer cell imaging, cancer cell growth inhibition, and detecting cancer cells, for example. Compounds of the invention are preferentially taken up by cancer cells as compared to normal cells. This allows many uses in the cancer treatment, diagnosis, tracking and imaging fields.

22 Claims, 21 Drawing Sheets

(56) References Cited

U.S. PATENT DOCUMENTS

| | | | |
|---|---|---|---|
| 10,307,489 | B2 | 6/2019 | Chung |
| 10,561,663 | B2 | 2/2020 | Shih et al. |
| 2004/0028611 | A1 | 2/2004 | Frangioni |
| 2004/0052727 | A1 | 3/2004 | Dalton et al. |
| 2005/0074796 | A1 | 4/2005 | Yue et al. |
| 2005/0085630 | A1 | 4/2005 | Olejnik et al. |
| 2005/0136007 | A1 | 6/2005 | Kagawa et al. |
| 2005/0222248 | A1 | 10/2005 | Joannou |
| 2005/0226815 | A1* | 10/2005 | Kawakami ......... A61K 49/0032 424/9.6 |
| 2005/0255042 | A1 | 11/2005 | Lam et al. |
| 2005/0281741 | A1 | 12/2005 | Achilefu et al. |
| 2006/0165701 | A1 | 7/2006 | De Haen |
| 2006/0292078 | A1 | 12/2006 | Klaveness et al. |
| 2007/0098638 | A1 | 5/2007 | Achilefu et al. |
| 2007/0140962 | A1 | 6/2007 | Achilefu et al. |
| 2007/0297988 | A1* | 12/2007 | Wu ................... A61K 49/0032 424/9.6 |
| 2008/0125481 | A1 | 5/2008 | Joannou |
| 2008/0139665 | A1 | 6/2008 | Schuele et al. |
| 2008/0221343 | A1 | 9/2008 | Schwartz et al. |
| 2009/0209655 | A1 | 8/2009 | Joannou |
| 2010/0040547 | A1 | 2/2010 | Frangioni |
| 2010/0048921 | A1 | 2/2010 | Gorne et al. |
| 2010/0100870 | A1 | 4/2010 | Vandanapu |
| 2010/0137425 | A1 | 6/2010 | Bergan et al. |
| 2010/0143295 | A1 | 6/2010 | Gant et al. |
| 2010/0166659 | A1 | 7/2010 | Licha et al. |
| 2010/0273891 | A1 | 10/2010 | Joannou |
| 2010/0290997 | A1 | 11/2010 | Li et al. |
| 2011/0085974 | A1 | 4/2011 | Chung et al. |
| 2011/0262354 | A1 | 10/2011 | Chung et al. |
| 2013/0101513 | A1 | 4/2013 | Yang et al. |
| 2014/0018563 | A1 | 1/2014 | Hironaka et al. |
| 2015/0367004 | A1 | 12/2015 | Pak et al. |

FOREIGN PATENT DOCUMENTS

| | | |
|---|---|---|
| CN | 103826625 A | 5/2014 |
| CN | 104312194 A | 1/2015 |
| CN | 105288645 A | 2/2016 |
| CN | 106132437 A | 11/2016 |
| DE | 102007002386 A1 | 7/2008 |
| EP | 1679082 A1 | 7/2006 |
| EP | 2303337 A1 | 4/2011 |
| WO | 2000066576 A1 | 11/2000 |
| WO | 2002038190 A3 | 5/2002 |
| WO | 2003032901 A3 | 4/2003 |
| WO | 2003055935 A1 | 7/2003 |
| WO | 2007022494 A2 | 2/2007 |
| WO | 2009012109 A2 | 1/2009 |
| WO | 2009152440 A1 | 12/2009 |
| WO | 2010042933 A2 | 4/2010 |
| WO | 2011116142 A1 | 9/2011 |
| WO | 2012018761 A2 | 2/2012 |
| WO | 2013016580 A2 | 1/2013 |
| WO | 2013033688 A1 | 3/2013 |
| WO | 2013052776 A1 | 4/2013 |
| WO | 2014018563 A2 | 1/2014 |
| WO | 2017079632 A1 | 5/2017 |
| WO | 2020055455 A1 | 3/2020 |

OTHER PUBLICATIONS

Virrey, et al., "Glioma-associated endothelial cells are chemoresistant to temozolomide", Journal of Neuro-Oncology, Kluwer Academic Publishers, BO, vol. 95, No. 1, Apr. 18, 2009, pp. 13-22.
Gabilondo, et al., "Monoamine oxidase B activity is increased in human gliomas", Neurochemisty International, Pergamon Press, Oxford, GB, vol. 52, No. 1-2, Dec. 12, 2007, p. 230-234.
Annex to Form PCT/ISA/206, NPL in U.S. Appl. No. 15/293,055, Forms IB/373 IPER, ISA/237 WO, ISA/210 ISR. Communication Relating to the Results of the Partial International Search issued in related International Application No. PCT/US2015/014695.
Office Action received for European Patent Application No. 12748805.4, dated Feb. 7, 2017, 5 pages.
International Search Report and Written Opinion received for PCT Patent Application No. PCT/US15/14695, dated Jul. 6, 2015, 18 pages.
Nardil label.
Chinese Office Action dated Jan. 2, 2019, regarding CN 201580017548.
Shi et al., "Practical neurology", Shanghai Science and Technology Press; Jan. 1978, NPL in U.S. Appl. No. 16/109,201.
Kashyap, et al., "The lysine specific demethylase-1 (LSD1/KDM1A) regulates VEGF-A expression in prostate cancer", Molecular oncology 7.3 (2013): 555-566.
Paller, et al., "Management of biochemically recurrent prostate cancer after local therapy: evolving standards of care and new directions", Clinical advances in hematology & oncology: H&O 11.1 (2013): 14-23.
D'Amico, et al., "Cancer-specific mortality after surgery or radiation for patients with clinically localized prostate cancer managed during the prostate-specific antigen era", Journal of clinical oncology 21.11 (2003): 2163.2172.
He, et al., "In vivo near-infrared fluorescence imaging of cancer with nanoparticle-based probes", Wiley Interdisciplinary Reviews: Nanomedicine and Nanobiotechnology 2.4 (2010): 349-366.
Kim, et al., "Multifunctional nanostructured materials for multimodal imaging, and simultaneous imaging and therapy", Chemical Society Reviews 38.2 (2009): 372-390.
Ogawa et al., "In vivo Molecular Imaging of Cancer with a Quenching Near Infrared Fluorescent Probe Using Conjugates of Monoclonal Antibodies and Indocyanine Green," Cancer Res., Feb. 15, 2009, available online: Jan. 27, 2009, pp. 1265-1272, vol. 69, No. 4.
McClain et al., "Microfluidic devices for the high-throughput chemical analysis of cells," Anal. Chem., Nov. 1, 2003, pp. 5646-5655, vol. 75, No. 21.
Yusuf et al., "Homing of hematopoietic cells to the bone marrow," (online), J Vis Exp, Mar. 18, 2009, pp. 1-2, vol. 25, (retrieved from the internet on Apr. 27, 2011), available on the internet <URL: http://www.jove.com/details.pho?d=1104>.
Yang et al., "Near IR heptamethine cyanine dye-mediated cancer imaging," Clin Can Res, available online: Apr. 21, 2010, pp. 2833-2844, vol. 16 No. 10.
Zhang et al., "Sentinel lymph node mapping by a near-infrared fluorescent heptamethine dye," Biomaterials ePub, Dec. 5, 2009, pp. 1911-1917, vol. 31 No. 7.
Chen et al., "A Novel Approach to a Bifunctional Photosensitizer for Tumor Imaging and Phototherapy," Bioconjugage Chem., 2005, pp. 1264-1274, vol. 16.
Chinese Patent Application No. 200980126216.X, Office Action, dated Apr. 24, 2012.
European Patent Application No. 09763728.4, Extended European Search Report, dated Aug. 1, 2014.
Kawakami et al., "Structure-Activity of Novel Rhodacyanine Dyes as Antitumor Agents," J. Med. Chem., 1998, pp. 130-142, vol. 41.
Kim et al., "Membrane Permeable Esterase-Activated Fluorescent Imaging Probe," Bloorg. Med. Chem. Lett., 2007, pp. 5054-5057, vol. 17.
Mojoros et al., "PAMAM Dendrimer-Based Multifunctional Conjugate for Cancer Therapy: Synthesis, Characterization, and Functionality," Biomacromolecules, 2006, pp. 572-579, vol. 7.
Narayanan et al., "A New Method for the Synthesis of Heptamethine Cyanine Dyes: Synthesis of New Near-Infrared Fluorescent Labels," J. Org. Chem., 1995, pp. 2391-2395, vol. 60.
PCT Patent Application No. PCT/US2009/047216, International Preliminary Report on Patentability, dated Dec. 14, 2010.
PCT Patent Application No. PCT/US2009/047216, Written Opinion, dated Sep. 23, 2009.
PCT Patent Application No. PCT/US2009/047216, International Search Report, dated Sep. 23, 2009.
PCT Patent Application No. PCT/US2008/069631, International Preliminary Report on Patentability, dated Jan. 19, 2010.
PCT Patent Application No. PCT/US2008/069631, Written Opinion, dated Oct. 3, 2008.

(56) References Cited

OTHER PUBLICATIONS

PCT Patent Application No. PCT/US2008/069631, International Search Report, dated Oct. 3, 2008.
PCT Patent Application No. PCT/US2011/028738, International Search Report, dated Jun. 16, 2011.
Sun et al., "Anticarcinoma Activity of a Novel Drug, 3-ethyl-3'-methyl-thiatelluracarbocyanine iodide (Te), a Tellurium-Containing Cyanine Targeted at Mitochondria," Clin. Cancer Res., 1996, pp. 1335-1340, vol. 2(8).
Xiao et al., Heptamethine Cyanine Based (64) Cu-PET probe PC-1001 for Cancer Imaging: Synthesis and in vivo Evaluation, Nucl. Med. Biol., 2013, pp. 351-360, vol. 40(3).
Zhang et al., "Mechanistic Study of IR-780 dye as a potential Tumor Targeting and Drug Delivery Agent," Biomaterials, 2014, pp. 771-778, vol. 35(2).
Delaey et al., "A Comparative Study of the Photosensitizing Characteristics of Some Cyanine Dyes," J. Photochem. Photobiol. B., 2000, pp. 27-36, vol. 55.
Yang et al., Folate-based near-infrared fluorescent theranostic gemcitabine delivery, J. Am. Chem. Soc., Aug. 7, 2013, pp. 11657-11662, vol. 135, No. 31.
International Search Report published with WO2016106324 (PCT/US2015/067393).
Liu et al., "Synthesis of 2'-paclitaxel methyl 2-glucopyranosyl succinate for specific targeted delivery to cancer cells," Bioorg. Med. Chem. Lett., 2007, pp. 617-620, vol. 17.
Wu et al., "Near-infrared fluorescence and nuclear imaging and targeting of prostate cancer," Trans. Androl. Urol., 2013, pp. 254-264, vol. 2.
Semenenko et al., "Evaluation of Near Infrared Dyes as Markrs of P-Glycoprotein Activity in Tumors," Frontiers in Pharmacology, Nov. 15, 2016, pp. 1-9, vol. 7 Article 426.
Safavy et al., "Paclitaxel Derivatives for Targeted Therapy of Cancer: Toward the Development of Smart Taxanes," J. Med. Chem., 1999, pp. 4919-4924, vol. 42.
Lipowska et al., "New Near-Infrared Cyanine Dyes for Labelling of Proteins," Synthetic Comm., 1993, pp. 3087-3094, vol. 23.
Gao et al., "In vivo cancer targeting and imaging with semiconductor quantum dots," Nature Biotechnology, 2004, pp. 969-976, vol. 22(6).
Samia et al., "Semiconductor Quantum Dots for Photodynamic Therapy," JACS, 2003, pp. 15736-15737, vol. 125 (51).
Kukowska-Latallo et al., "Nanoparticle targeting of anticancer drug improves therapeutic response in animal model of human epithelial cancer," Cancer Res, 2005, pp. 5317-5324, vol. 65(12).
Lee et al., "Synthesis and Spectral Properties of Near-Infrared Aminophenyl-, Hydroxyphenyl-, and Phenyl-Substituted deptamethine Cyanines," Journal of Organic Chemistry, 2008, pp. 723-725, vol. 73.
International preliminary report on patentability dated Jan. 26, 2014 issued in corresponding PCT application PCT/US12/48407.
European Search Report (Communication pursuant to Rule 164(2)(b) and Article 94(3) EPC) dated Jul. 21, 2015 issued in EPC Application No. 12748805.4.
International search report dated Feb. 14, 2013 issued in PCT application No. PCT/US2012/048407.
Peehl et al., "The Significance of Monoamine Oxidase-A-Expression in High Grade Prostate Cancer," Journal of Urology, Nov. 2008, pp. 2206-2211, vol. 180.
Written Opinion dated Jan. 26, 2014 issued in PCT application No. PCT/US2012/048407.
Flamand et al., "864 Monoamine Oxidase A: A New Candidate Therapeutic Target for Advanced Prostate Cancer," European Urology Supplements, Apr. 1, 2010, p. 274, vol. 9, No. 2.
Zhao et al., "Anti-oncogenic and pro-differentiation effects of clorgyline, a monoamine oxidase A inhibitor, on high grade prostate cancer cells," BMC Medical Genomics, 2009, pp. 1-15, vol. 2.
Second Notification of Office Action dated Aug. 5, 2016 issued in Chinese patent application No. 201280046591.5.
Andree and Clarke, "Characteristics and Specificity of Phenelzine and Benserazide as Inhibitors of Benzylamine Oxidase and Monoamine Oxidase," Biochem. Pharmacol., 1982, 31(5): 825-830, Pergamon Press Ltd.
De Girolamo et al., "Protection from MPTP-Induces Neurotoxicity in Differentiating Mouse N2a Neuroblastoma Cells," J. Neurochem. (2001), 76:650-660, International Society for Neurochemistry.
International Preliminary Report on Patentability dated Aug. 9, 2016 issued in International Application No. PCT/US2015/014695.
Baumanis, et al., "The modification of the catalytic activity of mitochrondrial monoaminooxidase and the suppression of the growth of experimental brain tumors", Database Medline (Online): US National Library of Medicine (NLM), Bethesda, MD, US; Jul. 1990.
Singh, et al., "Inhibition of LSD1 sensitizes glioblastoma cells to histone deacetylase inhibitors", Neuro-Oncology, vol. 13, No. 8, Aug. 2011, p. 894-903.
Baumanis, et al., "[comparative study of the effect of inhibitors of monoamine oxidase and florafur on the growth of de-differentiated astrocytoma]." Database Medline (Online); US National Library of Medicine (NLM); Bethesda, MD, US: 1976.
Second Notification of Office Action dated Aug. 5, 2016 issued in Chinese patent application No. 201280046591.5, NPL in U.S. Appl. No. 15/904,103.
Strekowski et al., Synthesis of Water-Soluble Near-Infrared Cyanine Dyes Functionalized with [(Succinimido)oxy] carbonyl Group, vol. 40, No. 5, 2003, pp. 913-916.
Patonay et al., The increasing role of NIR fluorescence spectroscopy in bioanalytical chemistry, vol. 18, No. 3, 2007, pp. 7-9.

* cited by examiner

CYANINE-CONTAINING COMPOUNDS FOR CANCER IMAGING AND TREATMENT

CROSS-REFERENCE TO RELATED APPLICATIONS

This application is a continuation application of U.S. patent application Ser. No. 14/815,591, filed Jul. 31, 2015, which is a continuation application of U.S. patent application Ser. No. 14/656,173, filed Mar. 12, 2015, which is a continuation application of U.S. patent application Ser. No. 12/668,460, filed May 9, 2011, under 35 USC § 371(c), which is a U.S. national stage application of International Application No. PCT/US08/69631, filed Jul. 10, 2008, which claims the benefit of the filing date of U.S. Provisional Application No. 60/959,413, filed Jul. 13, 2007, the disclosures of which are hereby incorporated by reference to the extent not inconsistent with the disclosure herein.

BACKGROUND OF THE INVENTION

Dyes that absorb and emit light in different regions of the electromagnetic spectrum are currently used for various biomedical applications. Optical imaging in the near infrared region ("NIR") (680-1600 nm) has received much attention due to the low intrinsic absorption of biomolecules in that region and the penetration of NIR light several centimeters into tissue, a depth sufficient to image most small animal models (see, for example, Rao, et al., Current Opinion in Biotechnology, 2007, 18:17-25). "Windows" for imaging biomolecules are known where various biological molecules (such as oxyhemoglobin, deoxyhemoglobin, lipids, and water) have limited interference. The NIR wavelengths of between about 680 nm and 900 nm are particularly useful for biomolecule imaging (see Chance, Ann. NY Acad. Sci, 1998, 838:29-45 and Conway, Am. J. Clin. Nutr, 1984, 40:1123-30).

Cyanine dyes emit fluorescence in the NIR region, and several cyanine dye compounds have been investigated as fluorescent contrast agents for imaging tissue. Most cyanine dyes require a ligand or targeting agent (such as a protein, peptide, carbohydrate, or antibody) to selectively attach to tumor cells. Certain cyanine dyes have been reported as having antitumor properties. However, most cyanine dyes are not effective for in vitro treatment or imaging because the dyes are toxic to normal cells as well as tumor cells, or are poorly soluble in pharmaceutically acceptable solvents.

SUMMARY OF THE INVENTION

This invention relates generally to cyanine-containing compounds; pharmaceutical compositions comprising cyanine-containing compounds; and methods of using cyanine-containing compounds for cancer cell imaging, cancer cell growth inhibition, and detecting cancer cells, for example.

More specifically, provided are compounds having two cyanine ring ("CyR") structures as defined below, linked by an optionally substituted linker as shown below:

Formula A

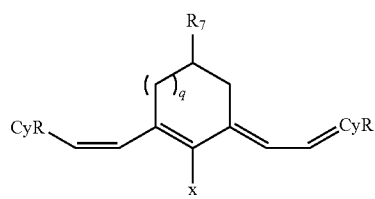

where X is selected from the group consisting of: hydrogen, halogen, CN, Me, phenyl, OH, OMe, OPh, 4-O-Ph-$NH_2$, 4-O-Ph-$CH_2CH_2COOH$, 4-O-Ph-$CH_2CH_2CONHS$ (where NHS is a group derived from N-hydroxysuccinimide or succinimide-N-oxy), NH-Ph, NHEt, SEt, S-Ph, 4-S-Ph-COOH, 4-S-Ph-OH, 4-O-Ph-COOH, 4-O-Ph-NCS, and 4-S-Ph-NCS; q is 0 (forming a cyclopentene ring) or 1 (forming a cyclohexene ring); $R_7$ is selected from H and $COOR^9$, where $R^9$ is H, $CH_3$, or $CH_2CH_3$. In one embodiment, when q is 0, R7 is H.

CyR structures include those shown below. The CyR structures are generally heterocyclic end units comprising cyanine. The line shown on the ring structures below show where the linker is attached. Each portion of the molecule may have various substituents.

Exemplary CyR structures

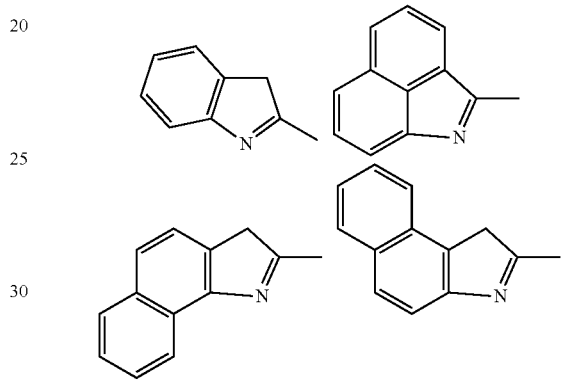

In one embodiment, heptamethine cyanine dyes are provided (having 7 carbons between CyR structures).

It is understood that one or both nitrogen atoms in the cyanine ring structures may have a positive charge, in which case a suitable counterion is associated with the compound. The CyR structures may be substituted with any suitable substituent on any suitable ring position, for example, as shown below:

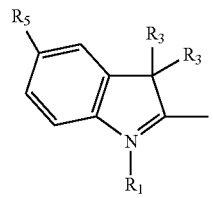

where $R_5$ is selected from H, OH, OMe, halogen, $NH_2$, NHR, $NR_2$ and COOH, where each R is independently C1-C6 alkyl and $R_1$ and $R_3$ are as described elsewhere herein.

Other cyanine ring structures include:

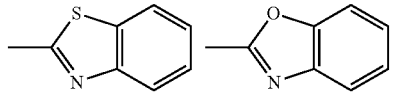

In an embodiment, provided are compounds having formula B:

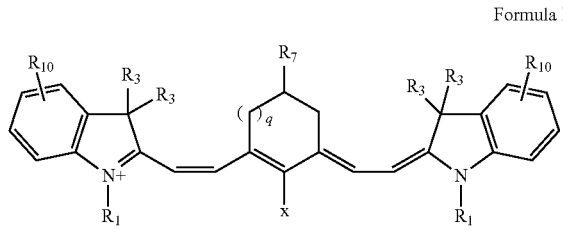

Formula B where X is selected from the group consisting of: hydrogen, halogen, CN, Me, phenyl, OH, OMe, OPh, 4-O-Ph-NH$_2$, 4-O-Ph-CH$_2$CH$_2$COOH, 4-O-Ph-CH$_2$CH$_2$CONHS, NH-Ph, NHEt, SEt, S-Ph, 4-S-Ph-COOH, 4-S-Ph-OH, 4-O-Ph-COOH, 4-O-Ph-NCS, and 4-S-Ph-NCS; q is 0 or 1; R$_7$ is selected from H and COOR$^9$, where R$^9$ is H, CH$_3$, or CH$_2$CH$_3$; each R$_1$ is independently in each instance, (CH$_2$)$_m$R$_A$, where m is an integer from 1 to 12, R$_A$ is independently CH$_3$, NH$_2$, SH, COOH, SO$_3$H, OH, halogen and CO—N-hydroxysuccinimide; each R$_{10}$ is independently in each instance selected from H, OH, OMe, halogen, NH$_2$, NHR, NR$_2$ and COOH, where each R is independently C1-C6 alkyl; each R$_3$ is independently in each instance, selected from the group consisting of: methyl and phenyl. R$_{10}$ may be independently attached to any available position on each ring.

In an embodiment, X is Cl and each R$_3$ is CH$_3$. In an embodiment, R$_1$ is (CH2)$_m$COOH and m is 1-6. In an embodiment, R$_1$ is (CH$_2$)$_m$SO$_3$H and m is 1-6. In an embodiment, R$_1$ is (CH$_2$)$_m$CH$_3$ and m is 1-6. In an embodiment, the cyanine-containing compound is MHI-148, IR783, or IR780. In an embodiment, the cyanine-containing compound is a compound of Formula A. In an embodiment, the cyanine-containing compound is a compound of Formula B.

The compounds of the invention are preferentially taken up in cancer cells as compared to normal cells. Using this characteristic, many uses of the compounds of the invention are appreciated by one of ordinary skill in the art. Some of these uses are described herein. Provided are methods of imaging cancer cells comprising: introducing an imaging amount of a cyanine-containing compound to cancer cells, exposing said cells to electromagnetic radiation; and detecting light emission from the cyanine-containing compound. As used herein, an "imaging amount" is an amount which is taken up by a cell and results in a detectable emission of light from the cell. Determination of "imaging amounts" which produce a detectable signal and do not result in toxicity to the cell is well within the level of skill of one of ordinary skill in the art without undue experimentation. As used herein, "introducing" a cyanine-containing compound to cancer cells means cancer cells and a cyanine-containing compound are placed together so that a reaction or interaction can occur. "Introducing" may occur by two substances being mixed together; by one substance being added to another; by physical contact of one substance (or example a cell) with another substance (for example a cyanine-containing compound) (e.g., a smear); and by other methods as known in the art.

Also provided are methods of treating cancer comprising: administering a cytotoxic amount of a cyanine-containing compound to cancer cells. As used herein, a "cytotoxic amount" is an amount which results in cell death of at least one percent of the cancer cells. A specific example of a cytotoxic amount is an amount which results in cell death of at least fifty percent of the cancer cells (LD$_{50}$).

Also provided is a method of identifying cancer in a biological sample comprising: introducing an imaging amount of a cyanine-containing compound to a biological sample; exposing the biological sample to excitation light; and detecting the emission of light, wherein emission of light from the biological sample indicates cancer is present in the biological sample. In one embodiment, the cancer identified is circulating tumor cells is a biological fluid. In one embodiment, the biological fluid is selected from the group consisting of: blood, a blood component, urine, saliva, and materials excreted from the body. In one embodiment, the biological fluid is blood or a blood component. In one embodiment, the biological sample is a tissue sample.

The methods described here can be used to type animals and detect premalignant changes in cells in animal models and in human clinical specimens, for both transgenic and nontransgenic animals.

The compounds and methods described here can be used to track dying cancer cells during or after therapy or to determine if a tumor fails to respond to a therapy, by monitoring the accumulation of a compound of the invention in live cells and tissues. These methods are useful for monitoring the success or failure of cancer therapy, and are useful to adjust therapy if necessary.

The methods described here can be used as a screening index for in vivo and in vitro tumor angiogenesis response to a drug, because a tumor that has reduced angiogenesis after angiogenic drug therapy retains lesser amounts of a compound of the invention as compared to a tumor that has increased angiogenesis after angiogenic drug therapy.

The compounds of the invention are stable in formalin. Thus, the compounds of the invention are useful in monitoring post formalin fixed tissue or other biological specimens. In one embodiment, the compounds of the invention are used to monitor or confirm the surgical margin of tumors (i.e. if the tumor cells penetrated surgical margin or stayed inside) by contacting one or more compounds of the invention with a tissue sample and determining if the sample exhibits light emission above background after appropriate excitation. Cancer cells in the surgical margin are used to predict subsequent recurrent disease.

Compounds of the invention are useful in various surgical and medical procedures, as will be appreciated by one having ordinary skill in the art. For example, during active surgery, surgeons can use the methods of the invention to identify which lymph node may contain tumors and which area may have disseminated tumor cells. The current practice is taking a frozen section and a step section of the suspected areas by pathologists. The methods of the invention provide real-time results.

The amount of dye uptake can be used to determine the stages and grades of benign or cancer related diseases for use in diagnosis of indolent and virulent cancers. Compounds of the invention may be tagged by radioactive groups or other functional groups, as known in the art.

The methods described here can be applied to in vitro cells or in vivo cells. The radiation used in the methods is any suitable wavelength which the cyanine-containing compound absorbs. These wavelengths are determined by the absorption maxima of the dyes, and are typically, but not limited to, on the hypsochromic side of the absorption spectra for achieving maximum separation from the fluorescence observation wavelength. Methods of selecting suitable wavelengths are known in the art. In an embodiment, suitable light sources emit radiation in the near infrared region. In an embodiment, excitation light having a wavelength from 600 and 1600 nm is used. In an embodiment, excitation light having a wavelength between 650 and 850 nm is used. In an embodiment, fluorescence having a wavelength between 700 to 850 nm is detected.

Various types of cancer can be imaged using the methods and compound described here. In separate embodiments, the cancer cells are selected from lymphoma, Hodgkin's Disease, myeloid leukemia, bladder cancer, brain cancer, head and neck cancer, kidney cancer, lung cancer, myeloma, neuroblastoma/glioblastoma, ovarian cancer, cervical cancer, bone cancer, thyroid cancer, adrenal gland cancers, cholangiocarcinoma, pancreatic cancer, prostate cancer, skin cancer, liver cancer, testicular cancer, melanoma, colon cancer, and breast cancer.

Suitable imaging devices and methods of using the same are known in the art and include fluorescence imaging. Suitable detection methods include FACS, scanning microscopy, histochemical and immunohistochemical methods using appropriate detection devices. Staining methods of cells are known in the art. Conventional excitation light sources such as lasers, halogen light sources, xenon light sources and other suitable light sources may be used. Various optical filters and light directing elements and methods may be used, as is known in the art.

BRIEF DESCRIPTION OF THE DRAWINGS

FIG. 1-2 shows negative imaging of normal human cells with MHI-148. No image was obtained from normal human cells exposed to MHI-148.

FIG. 2 shows human ARCaP$_M$ prostate cancer cells can be imaged in vitro in test tubes (A) and in vivo in live mice when as tumor cells were delivered either subcutaneously (B) or intraosseously (C).

DETAILED DESCRIPTION OF THE INVENTION

Figure 1:
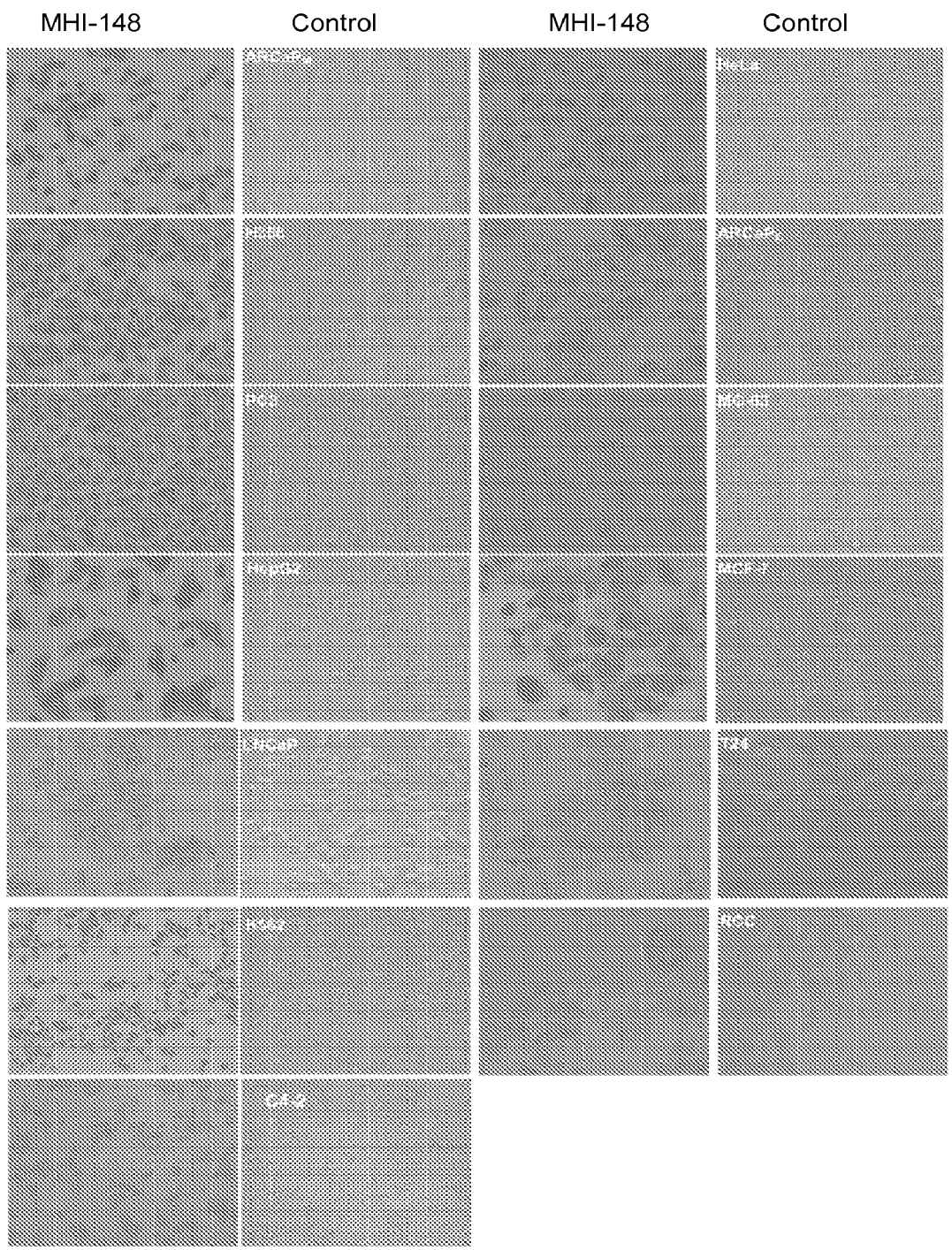
FIG. 1-1 shows positive imaging of various human cancer cells using MHI-148. Control shows no image from cells not exposed to MHI-148.

The following description provides nonlimiting examples of some embodiments of the invention.

Specific embodiments of compounds of the invention are provided in Formula C,

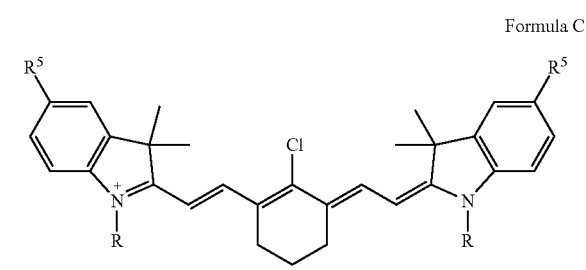

Formula C wherein each $R^5$ is independently selected from the group consisting of: H, OH, OMe, halogen, $NH_2$, $NHR^B$, $NR^B_2$, COOH, where each $R^B$ is independently C1-C3 alkyl and R is as provided below.

Particular exemplary compounds are shown below:

| Compound Number | Groups in Formula C |
|---|---|
| MHI-148 | R = $(CH_2)_5COOH$, $R^5$ = H |
| MHI-25 (aka IR783) | R = $(CH_2)_4SO_3H$, $R^5$ = H |
| MHI-78 | R = $(CH_2)_2OH$, $R^5$ = H |
| MHI-160 | R = $(CH_2)_4COOH$ |
| MHI-161 | R = $(CH_2)_3COOH$ |
| MHI-200 | R = $(CH_2)_nCOOH$ |
| | n = 2-4, 7-10, 12 |
| IR780 | R = $(CH_2)_2CH_3$ |

In embodiments of the invention, the R substituent groups on the cyanine ring groups are not the same. In embodiments of the invention, the R substituent groups on the cyanine ring groups are the same. Certain embodiments of the invention contain two acid R groups. Certain embodiments of the invention contain one acid and one ester R group. Certain embodiments of the invention contain two ester R groups.

In embodiments of the invention, cyanine-containing compounds according to any of Formulas (I), (II), (III), (IV), (V), (VI), (VII), or (VIII) are provided.

Formula (I)

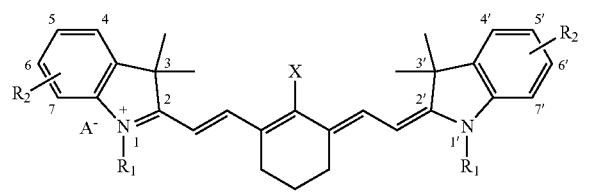

Formula (II)

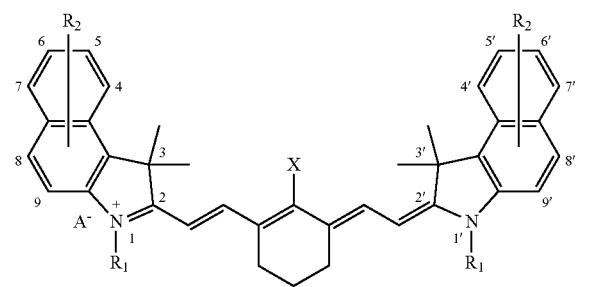

Formula (III)

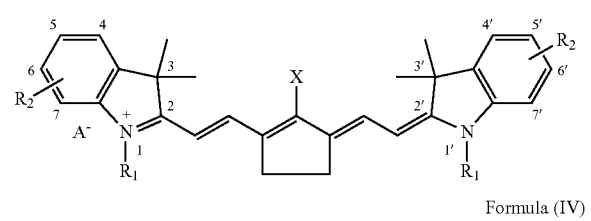

Formula (IV)

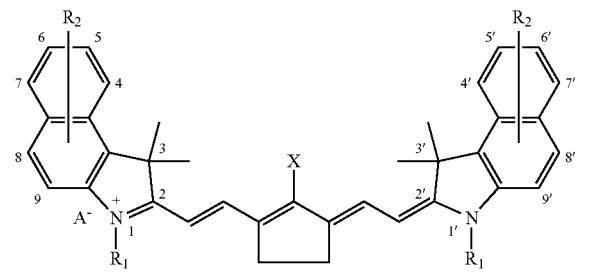

Formula (V)

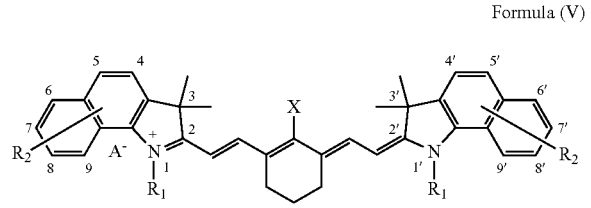

Formula (VI)

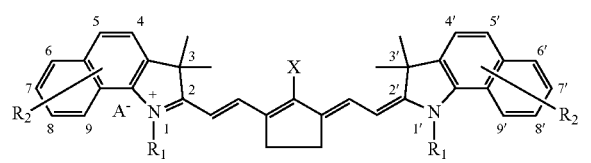

-continued

Formula (VII)

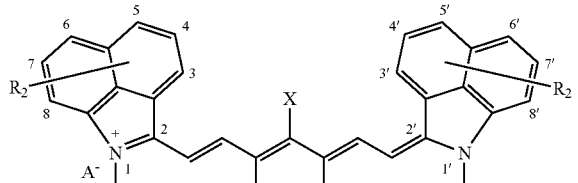

Formula (VIII)

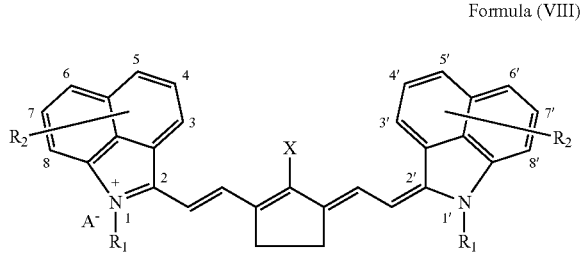

wherein:
each $R_2$ is independently in each instance selected from the group consisting of hydrogen, any electron withdrawing group (EWG) and any electron donating group (EDG) attached at one or more of positions 3, 3', 4, 4', 5, 5', 6, 6', 7, 7', 8, 8'; each $R_1$ is independently in each instance selected from the group consisting of: hydrogen, alkyl, aryl, aralkyl, alkylsulfonato, alkylcarboxylic, alkylamino; X is chlorine or bromine; and counteranion A is selected from the group consisting of: iodide, bromide, arylsulfonato, alkylsulfonato, tetrafluoroborate; chloride and any other pharmaceutically acceptable anions. Electron donating and withdrawing groups are known in the art. Some examples of electron donating groups include: OH, OMe, $NH_2$, $NHR^B$, and $NR^B_2$, where $R^B$ is C1-C6 alkyl. Some examples of electron withdrawing groups include: halogen, COOH, CN, $SO_3Na$, COOH, COOMe, and COOEt.

Some specific embodiments of compounds of the invention are listed below.

Formula 1:

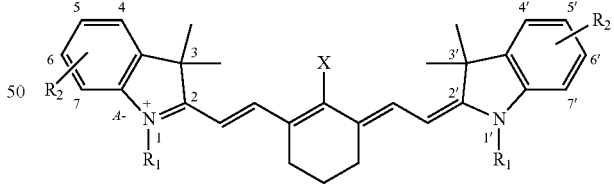

| X | $R_1$ | $R_2$*** |
|---|---|---|
| Br | Methyl | H, EDG, EWG |
| Br | Ethyl | H, EDG, EWG |
| Br | Propyl | H, EDG, EWG |
| Br | Butyl* | H, EDG, EWG |
| Br | Pentyl* | H, EDG, EWG |
| Br | Hexyl* | H, EDG, EWG |
| Br | Heptyl* | H, EDG, EWG |
| Br | Octyl* | H, EDG, EWG |
| Br | Nonyl* | H, EDG, EWG |
| Br | Decyl* | H, EDG, EWG |
| Br | Undecyl* | H, EDG, EWG |
| Br | Dodecyl* | H, EDG, EWG |
| Br | Tridecyl* | H, EDG, EWG |

Formula 1:

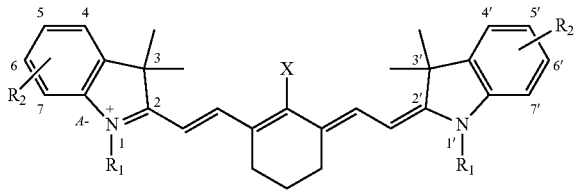

| X | R₁ | R₂*** |
|---|---|---|
| Br | Tetradecyl* | H, EDG, EWG |
| Br | Pentadecyl* | H, EDG, EWG |
| Br | Hexadecyl* | H, EDG, EWG |
| Br | Heptadecyl* | H, EDG, EWG |
| Br | Octadecyl* | H, EDG, EWG |
| Br | Phenyl** | H, EDG, EWG |
| Br | Benzyl** | H, EDG, EWG |
| Br | Napthyl** | H, EDG, EWG |
| Br | $CH_2-SO_3^-$ | H, EDG, EWG |
| Br | $(CH_2)_2-SO_3^-$ | H, EDG, EWG |
| Br | $(CH_2)_3-SO_3^-$ | H, EDG, EWG |
| Br | $(CH_2)_4-SO_3^-$ | H, EDG, EWG |
| Br | $(CH_2)_5-SO_3^-$ | H, EDG, EWG |
| Br | $(CH_2)_6-SO_3^-$ | H, EDG, EWG |
| Br | $(CH_2)_7-SO_3^-$ | H, EDG, EWG |
| Br | $(CH_2)_8-SO_3^-$ | H, EDG, EWG |
| Br | $(CH_2)_9-SO_3^-$ | H, EDG, EWG |
| Br | $(CH_2)_{10}-SO_3^-$ | H, EDG, EWG |
| Br | $(CH_2)_{11}-SO_3^-$ | H, EDG, EWG |
| Br | $(CH_2)_{12}-SO_3^-$ | H, EDG, EWG |
| Br | $(CH_2)_{13}-SO_3^-$ | H, EDG, EWG |
| Br | $(CH_2)_{14}-SO_3^-$ | H, EDG, EWG |
| Br | $(CH_2)_{15}-SO_3^-$ | H, EDG, EWG |
| Br | $(CH_2)_{16}-SO_3^-$ | H, EDG, EWG |
| Br | $(CH_2)_{17}-SO_3^-$ | H, EDG, EWG |
| Br | $(CH_2)_{18}-SO_3^-$ | H, EDG, EWG |
| Br | $CH_2-CO_2^-$ | H, EDG, EWG |
| Br | $(CH_2)_2-CO_2^-$ | H, EDG, EWG |
| Br | $(CH_2)_3-CO_2^-$ | H, EDG, EWG |
| Br | $(CH_2)_4-CO_2^-$ | H, EDG, EWG |
| Br | $(CH_2)_5-CO_2^-$ | H, EDG, EWG |
| Br | $(CH_2)_6-CO_2^-$ | H, EDG, EWG |
| Br | $(CH_2)_7-CO_2^-$ | H, EDG, EWG |
| Br | $(CH_2)_8-CO_2^-$ | H, EDG, EWG |
| Br | $(CH_2)_9-CO_2^-$ | H, EDG, EWG |
| Br | $(CH_2)_{10}-CO_2^-$ | H, EDG, EWG |
| Br | $(CH_2)_{11}-CO_2^-$ | H, EDG, EWG |
| Br | $(CH_2)_{12}-CO_2^-$ | H, EDG, EWG |
| Br | $(CH_2)_{13}-CO_2^-$ | H, EDG, EWG |
| Br | $(CH_2)_{14}-CO_2^-$ | H, EDG, EWG |
| Br | $(CH_2)_{15}-CO_2^-$ | H, EDG, EWG |
| Br | $(CH_2)_{16}-CO_2^-$ | H, EDG, EWG |
| Br | $(CH_2)_{17}-CO_2^-$ | H, EDG, EWG |
| Br | $(CH_2)_{18}-CO_2^-$ | H, EDG, EWG |
| Br | $CH_2-NH_2$ | H, EDG, EWG |
| Br | $(CH_2)_2-NH_2$ | H, EDG, EWG |
| Br | $(CH_2)_3-NH_2$ | H, EDG, EWG |
| Br | $(CH_2)_4-NH_2$ | H, EDG, EWG |
| Br | $(CH_2)_5-NH_2$ | H, EDG, EWG |
| Br | $(CH_2)_6-NH_2$ | H, EDG, EWG |
| Br | $(CH_2)_7-NH_2$ | H, EDG, EWG |
| Br | $(CH_2)_8-NH_2$ | H, EDG, EWG |
| Br | $(CH_2)_9-NH_2$ | H, EDG, EWG |
| Br | $(CH_2)_{10}-NH_2$ | H, EDG, EWG |
| Br | $(CH_2)_{11}-NH_2$ | H, EDG, EWG |
| Br | $(CH_2)_{12}-NH_2$ | H, EDG, EWG |
| Br | $(CH_2)_{13}-NH_2$ | H, EDG, EWG |
| Br | $(CH_2)_{14}-NH_2$ | H, EDG, EWG |
| Br | $(CH_2)_{15}-NH_2$ | H, EDG, EWG |

Formula 1:

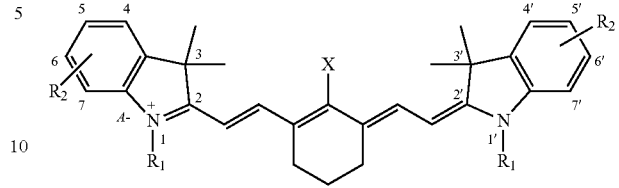

| X | R₁ | R₂*** |
|---|---|---|
| Br | $(CH_2)_{16}-NH_2$ | H, EDG, EWG |
| Br | $(CH_2)_{17}-NH_2$ | H, EDG, EWG |
| Br | $(CH_2)_{18}-NH_2$ | H, EDG, EWG |

*Each alkyl chain is optionally branched with an alkyl chain, aryl ring, heteroaryl, aralkyl group, or unsaturation at any position on the chain.
**The phenyl, benzyl, or napthyl ring is optionally ortho-, meta-, or para-substituted with 1-3 substituents selected from halo, alkoxy, hydroxyl, $CF_3$, $NO_2$, $NH_2$, NHR, or $NR_2$, where R is H or C1-C3 alkyl.
***The R₂ group is H, any electron withdrawing group, or any electron donating group.

The A group is I, Cl, Br, $OSO_2R$, $BF_4$, $ClO_4$, or any pharmaceutically acceptable anion. In embodiments of compounds of Formulas 1-8, X can be Cl or Br, for example.

Formula 2:

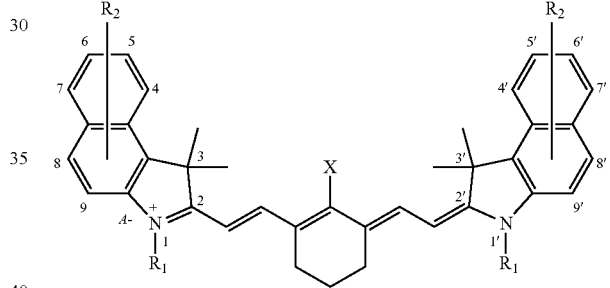

| X | R₁ | R₂*** |
|---|---|---|
| Br | Methyl | H, EDG, EWG |
| Br | Ethyl | H, EDG, EWG |
| Br | Propyl | H, EDG, EWG |
| Br | Butyl* | H, EDG, EWG |
| Br | Pentyl* | H, EDG, EWG |
| Br | Hexyl* | H, EDG, EWG |
| Br | Heptyl* | H, EDG, EWG |
| Br | Octyl* | H, EDG, EWG |
| Br | Nonyl* | H, EDG, EWG |
| Br | Decyl* | H, EDG, EWG |
| Br | Undecyl* | H, EDG, EWG |
| Br | Dodecyl* | H, EDG, EWG |
| Br | Tridecyl* | H, EDG, EWG |
| Br | Tetradecyl* | H, EDG, EWG |
| Br | Pentadecyl* | H, EDG, EWG |
| Br | Hexadecyl* | H, EDG, EWG |
| Br | Heptadecyl* | H, EDG, EWG |
| Br | Octadecyl* | H, EDG, EWG |
| Br | Phenyl** | H, EDG, EWG |
| Br | Benzyl** | H, EDG, EWG |
| Br | Napthyl** | H, EDG, EWG |
| Br | $CH_2-SO_3^-$ | H, EDG, EWG |
| Br | $(CH_2)_2-SO_3^-$ | H, EDG, EWG |
| Br | $(CH_2)_3-SO_3^-$ | H, EDG, EWG |
| Br | $(CH_2)_4-SO_3^-$ | H, EDG, EWG |
| Br | $(CH_2)_5-SO_3^-$ | H, EDG, EWG |
| Br | $(CH_2)_6-SO_3^-$ | H, EDG, EWG |
| Br | $(CH_2)_7-SO_3^-$ | H, EDG, EWG |
| Br | $(CH_2)_8-SO_3^-$ | H, EDG, EWG |
| Br | $(CH_2)_9-SO_3^-$ | H, EDG, EWG |

Formula 2:

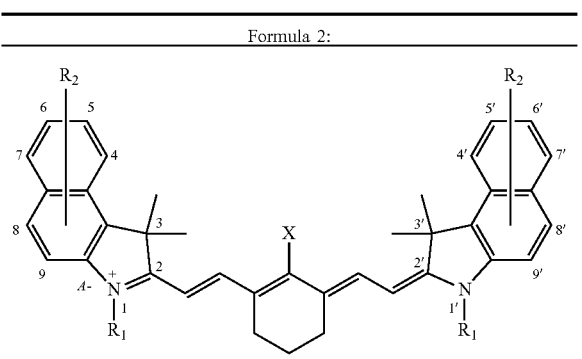

| X | $R_1$ | $R_2$*** |
|---|---|---|
| Br | $(CH_2)_{10}$—$SO_3^-$ | H, EDG, EWG |
| Br | $(CH_2)_{11}$—$SO_3^-$ | H, EDG, EWG |
| Br | $(CH_2)_{12}$—$SO_3^-$ | H, EDG, EWG |
| Br | $(CH_2)_{13}$—$SO_3^-$ | H, EDG, EWG |
| Br | $(CH_2)_{14}$—$SO_3^-$ | H, EDG, EWG |
| Br | $(CH_2)_{15}$—$SO_3^-$ | H, EDG, EWG |
| Br | $(CH_2)_{16}$—$SO_3^-$ | H, EDG, EWG |
| Br | $(CH_2)_{17}$—$SO_3^-$ | H, EDG, EWG |
| Br | $(CH_2)_{18}$—$SO_3^-$ | H, EDG, EWG |
| Br | $CH_2$—$CO_2^-$ | H, EDG, EWG |
| Br | $(CH_2)_2$—$CO_2^-$ | H, EDG, EWG |
| Br | $(CH_2)_3$—$CO_2^-$ | H, EDG, EWG |
| Br | $(CH_2)_4$—$CO_2^-$ | H, EDG, EWG |
| Br | $(CH_2)_5$—$CO_2^-$ | H, EDG, EWG |
| Br | $(CH_2)_6$—$CO_2^-$ | H, EDG, EWG |
| Br | $(CH_2)_7$—$CO_2^-$ | H, EDG, EWG |
| Br | $(CH_2)_8$—$CO_2^-$ | H, EDG, EWG |
| Br | $(CH_2)_9$—$CO_2^-$ | H, EDG, EWG |
| Br | $(CH_2)_{10}$—$CO_2^-$ | H, EDG, EWG |
| Br | $(CH_2)_{11}$—$CO_2^-$ | H, EDG, EWG |
| Br | $(CH_2)_{12}$—$CO_2^-$ | H, EDG, EWG |
| Br | $(CH_2)_{13}$—$CO_2^-$ | H, EDG, EWG |
| Br | $(CH_2)_{14}$—$CO_2^-$ | H, EDG, EWG |
| Br | $(CH_2)_{15}$—$CO_2^-$ | H, EDG, EWG |
| Br | $(CH_2)_{16}$—$CO_2^-$ | H, EDG, EWG |
| Br | $(CH_2)_{17}$—$CO_2^-$ | H, EDG, EWG |
| Br | $(CH_2)_{18}$—$CO_2^-$ | H, EDG, EWG |
| Br | $CH_2$—$NH_2$ | H, EDG, EWG |
| Br | $(CH_2)_2$—$NH_2$ | H, EDG, EWG |
| Br | $(CH_2)_3$—$NH_2$ | H, EDG, EWG |
| Br | $(CH_2)_4$—$NH_2$ | H, EDG, EWG |
| Br | $(CH_2)_5$—$NH_2$ | H, EDG, EWG |
| Br | $(CH_2)_6$—$NH_2$ | H, EDG, EWG |
| Br | $(CH_2)_7$—$NH_2$ | H, EDG, EWG |
| Br | $(CH_2)_8$—$NH_2$ | H, EDG, EWG |
| Br | $(CH_2)_9$—$NH_2$ | H, EDG, EWG |
| Br | $(CH_2)_{10}$—$NH_2$ | H, EDG, EWG |
| Br | $(CH_2)_{11}$—$NH_2$ | H, EDG, EWG |
| Br | $(CH_2)_{12}$—$NH_2$ | H, EDG, EWG |
| Br | $(CH_2)_{13}$—$NH_2$ | H, EDG, EWG |
| Br | $(CH_2)_{14}$—$NH_2$ | H, EDG, EWG |
| Br | $(CH_2)_{15}$—$NH_2$ | H, EDG, EWG |
| Br | $(CH_2)_{16}$—$NH_2$ | H, EDG, EWG |
| Br | $(CH_2)_{17}$—$NH_2$ | H, EDG, EWG |
| Br | $(CH_2)_{18}$—$NH_2$ | H, EDG, EWG |

*Each alkyl chain is optionally branched with an alkyl chain, aryl ring, heteroaryl, aralkyl group, or unsaturation at any position on the chain.
**The phenyl, benzyl, or napthyl ring is optionally ortho-, meta-, or para-substituted with 1-3 substituents selected from halo, alkoxy, hydroxyl, $CF_3$, $NO_2$, $NH_2$, NHR, or $NR_2$.
***The $R_2$ group is H, any electron withdrawing group, or any electron donating group.

The A group is I, Cl, Br, $OSO_2R$, $BF_4$, $ClO_4$, or any pharmaceutically acceptable anions.

In one embodiment of compounds of Formula 2, X=Br, $R_1$=Me, and A=$ClO_4$. In one embodiment of compounds of Formula 2, when compounds are claimed, compounds are not included where: X=Br, $R_1$=Me, and A=$ClO_4$.

Formula 3:

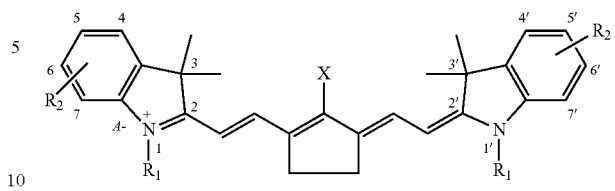

| X | $R_1$ | $R_2$*** |
|---|---|---|
| Br | Methyl | H, EDG, EWG |
| Br | Ethyl | H, EDG, EWG |
| Cl, Br | Propyl | H, EDG, EWG |
| Cl, Br | Butyl* | H, EDG, EWG |
| Cl, Br | Pentyl* | H, EDG, EWG |
| Cl, Br | Hexyl* | H, EDG, EWG |
| Cl, Br | Heptyl* | H, EDG, EWG |
| Cl, Br | Octyl* | H, EDG, EWG |
| Cl, Br | Nonyl* | H, EDG, EWG |
| Cl, Br | Decyl* | H, EDG, EWG |
| Cl, Br | Undecyl* | H, EDG, EWG |
| Cl, Br | Dodecyl* | H, EDG, EWG |
| Cl, Br | Tridecyl* | H, EDG, EWG |
| Cl, Br | Tetradecyl* | H, EDG, EWG |
| Cl, Br | Pentadecyl* | H, EDG, EWG |
| Cl, Br | Hexadecyl* | H, EDG, EWG |
| Cl, Br | Heptadecyl* | H, EDG, EWG |
| Cl, Br | Octadecyl* | H, EDG, EWG |
| Cl, Br | Phenyl** | H, EDG, EWG |
| Cl, Br | Benzyl** | H, EDG, EWG |
| Cl, Br | Napthyl** | H, EDG, EWG |
| Cl, Br | $CH_2$—$SO_3^-$ | H, EDG, EWG |
| Cl, Br | $(CH_2)_2$—$SO_3^-$ | H, EDG, EWG |
| Cl, Br | $(CH_2)_3$—$SO_3^-$ | H, EDG, EWG |
| Cl, Br | $(CH_2)_4$—$SO_3^-$ | H, EDG, EWG |
| Cl, Br | $(CH_2)_5$—$SO_3^-$ | H, EDG, EWG |
| Cl, Br | $(CH_2)_6$—$SO_3^-$ | H, EDG, EWG |
| Cl, Br | $(CH_2)_7$—$SO_3^-$ | H, EDG, EWG |
| Cl, Br | $(CH_2)_8$—$SO_3^-$ | H, EDG, EWG |
| Cl, Br | $(CH_2)_9$—$SO_3^-$ | H, EDG, EWG |
| Cl, Br | $(CH_2)_{10}$—$SO_3^-$ | H, EDG, EWG |
| Cl, Br | $(CH_2)_{11}$—$SO_3^-$ | H, EDG, EWG |
| Cl, Br | $(CH_2)_{12}$—$SO_3^-$ | H, EDG, EWG |
| Cl, Br | $(CH_2)_{13}$—$SO_3^-$ | H, EDG, EWG |
| Cl, Br | $(CH_2)_{14}$—$SO_3^-$ | H, EDG, EWG |
| Cl, Br | $(CH_2)_{15}$—$SO_3^-$ | H, EDG, EWG |
| Cl, Br | $(CH_2)_{16}$—$SO_3^-$ | H, EDG, EWG |
| Cl, Br | $(CH_2)_{17}$—$SO_3^-$ | H, EDG, EWG |
| Cl, Br | $(CH_2)_{18}$—$SO_3^-$ | H, EDG, EWG |
| Cl, Br | $CH_2$—$CO_2^-$ | H, EDG, EWG |
| Cl, Br | $(CH_2)_2$—$CO_2^-$ | H, EDG, EWG |
| Cl, Br | $(CH_2)_3$—$CO_2^-$ | H, EDG, EWG |
| Cl, Br | $(CH_2)_4$—$CO_2^-$ | H, EDG, EWG |
| Cl, Br | $(CH_2)_5$—$CO_2^-$ | H, EDG, EWG |
| Cl, Br | $(CH_2)_6$—$CO_2^-$ | H, EDG, EWG |
| Cl, Br | $(CH_2)_7$—$CO_2^-$ | H, EDG, EWG |
| Cl, Br | $(CH_2)_8$—$CO_2^-$ | H, EDG, EWG |
| Cl, Br | $(CH_2)_9$—$CO_2^-$ | H, EDG, EWG |
| Cl, Br | $(CH_2)_{10}$—$CO_2^-$ | H, EDG, EWG |
| Cl, Br | $(CH_2)_{11}$—$CO_2^-$ | H, EDG, EWG |
| Cl, Br | $(CH_2)_{12}$—$CO_2^-$ | H, EDG, EWG |
| Cl, Br | $(CH_2)_{13}$—$CO_2^-$ | H, EDG, EWG |
| Cl, Br | $(CH_2)_{14}$—$CO_2^-$ | H, EDG, EWG |
| Cl, Br | $(CH_2)_{15}$—$CO_2^-$ | H, EDG, EWG |
| Cl, Br | $(CH_2)_{16}$—$CO_2^-$ | H, EDG, EWG |
| Cl, Br | $(CH_2)_{17}$—$CO_2^-$ | H, EDG, EWG |
| Cl, Br | $(CH_2)_{18}$—$CO_2^-$ | H, EDG, EWG |
| Cl, Br | $CH_2$—$NH_2$ | H, EDG, EWG |
| Cl, Br | $(CH_2)_2$—$NH_2$ | H, EDG, EWG |
| Cl, Br | $(CH_2)_3$—$NH_2$ | H, EDG, EWG |
| Cl, Br | $(CH_2)_4$—$NH_2$ | H, EDG, EWG |
| Cl, Br | $(CH_2)_5$—$NH_2$ | H, EDG, EWG |
| Cl, Br | $(CH_2)_6$—$NH_2$ | H, EDG, EWG |
| Cl, Br | $(CH_2)_7$—$NH_2$ | H, EDG, EWG |
| Cl, Br | $(CH_2)_8$—$NH_2$ | H, EDG, EWG |
| Cl, Br | $(CH_2)_9$—$NH_2$ | H, EDG, EWG |
| Cl, Br | $(CH_2)_{10}$—$NH_2$ | H, EDG, EWG |

Formula 3:

[Chemical structure diagram of Formula 3 showing a bis-indole cyanine dye with positions labeled 1-7 and 1'-7', containing R₁, R₂, X, and A⁻ substituents]

| X | $R_1$ | $R_2$*** |
|---|---|---|
| Cl, Br | $(CH_2)_{11}$—$NH_2$ | H, EDG, EWG |
| Cl, Br | $(CH_2)_{12}$—$NH_2$ | H, EDG, EWG |
| Cl, Br | $(CH_2)_{13}$—$NH_2$ | H, EDG, EWG |
| Cl, Br | $(CH_2)_{14}$—$NH_2$ | H, EDG, EWG |
| Cl, Br | $(CH_2)_{15}$—$NH_2$ | H, EDG, EWG |
| Cl, Br | $(CH_2)_{16}$—$NH_2$ | H, EDG, EWG |
| Cl, Br | $(CH_2)_{17}$—$NH_2$ | H, EDG, EWG |
| Cl, Br | $(CH_2)_{18}$—$NH_2$ | H, EDG, EWG |

*Each alkyl chain is optionally branched with an alkyl chain, aryl ring, heteroaryl, aralkyl group, or unsaturation at any position on the chain.
**The phenyl, benzyl, or napthyl ring is optionally ortho-, meta- or para-substituted with 1-3 substituents selected from halo, alkoxy, hydroxyl, $CF_3$, $NO_2$, $NH_2$, NHR, or $NR_2$.
***The $R_2$ group is H, any electron withdrawing group, or any electron donating group.

The A group is I, Cl, Br, $OSO_2R$, $BF_4$, $ClO_4$, or any pharmaceutically acceptable anion.

In embodiments of compounds of Formula 3, X=Cl, $R_1$=Me; X=Cl, $R_1$=Et; X=Cl, $R_1$=n-Bu, $R_2$=H, $SO_2NH_2$, and A=I, $ClO_4$; X=Cl, $R_1$=$(CH_2)_6CH_3$, $R_2$=$SO_2CH_3$, and A=$ClO_4$; X=Cl, $R_1$=$(CH_2)_{11}CH_3$, $R_2$=Cl, and A=$BF_4$; X=Cl, $R_1$=Ph, and A=$BF_4$ or —$OSO_2R$; X=Cl, $R_1$=$CH_2CH$=$CH_2$ and A=$ClO_4$; X=Cl, $R_1$=$(CH_2)_3CH$=$CH_2$, and A=$ClO_4$; X=Cl, $R_1$=$CH_2OH$, $R_2$=OEt, and A=$ClO_4$; X=Cl, $R_1$=$(CH_2)_2OH$ and A=$ClO_4$; X=Cl, $R_1$=$CH_2OMe$, $R_2$=Cl, and A=$ClO_4$; X=Cl, $R_1$=$CH_2O(CH_2)_3CH_3$, $R_2$=Cl, and A=$BF_4$; X=Cl, $R_1$=$CH_2OCH_2CH_3$, $R_2$=Cl, and A=$ClO_4$; X=Cl, $R_1$=$CH_2CH_2OMe$ and A=$SbF_6$; X=Cl, $R_1$=$CH_2CH_2OEt$ and A=$ClO_4$; X=Cl, $R_1$=$CH_2CH_2O(CH_2)_5CH_3$ and A=$ClO_4$; X=Cl, $R_1$=$(CH_2)_4OAc$, $R_2$=$CO_2Et$, and A=$ClO_4$; X=Cl, $R_1$=$CH_2CH_2O_2CNHPhh$, $R_2$=$CO_2Me$ or Cl, and A=$ClO_4$ or Br.

In embodiments of compounds of Formula 3, where compounds are claimed, the compounds are not included where: X=Cl, $R_1$=Me; X=Cl, $R_1$=Et; X=Cl, $R_1$=n-Bu, $R_2$=H, $SO_2NH_2$, and A=I, $ClO_4$; X=Cl, $R_1$=$(CH_2)_6CH_3$, $R_2$=$SO_2CH_3$, and A=$ClO_4$; X=Cl, $R_1$=$(CH_2)_{11}CH_3$, $R_2$=Cl, and A=$BF_4$; X=Cl, $R_1$=Ph, and A=$BF_4$ or —$OSO_2R$; X=Cl, $R_1$=$CH_2CH$=$CH_2$ and A=$ClO_4$; X=Cl, $R_1$=$(CH_2)_3CH$=$CH_2$, and A=$ClO_4$; X=Cl, $R_1$=$CH_2OH$, $R_2$=OEt, and A=$ClO_4$; X=Cl, $R_1$=$(CH_2)_2OH$ and A=$ClO_4$; X=Cl, $R_1$=$CH_2OMe$, $R_2$=Cl, and A=$ClO_4$; X=Cl, $R_1$=$CH_2O(CH_2)_3CH_3$, $R_2$=Cl, and A=$BF_4$; X=Cl, $R_1$=$CH_2OCH_2CH_3$, $R_2$=Cl, and A=$ClO_4$; X=Cl, $R_1$=$CH_2CH_2OMe$ and A=$SbF_6$; X=Cl, $R_1$=$CH_2CH_2OEt$ and A=$ClO_4$; X=Cl, $R_1$=$CH_2CH_2O(CH_2)_5CH_3$ and A=$ClO_4$; X=Cl, $R_1$=$(CH_2)_4OAc$, $R_2$=$CO_2Et$, and A=$ClO_4$; X=Cl, $R_1$=$CH_2CH_2O_2CNHPhh$, $R_2$=$CO_2Me$ or Cl, and A=$ClO_4$ or Br.

Formula 4:

[Chemical structure diagram of Formula 4 showing a bis-benz[e]indole cyanine dye with positions labeled 1-9 and 1'-9', containing R₁, R₂, X, and A⁻ substituents]

| X | $R_1$ | $R_2$*** |
|---|---|---|
| Cl, Br | Methyl | H, EDG, EWG |
| Cl, Br | Ethyl | H, EDG, EWG |
| Cl, Br | Propyl | H, EDG, EWG |
| Cl, Br | Butyl* | H, EDG, EWG |
| Cl, Br | Pentyl* | H, EDG, EWG |
| Cl, Br | Hexyl* | H, EDG, EWG |
| Cl, Br | Heptyl* | H, EDG, EWG |
| Cl, Br | Octyl* | H, EDG, EWG |
| Cl, Br | Nonyl* | H, EDG, EWG |
| Cl, Br | Decyl* | H, EDG, EWG |
| Cl, Br | Undecyl* | H, EDG, EWG |
| Cl, Br | Dodecyl* | H, EDG, EWG |
| Cl, Br | Tridecyl* | H, EDG, EWG |
| Cl, Br | Tetradecyl* | H, EDG, EWG |
| Cl, Br | Pentadecyl* | H, EDG, EWG |
| Cl, Br | Hexadecyl* | H, EDG, EWG |
| Cl, Br | Heptadecyl* | H, EDG, EWG |
| Cl, Br | Octadecyl* | H, EDG, EWG |
| Cl, Br | Phenyl** | H, EDG, EWG |
| Cl, Br | Benzyl** | H, EDG, EWG |
| Cl, Br | Napthyl** | H, EDG, EWG |
| Cl, Br | $CH_2$—$SO_3^-$ | H, EDG, EWG |
| Cl, Br | $(CH_2)_2$—$SO_3^-$ | H, EDG, EWG |
| Cl, Br | $(CH_2)_3$—$SO_3^-$ | H, EDG, EWG |
| Cl, Br | $(CH_2)_4$—$SO_3^-$ | H, EDG, EWG |
| Cl, Br | $(CH_2)_5$—$SO_3^-$ | H, EDG, EWG |
| Cl, Br | $(CH_2)_6$—$SO_3^-$ | H, EDG, EWG |
| Cl, Br | $(CH_2)_7$—$SO_3^-$ | H, EDG, EWG |
| Cl, Br | $(CH_2)_8$—$SO_3^-$ | H, EDG, EWG |
| Cl, Br | $(CH_2)_9$—$SO_3^-$ | H, EDG, EWG |
| Cl, Br | $(CH_2)_{10}$—$SO_3^-$ | H, EDG, EWG |
| Cl, Br | $(CH_2)_{11}$—$SO_3^-$ | H, EDG, EWG |
| Cl, Br | $(CH_2)_{12}$—$SO_3^-$ | H, EDG, EWG |
| Cl, Br | $(CH_2)_{13}$—$SO_3^-$ | H, EDG, EWG |
| Cl, Br | $(CH_2)_{14}$—$SO_3^-$ | H, EDG, EWG |
| Cl, Br | $(CH_2)_{15}$—$SO_3^-$ | H, EDG, EWG |
| Cl, Br | $(CH_2)_{16}$—$SO_3^-$ | H, EDG, EWG |
| Cl, Br | $(CH_2)_{17}$—$SO_3^-$ | H, EDG, EWG |
| Cl, Br | $(CH_2)_{18}$—$SO_3^-$ | H, EDG, EWG |
| Cl, Br | $CH_2$—$CO_2^-$ | H, EDG, EWG |
| Cl, Br | $(CH_2)_2$—$CO_2^-$ | H, EDG, EWG |
| Cl, Br | $(CH_2)_3$—$CO_2^-$ | H, EDG, EWG |
| Cl, Br | $(CH_2)_4$—$CO_2^-$ | H, EDG, EWG |
| Cl, Br | $(CH_2)_5$—$CO_2^-$ | H, EDG, EWG |
| Cl, Br | $(CH_2)_6$—$CO_2^-$ | H, EDG, EWG |
| Cl, Br | $(CH_2)_7$—$CO_2^-$ | H, EDG, EWG |
| Cl, Br | $(CH_2)_8$—$CO_2^-$ | H, EDG, EWG |
| Cl, Br | $(CH_2)_9$—$CO_2^-$ | H, EDG, EWG |
| Cl, Br | $(CH_2)_{10}$—$CO_2^-$ | H, EDG, EWG |
| Cl, Br | $(CH_2)_{11}$—$CO_2^-$ | H, EDG, EWG |
| Cl, Br | $(CH_2)_{12}$—$CO_2^-$ | H, EDG, EWG |
| Cl, Br | $(CH_2)_{13}$—$CO_2^-$ | H, EDG, EWG |
| Cl, Br | $(CH_2)_{14}$—$CO_2^-$ | H, EDG, EWG |
| Cl, Br | $(CH_2)_{15}$—$CO_2^-$ | H, EDG, EWG |
| Cl, Br | $(CH_2)_{16}$—$CO_2^-$ | H, EDG, EWG |
| Cl, Br | $(CH_2)_{17}$—$CO_2^-$ | H, EDG, EWG |
| Cl, Br | $(CH_2)_{18}$—$CO_2^-$ | H, EDG, EWG |
| Cl, Br | $CH_2$—$NH_2$ | H, EDG, EWG |
| Cl, Br | $(CH_2)_2$—$NH_2$ | H, EDG, EWG |
| Cl, Br | $(CH_2)_3$—$NH_2$ | H, EDG, EWG |
| Cl, Br | $(CH_2)_4$—$NH_2$ | H, EDG, EWG |
| Cl, Br | $(CH_2)_5$—$NH_2$ | H, EDG, EWG |

Formula 4:

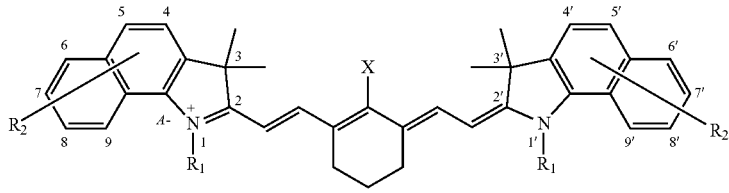

| X | $R_1$ | $R_2$*** |
|---|---|---|
| Cl, Br | $(CH_2)_6$—$NH_2$ | H, EDG, EWG |
| Cl, Br | $(CH_2)_7$—$NH_2$ | H, EDG, EWG |
| Cl, Br | $(CH_2)_8$—$NH_2$ | H, EDG, EWG |
| Cl, Br | $(CH_2)_9$—$NH_2$ | H, EDG, EWG |
| Cl, Br | $(CH_2)_{10}$—$NH_2$ | H, EDG, EWG |
| Cl, Br | $(CH_2)_{11}$—$NH_2$ | H, EDG, EWG |
| Cl, Br | $(CH_2)_{12}$—$NH_2$ | H, EDG, EWG |
| Cl, Br | $(CH_2)_{13}$—$NH_2$ | H, EDG, EWG |
| Cl, Br | $(CH_2)_{14}$—$NH_2$ | H, EDG, EWG |
| Cl, Br | $(CH_2)_{15}$—$NH_2$ | H, EDG, EWG |
| Cl, Br | $(CH_2)_{16}$—$NH_2$ | H, EDG, EWG |
| Cl, Br | $(CH_2)_{17}$—$NH_2$ | H, EDG, EWG |
| Cl, Br | $(CH_2)_{18}$—$NH_2$ | H, EDG, EWG |

*Each alkyl chain is optionally branched with an alkyl chain, aryl ring, heteroaryl, aralkyl group, or unsaturation at any position on the chain.
**The phenyl, benzyl, or napthyl ring is optionally ortho-, meta-, or para-substituted with 1-3 substituents selected from halo, alkoxy, hydroxyl, $CF_3$, $NO_2$, NHR, or $NR_2$.
***The $R_2$ group is H, any electron withdrawing group, or any electron donating group.

The A group is I, Cl, Br, $OSO_2R$, $BF_4$, $ClO_4$, or any pharmaceutically acceptable anion.

In embodiments of compounds of Formula 4, X=Cl, $R_1$=Me, $R_2$=H or $CH_2OAc$, and A=$SbF_6$, —$CO_2(CF_2)_2CF_3$, —$OSO_2(CF_2)_3CF_3$, —$OSO_2C_6H_4CH_3$; X=Cl, $R_1$=Et, and A=$ClO_4$ or I; X=Cl, $R_1$=n-Pr, and A=$PF_6^-$, $OSO_2C_6H_4CH_3$, or Cl; X=Cl, $R_1$=n-Bu, and A=$PF_6^-$, $OSO_2C_6H_4CH_3$, Br, or $ClO_4$; X=Cl, $R_1$=—$(CH_2)_9CH_3$, and A=$OSO_2CF_3$; X=Cl, $R_1$=—$CH_2OPh$ and A=$ClO_4^-$; X=Cl, $R_1$=—$CH_2CH_2OMe$, and A=$N(SO_2CF_3)_2$; X=Cl, $R_1$=—$CH_2CH_2OH$, and A=Br; X=Cl, $R_1$=—$(CH_2)_5CO_2H$ and A=—$OSO_2R$; and X=Cl, $R_1$=—$(CH_2)_4CH$=$CH_2$ and A=$ClO_4$. In embodiments of compounds of Formula 4, when compounds are claimed, compounds of Formula 4 do not include those compounds where: X=Cl, $R_1$=Me, $R_2$=H or $CH_2OAc$, and A=$SbF_6$, —$CO_2(CF_2)_2CF_3$, —$OSO_2(CF_2)_3CF_3$, —$OSO_2C_6H_4CH_3$; X=Cl, $R_1$=Et, and A=$ClO_4$ or I; X=Cl, $R_1$=n-Pr, and A=$PF_6^-$, $OSO_2C_6H_4CH_3$, or Cl; X=Cl, $R_1$=n-Bu, and A=$PF_6^-$, $OSO_2C_6H_4CH_3$, Br, or $ClO_4$; X=Cl, $R_1$=—$(CH_2)_9CH_3$, and A=$OSO_2CF_3$; X=Cl, $R_1$=—$CH_2OPh$ and A=$ClO_4^-$; X=Cl, $R_1$=—$CH_2CH_2OMe$, and A=$N(SO_2CF_3)_2$; X=Cl, $R_1$=—$CH_2CH_2OH$, and A=Br; X=Cl, $R_1$=—$(CH_2)_5CO_2H$ and A=—$OSO_2R$; and X=Cl, $R_1$=—$(CH_2)_4CH$=$CH_2$ and A=$ClO_4$.

Formula 5:

| X | $R_1$ | $R_2$*** |
|---|---|---|
| Cl, Br | Methyl | H, EDG, EWG |
| Cl, Br | Ethyl | H, EDG, EWG |
| Cl, Br | Propyl | H, EDG, EWG |
| Cl, Br | Butyl* | H, EDG, EWG |
| Cl, Br | Pentyl* | H, EDG, EWG |
| Cl, Br | Hexyl* | H, EDG, EWG |
| Cl, Br | Heptyl* | H, EDG, EWG |
| Cl, Br | Octyl* | H, EDG, EWG |
| Cl, Br | Nonyl* | H, EDG, EWG |
| Cl, Br | Decyl* | H, EDG, EWG |
| Cl, Br | Undecyl* | H, EDG, EWG |
| Cl, Br | Dodecyl* | H, EDG, EWG |
| Cl, Br | Tridecyl* | H, EDG, EWG |
| Cl, Br | Tetradecyl* | H, EDG, EWG |
| Cl, Br | Pentadecyl* | H, EDG, EWG |
| Cl, Br | Hexadecyl* | H, EDG, EWG |
| Cl, Br | Heptadecyl* | H, EDG, EWG |
| Cl, Br | Octadecyl* | H, EDG, EWG |
| Cl, Br | Phenyl** | H, EDG, EWG |
| Cl, Br | Benzyl** | H, EDG, EWG |
| Cl, Br | Napthyl** | H, EDG, EWG |
| Cl, Br | $CH_2$—$SO_3^-$ | H, EDG, EWG |
| Cl, Br | $(CH_2)_2$—$SO_3^-$ | H, EDG, EWG |
| Cl, Br | $(CH_2)_3$—$SO_3^-$ | H, EDG, EWG |
| Cl, Br | $(CH_2)_4$—$SO_3^-$ | H, EDG, EWG |

-continued

Formula 5:

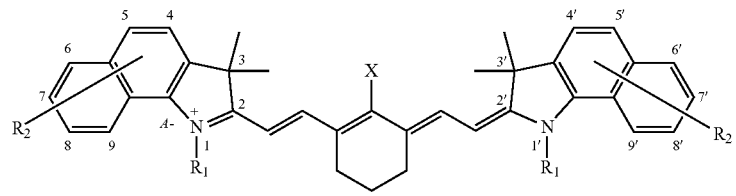

| X | $R_1$ | $R_2$*** |
|---|---|---|
| Cl, Br | $(CH_2)_5-SO_3^-$ | H, EDG, EWG |
| Cl, Br | $(CH_2)_6-SO_3^-$ | H, EDG, EWG |
| Cl, Br | $(CH_2)_7-SO_3^-$ | H, EDG, EWG |
| Cl, Br | $(CH_2)_8-SO_3^-$ | H, EDG, EWG |
| Cl, Br | $(CH_2)_9-SO_3^-$ | H, EDG, EWG |
| Cl, Br | $(CH_2)_{10}-SO_3^-$ | H, EDG, EWG |
| Cl, Br | $(CH_2)_{11}-SO_3^-$ | H, EDG, EWG |
| Cl, Br | $(CH_2)_{12}-SO_3^-$ | H, EDG, EWG |
| Cl, Br | $(CH_2)_{13}-SO_3^-$ | H, EDG, EWG |
| Cl, Br | $(CH_2)_{14}-SO_3^-$ | H, EDG, EWG |
| Cl, Br | $(CH_2)_{15}-SO_3^-$ | H, EDG, EWG |
| Cl, Br | $(CH_2)_{16}-SO_3^-$ | H, EDG, EWG |
| Cl, Br | $(CH_2)_{17}-SO_3^-$ | H, EDG, EWG |
| Cl, Br | $(CH_2)_{18}-SO_3^-$ | H, EDG, EWG |
| Cl, Br | $CH_2-CO_2^-$ | H, EDG, EWG |
| Cl, Br | $(CH_2)_2-CO_2^-$ | H, EDG, EWG |
| Cl, Br | $(CH_2)_3-CO_2^-$ | H, EDG, EWG |
| Cl, Br | $(CH_2)_4-CO_2^-$ | H, EDG, EWG |
| Cl, Br | $(CH_2)_5-CO_2^-$ | H, EDG, EWG |
| Cl, Br | $(CH_2)_6-CO_2^-$ | H, EDG, EWG |
| Cl, Br | $(CH_2)_7-CO_2^-$ | H, EDG, EWG |
| Cl, Br | $(CH_2)_8-CO_2^-$ | H, EDG, EWG |
| Cl, Br | $(CH_2)_9-CO_2^-$ | H, EDG, EWG |
| Cl, Br | $(CH_2)_{10}-CO_2^-$ | H, EDG, EWG |
| Cl, Br | $(CH_2)_{11}-CO_2^-$ | H, EDG, EWG |
| Cl, Br | $(CH_2)_{12}-CO_2^-$ | H, EDG, EWG |
| Cl, Br | $(CH_2)_{13}-CO_2^-$ | H, EDG, EWG |
| Cl, Br | $(CH_2)_{14}-CO_2^-$ | H, EDG, EWG |
| Cl, Br | $(CH_2)_{15}-CO_2^-$ | H, EDG, EWG |
| Cl, Br | $(CH_2)_{16}-CO_2^-$ | H, EDG, EWG |
| Cl, Br | $(CH_2)_{17}-CO_2^-$ | H, EDG, EWG |
| Cl, Br | $(CH_2)_{18}-CO_2^-$ | H, EDG, EWG |
| Cl, Br | $CH_2-NH_2$ | H, EDG, EWG |
| Cl, Br | $(CH_2)_2-NH_2$ | H, EDG, EWG |
| Cl, Br | $(CH_2)_3-NH_2$ | H, EDG, EWG |
| Cl, Br | $(CH_2)_4-NH_2$ | H, EDG, EWG |
| Cl, Br | $(CH_2)_5-NH_2$ | H, EDG, EWG |
| Cl, Br | $(CH_2)_6-NH_2$ | H, EDG, EWG |
| Cl, Br | $(CH_2)_7-NH_2$ | H, EDG, EWG |
| Cl, Br | $(CH_2)_8-NH_2$ | H, EDG, EWG |
| Cl, Br | $(CH_2)_9-NH_2$ | H, EDG, EWG |
| Cl, Br | $(CH_2)_{10}-NH_2$ | H, EDG, EWG |
| Cl, Br | $(CH_2)_{11}-NH_2$ | H, EDG, EWG |
| Cl, Br | $(CH_2)_{12}-NH_2$ | H, EDG, EWG |
| Cl, Br | $(CH_2)_{13}-NH_2$ | H, EDG, EWG |
| Cl, Br | $(CH_2)_{14}-NH_2$ | H, EDG, EWG |
| Cl, Br | $(CH_2)_{15}-NH_2$ | H, EDG, EWG |
| Cl, Br | $(CH_2)_{16}-NH_2$ | H, EDG, EWG |
| Cl, Br | $(CH_2)_{17}-NH_2$ | H, EDG, EWG |
| Cl, Br | $(CH_2)_{18}-NH_2$ | H, EDG, EWG |

*Each alkyl chain is optionally branched with an alkyl chain, aryl ring, heteroaryl, aralkyl group, or unsaturation at any position on the chain.
**The phenyl, benzyl, or napthyl ring is optionally ortho-, meta-, or para-substituted with 1-3 substituents selected from halo, alkoxy, hydroxyl, $CF_3$, $NO_2$, $NH_2$, NHR, or $NR_2$.
***The $R_2$ group is H, any electron withdrawing group, or any electron donating group.

The A group is I, Cl, Br, $OSO_2R$, $BF_4$, $ClO_4$, or any pharmaceutically acceptable anion.

In one embodiment of compounds of Formula 5, X=Cl, R, $R_1$=Me, $R_2$=H, and A=$SbF_6$ and —$OSO_2C_6H_4CH_3$. In one embodiment of compounds of Formula 5, when compounds are claimed, compounds of Formula 5 do not include those compounds where: X=Cl, $R_1$=Me, $R_2$=H, and A=$SbF_6$ and —$OSO_2C_6H_4CH_3$.

Formula 6:

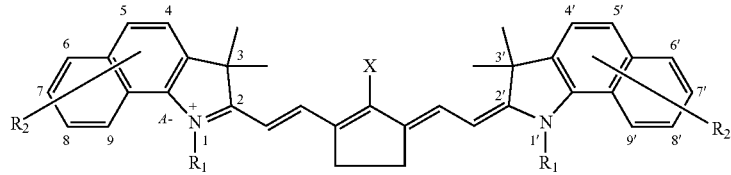

| X | $R_1$ | $R_2$*** |
|---|---|---|
| Cl, Br | Methyl | H, EDG, EWG |
| Cl, Br | Ethyl | H, EDG, EWG |
| Cl, Br | Propyl | H, EDG, EWG |
| Cl, Br | Butyl* | H, EDG, EWG |
| Cl, Br | Pentyl* | H, EDG, EWG |
| Cl, Br | Hexyl* | H, EDG, EWG |
| Cl, Br | Heptyl* | H, EDG, EWG |
| Cl, Br | Octyl* | H, EDG, EWG |
| Cl, Br | Nonyl* | H, EDG, EWG |
| Cl, Br | Decyl* | H, EDG, EWG |
| Cl, Br | Undecyl* | H, EDG, EWG |
| Cl, Br | Dodecyl* | H, EDG, EWG |
| Cl, Br | Tridecyl* | H, EDG, EWG |
| Cl, Br | Tetradecyl* | H, EDG, EWG |
| Cl, Br | Pentadecyl* | H, EDG, EWG |
| Cl, Br | Hexadecyl* | H, EDG, EWG |
| Cl, Br | Heptadecyl* | H, EDG, EWG |
| Cl, Br | Octadecyl* | H, EDG, EWG |
| Cl, Br | Phenyl** | H, EDG, EWG |
| Cl, Br | Benzyl** | H, EDG, EWG |
| Cl, Br | Naphthyl** | H, EDG, EWG |
| Cl, Br | $CH_2$—$SO_3^-$ | H, EDG, EWG |
| Cl, Br | $(CH_2)_2$—$SO_3^-$ | H, EDG, EWG |
| Cl, Br | $(CH_2)_3$—$SO_3^-$ | H, EDG, EWG |
| Cl, Br | $(CH_2)_4$—$SO_3^-$ | H, EDG, EWG |
| Cl, Br | $(CH_2)_5$—$SO_3^-$ | H, EDG, EWG |
| Cl, Br | $(CH_2)_6$—$SO_3^-$ | H, EDG, EWG |
| Cl, Br | $(CH_2)_7$—$SO_3^-$ | H, EDG, EWG |
| Cl, Br | $(CH_2)_8$—$SO_3^-$ | H, EDG, EWG |
| Cl, Br | $(CH_2)_9$—$SO_3^-$ | H, EDG, EWG |
| Cl, Br | $(CH_2)_{10}$—$SO_3^-$ | H, EDG, EWG |
| Cl, Br | $(CH_2)_{11}$—$SO_3^-$ | H, EDG, EWG |
| Cl, Br | $(CH_2)_{12}$—$SO_3^-$ | H, EDG, EWG |
| Cl, Br | $(CH_2)_{13}$—$SO_3^-$ | H, EDG, EWG |
| Cl, Br | $(CH_2)_{14}$—$SO_3^-$ | H, EDG, EWG |
| Cl, Br | $(CH_2)_{15}$—$SO_3^-$ | H, EDG, EWG |
| Cl, Br | $(CH_2)_{16}$—$SO_3^-$ | H, EDG, EWG |
| Cl, Br | $(CH_2)_{17}$—$SO_3^-$ | H, EDG, EWG |
| Cl, Br | $(CH_2)_{18}$—$SO_3^-$ | H, EDG, EWG |
| Cl, Br | $CH_2$—$CO_2^-$ | H, EDG, EWG |
| Cl, Br | $(CH_2)_2$—$CO_2^-$ | H, EDG, EWG |
| Cl, Br | $(CH_2)_3$—$CO_2^-$ | H, EDG, EWG |
| Cl, Br | $(CH_2)_4$—$CO_2^-$ | H, EDG, EWG |
| Cl, Br | $(CH_2)_5$—$CO_2^-$ | H, EDG, EWG |
| Cl, Br | $(CH_2)_6$—$CO_2^-$ | H, EDG, EWG |
| Cl, Br | $(CH_2)_7$—$CO_2^-$ | H, EDG, EWG |
| Cl, Br | $(CH_2)_8$—$CO_2^-$ | H, EDG, EWG |
| Cl, Br | $(CH_2)_9$—$CO_2^-$ | H, EDG, EWG |
| Cl, Br | $(CH_2)_{10}$—$CO_2^-$ | H, EDG, EWG |
| Cl, Br | $(CH_2)_{11}$—$CO_2^-$ | H, EDG, EWG |
| Cl, Br | $(CH_2)_{12}$—$CO_2^-$ | H, EDG, EWG |
| Cl, Br | $(CH_2)_{13}$—$CO_2^-$ | H, EDG, EWG |
| Cl, Br | $(CH_2)_{14}$—$CO_2^-$ | H, EDG, EWG |
| Cl, Br | $(CH_2)_{15}$—$CO_2^-$ | H, EDG, EWG |
| Cl, Br | $(CH_2)_{16}$—$CO_2^-$ | H, EDG, EWG |
| Cl, Br | $(CH_2)_{17}$—$CO_2^-$ | H, EDG, EWG |
| Cl, Br | $(CH_2)_{18}$—$CO_2^-$ | H, EDG, EWG |
| Cl, Br | $CH_2$—$NH_2$ | H, EDG, EWG |
| Cl, Br | $(CH_2)_2$—$NH_2$ | H, EDG, EWG |
| Cl, Br | $(CH_2)_3$—$NH_2$ | H, EDG, EWG |
| Cl, Br | $(CH_2)_4$—$NH_2$ | H, EDG, EWG |

Formula 6:

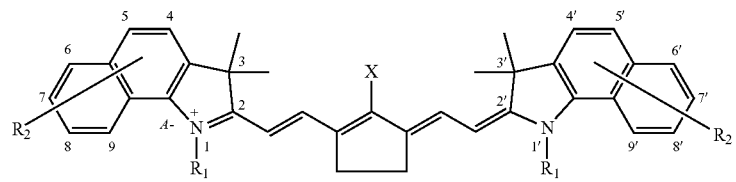

| X | $R_1$ | $R_2$*** |
|---|---|---|
| Cl, Br | $(CH_2)_5-NH_2$ | H, EDG, EWG |
| Cl, Br | $(CH_2)_6-NH_2$ | H, EDG, EWG |
| Cl, Br | $(CH_2)_7-NH_2$ | H, EDG, EWG |
| Cl, Br | $(CH_2)_8-NH_2$ | H, EDG, EWG |
| Cl, Br | $(CH_2)_9-NH_2$ | H, EDG, EWG |
| Cl, Br | $(CH_2)_{10}-NH_2$ | H, EDG, EWG |
| Cl, Br | $(CH_2)_{11}-NH_2$ | H, EDG, EWG |
| Cl, Br | $(CH_2)_{12}-NH_2$ | H, EDG, EWG |
| Cl, Br | $(CH_2)_{13}-NH_2$ | H, EDG, EWG |
| Cl, Br | $(CH_2)_{14}-NH_2$ | H, EDG, EWG |
| Cl, Br | $(CH_2)_{15}-NH_2$ | H, EDG, EWG |
| Cl, Br | $(CH_2)_{16}-NH_2$ | H, EDG, EWG |
| Cl, Br | $(CH_2)_{17}-NH_2$ | H, EDG, EWG |
| Cl, Br | $(CH_2)_{18}-NH_2$ | H, EDG, EWG |

*Each alkyl chain is optionally branched with an alkyl chain, aryl ring, heteroaryl, aralkyl group, or unsaturation at any position on the chain.
**The phenyl, benzyl, or napthyl ring is optionally ortho-, meta-, or para-substituted with 1-3 substituents selected from halo, alkoxy, hydroxyl, $CF_3$, $NO_2$, $NH_2$, NHR, or $NR_2$.
***The $R_2$ group is H, any electron withdrawing group, or any electron donating group.

The A group is I, Cl, Br, $OSO_2R$, $BF_4$, $ClO_4$, or any pharmaceutically acceptable anion.

In embodiments of compounds of Formula 6, X=Cl, $R_1$=n-Bu, $R_2$=H, and A=$SbF_6$; X=Cl, $R_1$=—$CH_2OMe$, and A=Cl; X=Cl, $R_1$=—$(CH_2)_2COOEt$, and A=$ClO_4$. In embodiments of compounds of Formula 6, when compounds of Formula 6 are claimed, the compounds are not included where: X=Cl, $R_1$=n-Bu, $R_2$=H, and A=$SbF_6$; X=Cl, $R_1$=—$CH_2OMe$, and A=Cl; X=Cl, $R_1$=—$(CH_2)_2COOEt$, and A=$ClO_4$.

Formula 7:

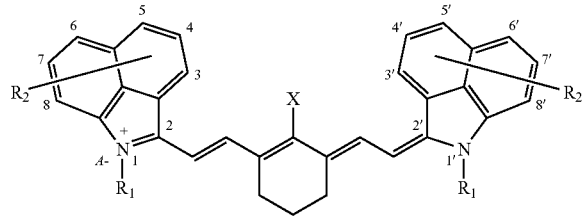

| X | $R_1$ | $R_2$*** |
|---|---|---|
| Cl, Br | Methyl | H, EDG, EWG |
| Cl, Br | Ethyl | H, EDG, EWG |
| Cl, Br | Propyl | H, EDG, EWG |
| Cl, Br | Butyl* | H, EDG, EWG |
| Cl, Br | Pentyl* | H, EDG, EWG |
| Cl, Br | Hexyl* | H, EDG, EWG |
| Cl, Br | Heptyl* | H, EDG, EWG |
| Cl, Br | Octyl* | H, EDG, EWG |
| Cl, Br | Nonyl* | H, EDG, EWG |
| Cl, Br | Decyl* | H, EDG, EWG |
| Cl, Br | Undecyl* | H, EDG, EWG |
| Cl, Br | Dodecyl* | H, EDG, EWG |
| Cl, Br | Tridecyl* | H, EDG, EWG |
| Cl, Br | Tetradecyl* | H, EDG, EWG |
| Cl, Br | Pentadecyl* | H, EDG, EWG |

Formula 7:

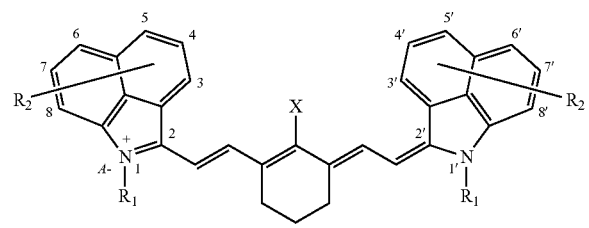

| X | $R_1$ | $R_2$*** |
|---|---|---|
| Cl, Br | Hexadecyl* | H, EDG, EWG |
| Cl, Br | Heptadecyl* | H, EDG, EWG |
| Cl, Br | Octadecyl* | H, EDG, EWG |
| Cl, Br | Phenyl** | H, EDG, EWG |
| Cl, Br | Benzyl** | H, EDG, EWG |
| Cl, Br | Naphthyl** | H, EDG, EWG |
| Cl, Br | $CH_2-SO_3^-$ | H, EDG, EWG |
| Cl, Br | $(CH_2)_2-SO_3^-$ | H, EDG, EWG |
| Cl, Br | $(CH_2)_3-SO_3^-$ | H, EDG, EWG |
| Cl, Br | $(CH_2)_4-SO_3^-$ | H, EDG, EWG |
| Cl, Br | $(CH_2)_5-SO_3^-$ | H, EDG, EWG |
| Cl, Br | $(CH_2)_6-SO_3^-$ | H, EDG, EWG |
| Cl, Br | $(CH_2)_7-SO_3^-$ | H, EDG, EWG |
| Cl, Br | $(CH_2)_8-SO_3^-$ | H, EDG, EWG |
| Cl, Br | $(CH_2)_9-SO_3^-$ | H, EDG, EWG |
| Cl, Br | $(CH_2)_{10}-SO_3^-$ | H, EDG, EWG |
| Cl, Br | $(CH_2)_{11}-SO_3^-$ | H, EDG, EWG |
| Cl, Br | $(CH_2)_{12}-SO_3^-$ | H, EDG, EWG |
| Cl, Br | $(CH_2)_{13}-SO_3^-$ | H, EDG, EWG |
| Cl, Br | $(CH_2)_{14}-SO_3^-$ | H, EDG, EWG |
| Cl, Br | $(CH_2)_{15}-SO_3^-$ | H, EDG, EWG |
| Cl, Br | $(CH_2)_{16}-SO_3^-$ | H, EDG, EWG |
| Cl, Br | $(CH_2)_{17}-SO_3^-$ | H, EDG, EWG |
| Cl, Br | $(CH_2)_{18}-SO_3^-$ | H, EDG, EWG |
| Cl, Br | $CH_2-CO_2^-$ | H, EDG, EWG |
| Cl, Br | $(CH_2)_2-CO_2^-$ | H, EDG, EWG |
| Cl, Br | $(CH_2)_3-CO_2^-$ | H, EDG, EWG |

Formula 7:

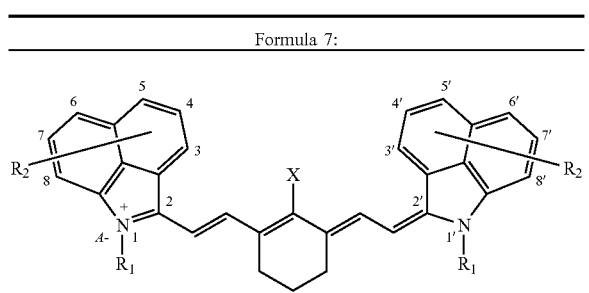

| X | $R_1$ | $R_2$*** |
|---|---|---|
| Cl, Br | $(CH_2)_4-CO_2^-$ | H, EDG, EWG |
| Cl, Br | $(CH_2)_5-CO_2^-$ | H, EDG, EWG |
| Cl, Br | $(CH_2)_6-CO_2^-$ | H, EDG, EWG |
| Cl, Br | $(CH_2)_7-CO_2^-$ | H, EDG, EWG |
| Cl, Br | $(CH_2)_8-CO_2^-$ | H, EDG, EWG |
| Cl, Br | $(CH_2)_9-CO_2^-$ | H, EDG, EWG |
| Cl, Br | $(CH_2)_{10}-CO_2^-$ | H, EDG, EWG |
| Cl, Br | $(CH_2)_{11}-CO_2^-$ | H, EDG, EWG |
| Cl, Br | $(CH_2)_{12}-CO_2^-$ | H, EDG, EWG |
| Cl, Br | $(CH_2)_{13}-CO_2^-$ | H, EDG, EWG |
| Cl, Br | $(CH_2)_{14}-CO_2^-$ | H, EDG, EWG |
| Cl, Br | $(CH_2)_{15}-CO_2^-$ | H, EDG, EWG |
| Cl, Br | $(CH_2)_{16}-CO_2^-$ | H, EDG, EWG |
| Cl, Br | $(CH_2)_{17}-CO_2^-$ | H, EDG, EWG |
| Cl, Br | $(CH_2)_{18}-CO_2^-$ | H, EDG, EWG |
| Cl, Br | $CH_2-NH_2$ | H, EDG, EWG |
| Cl, Br | $(CH_2)_2-NH_2$ | H, EDG, EWG |
| Cl, Br | $(CH_2)_3-NH_2$ | H, EDG, EWG |
| Cl, Br | $(CH_2)_4-NH_2$ | H, EDG, EWG |
| Cl, Br | $(CH_2)_5-NH_2$ | H, EDG, EWG |
| Cl, Br | $(CH_2)_6-NH_2$ | H, EDG, EWG |
| Cl, Br | $(CH_2)_7-NH_2$ | H, EDG, EWG |
| Cl, Br | $(CH_2)_8-NH_2$ | H, EDG, EWG |
| Cl, Br | $(CH_2)_9-NH_2$ | H, EDG, EWG |
| Cl, Br | $(CH_2)_{10}-NH_2$ | H, EDG, EWG |
| Cl, Br | $(CH_2)_{11}-NH_2$ | H, EDG, EWG |
| Cl, Br | $(CH_2)_{12}-NH_2$ | H, EDG, EWG |
| Cl, Br | $(CH_2)_{13}-NH_2$ | H, EDG, EWG |
| Cl, Br | $(CH_2)_{14}-NH_2$ | H, EDG, EWG |
| Cl, Br | $(CH_2)_{15}-NH_2$ | H, EDG, EWG |
| Cl, Br | $(CH_2)_{16}-NH_2$ | H, EDG, EWG |
| Cl, Br | $(CH_2)_{17}-NH_2$ | H, EDG, EWG |
| Cl, Br | $(CH_2)_{18}-NH_2$ | H, EDG, EWG |

*Each alkyl chain is optionally branched with an alkyl chain, cycloalkyl, aryl ring, heterocycle, aralkyl group, or unsaturation at any position on the chain.
**The phenyl, benzyl, or napthyl ring is optionally ortho-, meta-, or para-substituted with 1-3 substituents selected from halo, alkoxy, hydroxyl, $CF_3$, $NO_2$, $NH_2$, NHR, or $NR_2$.
***The $R_2$ group is H, any electron withdrawing group, or any electron donating group.

The A group is I, Cl, Br, $OSO_2R$, $BF_4$, $ClO_4$, or any pharmaceutically acceptable anion.

In embodiments of compounds of Formula 7, X=Cl, $R_1$=n-Bu, $R_2$=H or Cl, and A=$BF_4$ or $PF_6$; X=Cl, $R_1$=Et, $R_2$=H, and A=I or Cl; X=Cl, $R_1$=decyl, $R_2$=H or Me, and A=Cl or $BF_4$; X=Cl, $R_1$=dodecyl, $R_2$=H, Cl, SPh, or OMe, and A=Cl, $BF_4$; X=Cl, $R_1$=allyl, and A=I; X=Cl, $R_1$=octadecyl, and A=$ClO_4$; and X=Cl, =—$(CH_2)_2COOH$, and A=$BF_4$. In embodiments of compounds of Formula 7, when compounds of Formula 7 are claimed, the compounds are not included where: X=Cl, $R_1$=n-Bu, $R_2$=H or Cl, and A=$BF_4$ or $PF_6$; X=Cl, $R_1$=Et, $R_2$=H, and A=I or Cl; X=Cl, $R_1$=decyl, $R_2$=H or Me, and A=Cl or $BF_4$; X=Cl, $R_1$=dodecyl, $R_2$=H, Cl, SPh, or OMe, and A=Cl, $BF_4$; X=Cl, $R_1$=allyl, and A=I; X=Cl, $R_1$=octadecyl, and A=$ClO_4$; and X=Cl, R, $R_1$=—$(CH_2)_2COOH$, and A=$BF_4$.

Formula 8:

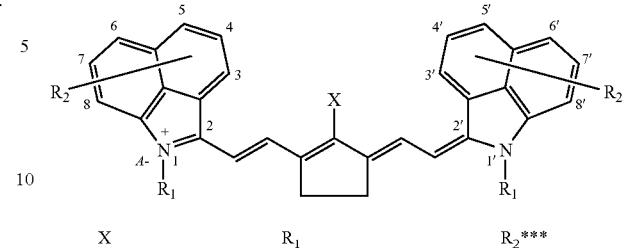

| X | $R_1$ | $R_2$*** |
|---|---|---|
| Cl, Br | Methyl | H, EDG, EWG |
| Cl, Br | Ethyl | H, EDG, EWG |
| Cl, Br | Propyl | H, EDG, EWG |
| Cl, Br | Butyl* | H, EDG, EWG |
| Cl, Br | Pentyl* | H, EDG, EWG |
| Cl, Br | Hexyl* | H, EDG, EWG |
| Cl, Br | Heptyl* | H, EDG, EWG |
| Cl, Br | Octyl* | H, EDG, EWG |
| Cl, Br | Nonyl* | H, EDG, EWG |
| Cl, Br | Decyl* | H, EDG, EWG |
| Cl, Br | Undecyl* | H, EDG, EWG |
| Cl, Br | Dodecyl* | H, EDG, EWG |
| Cl, Br | Tridecyl* | H, EDG, EWG |
| Cl, Br | Tetradecyl* | H, EDG, EWG |
| Cl, Br | Pentadecyl* | H, EDG, EWG |
| Cl, Br | Hexadecyl* | H, EDG, EWG |
| Cl, Br | Heptadecyl* | H, EDG, EWG |
| Cl, Br | Octadecyl* | H, EDG, EWG |
| Cl, Br | Phenyl** | H, EDG, EWG |
| Cl, Br | Benzyl** | H, EDG, EWG |
| Cl, Br | Naphthyl** | H, EDG, EWG |
| Cl, Br | $CH_2-SO_3^-$ | H, EDG, EWG |
| Cl, Br | $(CH_2)_2-SO_3^-$ | H, EDG, EWG |
| Cl, Br | $(CH_2)_3-SO_3^-$ | H, EDG, EWG |
| Cl, Br | $(CH_2)_4-SO_3^-$ | H, EDG, EWG |
| Cl, Br | $(CH_2)_5-SO_3^-$ | H, EDG, EWG |
| Cl, Br | $(CH_2)_6-SO_3^-$ | H, EDG, EWG |
| Cl, Br | $(CH_2)_7-SO_3^-$ | H, EDG, EWG |
| Cl, Br | $(CH_2)_8-SO_3^-$ | H, EDG, EWG |
| Cl, Br | $(CH_2)_9-SO_3^-$ | H, EDG, EWG |
| Cl, Br | $(CH_2)_{10}-SO_3^-$ | H, EDG, EWG |
| Cl, Br | $(CH_2)_{11}-SO_3^-$ | H, EDG, EWG |
| Cl, Br | $(CH_2)_{12}-SO_3^-$ | H, EDG, EWG |
| Cl, Br | $(CH_2)_{13}-SO_3^-$ | H, EDG, EWG |
| Cl, Br | $(CH_2)_{14}-SO_3^-$ | H, EDG, EWG |
| Cl, Br | $(CH_2)_{15}-SO_3^-$ | H, EDG, EWG |
| Cl, Br | $(CH_2)_{16}-SO_3^-$ | H, EDG, EWG |
| Cl, Br | $(CH_2)_{17}-SO_3^-$ | H, EDG, EWG |
| Cl, Br | $(CH_2)_{18}-SO_3^-$ | H, EDG, EWG |
| Cl, Br | $CH_2-CO_2^-$ | H, EDG, EWG |
| Cl, Br | $(CH_2)_2-CO_2^-$ | H, EDG, EWG |
| Cl, Br | $(CH_2)_3-CO_2^-$ | H, EDG, EWG |
| Cl, Br | $(CH_2)_4-CO_2^-$ | H, EDG, EWG |
| Cl, Br | $(CH_2)_5-CO_2^-$ | H, EDG, EWG |
| Cl, Br | $(CH_2)_6-CO_2^-$ | H, EDG, EWG |
| Cl, Br | $(CH_2)_7-CO_2^-$ | H, EDG, EWG |
| Cl, Br | $(CH_2)_8-CO_2^-$ | H, EDG, EWG |
| Cl, Br | $(CH_2)_9-CO_2^-$ | H, EDG, EWG |
| Cl, Br | $(CH_2)_{10}-CO_2^-$ | H, EDG, EWG |
| Cl, Br | $(CH_2)_{11}-CO_2^-$ | H, EDG, EWG |
| Cl, Br | $(CH_2)_{12}-CO_2^-$ | H, EDG, EWG |
| Cl, Br | $(CH_2)_{13}-CO_2^-$ | H, EDG, EWG |
| Cl, Br | $(CH_2)_{14}-CO_2^-$ | H, EDG, EWG |
| Cl, Br | $(CH_2)_{15}-CO_2^-$ | H, EDG, EWG |
| Cl, Br | $(CH_2)_{16}-CO_2^-$ | H, EDG, EWG |
| Cl, Br | $(CH_2)_{17}-CO_2^-$ | H, EDG, EWG |
| Cl, Br | $(CH_2)_{18}-CO_2^-$ | H, EDG, EWG |
| Cl, Br | $CH_2-NH_2$ | H, EDG, EWG |
| Cl, Br | $(CH_2)_2-NH_2$ | H, EDG, EWG |
| Cl, Br | $(CH_2)_3-NH_2$ | H, EDG, EWG |
| Cl, Br | $(CH_2)_4-NH_2$ | H, EDG, EWG |
| Cl, Br | $(CH_2)_5-NH_2$ | H, EDG, EWG |
| Cl, Br | $(CH_2)_6-NH_2$ | H, EDG, EWG |
| Cl, Br | $(CH_2)_7-NH_2$ | H, EDG, EWG |
| Cl, Br | $(CH_2)_8-NH_2$ | H, EDG, EWG |
| Cl, Br | $(CH_2)_9-NH_2$ | H, EDG, EWG |

Formula 8:

| X | $R_1$ | $R_2$*** |
|---|---|---|
| Cl, Br | $(CH_2)_{10}$—$NH_2$ | H, EDG, EWG |
| Cl, Br | $(CH_2)_{11}$—$NH_2$ | H, EDG, EWG |
| Cl, Br | $(CH_2)_{12}$—$NH_2$ | H, EDG, EWG |
| Cl, Br | $(CH_2)_{13}$—$NH_2$ | H, EDG, EWG |
| Cl, Br | $(CH_2)_{14}$—$NH_2$ | H, EDG, EWG |
| Cl, Br | $(CH_2)_{15}$—$NH_2$ | H, EDG, EWG |
| Cl, Br | $(CH_2)_{16}$—$NH_2$ | H, EDG, EWG |
| Cl, Br | $(CH_2)_{17}$—$NH_2$ | H, EDG, EWG |
| Cl, Br | $(CH_2)_{18}$—$NH_2$ | H, EDG, EWG |

*Each alkyl chain is optionally branched with an alkyl chain, cycloalkyl, aryl ring, heterocycle, aralkyl group, or unsaturation at any position on the chain.
**The phenyl, benzyl, or napthyl ring is optionally ortho-, meta-, or para-substituted with 1-3 substituents selected from halo, alkoxy, hydroxyl, $CF_3$, $NO_2$, $NH_2$, NHR, or $NR_2$.
***The $R_2$ group is H, any electron withdrawing group, or any electron donating group.

The A group is I, Cl, Br, $OSO_2R$, $BF_4$, $ClO_4$, or any pharmaceutically acceptable anion.

In one embodiment of compounds of Formula 8, X=Cl, $R_1$=Et, $R_2$=H or SPh, and A=Cl. In one embodiment, when compounds of Formula 8 are claimed, the compounds are not included where: X=Cl, $R_1$=Et, $R_2$=H or SPh, and A=Cl.

EXAMPLES

All reagents were obtained from Aldrich. Melting points (open Pyrex capillary) were measured on a Thomas Hoover apparatus and are uncorrected. $^1$H NMR and $^{13}$C NMR spectra were recorded on either Bruker Avance (400 MHz) or a Varian Unity+300 (300 MHz) spectrometer in DMSO-$d_6$ and tetramethylsilane (TMS) as an internal standard. Vis/NIR absorption spectra were recorded on a Perkin Elmer Lambda 20 spectrophotometer. High resolution mass spectra (HRMS) were recorded on a VG Analytical 70-SE spectrometer.

Example 1

The synthesis of compound 8 is shown in Scheme 1.

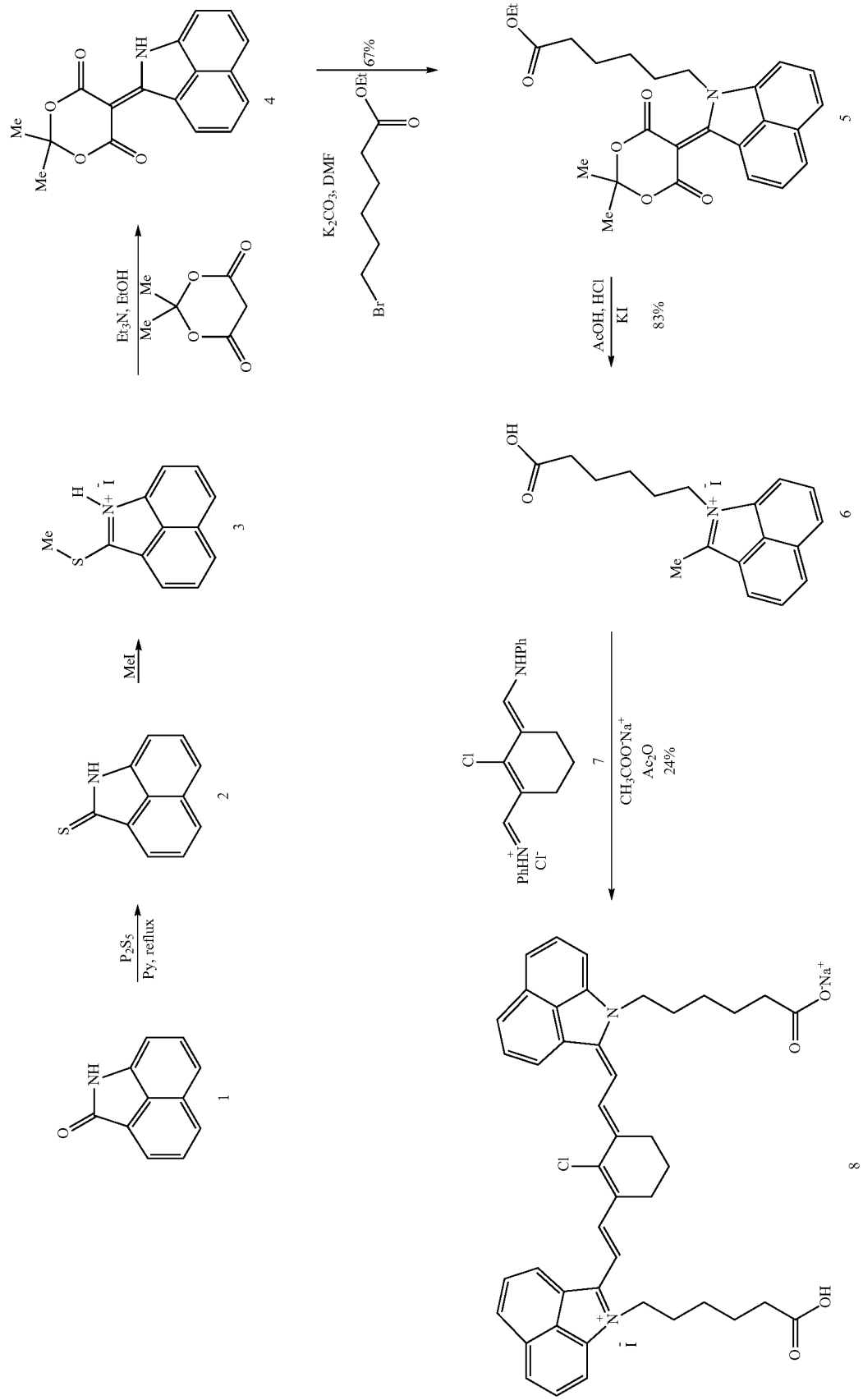

Benz[c,d]indole-2(1H)-thione (2). This compound was obtained in an 93% yield; mp 146-148° C.; (reported: yield 82%, mp 156 dec).[2,3]

2-Methylthiobenz[c,d]indole hydroiodide (3). This compound was prepared by using the reported procedures.[2,4] Since the product was unstable, it used in the next step without further purification.

2-(2,2-Dimethyl-4,6-dioxo-1,3-dioxane-5-yliden)1Hbenz[c,d]indole (4). This compound was obtained in an 85% yield; mp 220° C. (dec.); (reported: yield 94%, mp 223° C.).[1,2]

Ethyl 2-(2,2-dimethyl-4,6-dioxo-1,3-dioxan-5-ylidene)-1H-benz[c,d]indole-1-hexanoate (5). A mixture of compound 4 (3 g, 10.2 mmol), ethyl 6-bromohexanoate (5.5 g, 30.6 mmol) and $K_2CO_3$ (4.2 g, 30.60 mmol) were heated in DMF (40 mL) at 90° C. for 18 hr under a nitrogen.atmosphere. The mixture was cooled to room temperature and filtered. The filtrate was concentrated under reduced pressure. The residue was purified on silica gel (flash chromatography, EtOAc-hexanes, 1:2) providing 3 g (6.86 mmol, 67%) of 5 as a red solid; mp 142-143° C.; $^1$H NMR δ 1.11 (t, J=8.0 Hz, 3H), 1.20-1.30 (m, 2H), 1.40-1.53 (m, 2H), 1.74 (s, 6H), 1.79-1.87 (m, 2H), 2.22 (t, J=8.3 Hz, 2H), 3.97 (q, J=8.0 Hz 2H), 4.34 (t, J=8.3 Hz, 2H), 7.77 (t, J=8.3 Hz, 1H), 7.73 (t, J=8.7 Hz, 1H), 7.99-8.06 (m, 2H), 8.43 (d, J=8.7 Hz, 1H), 8.90 (d, J=8.0 Hz, 1H); $^{13}$C NMR δ 14.51, 24.40, 26.14, 26.82, 28.49, 33.67, 48.82, 60.10, 81.66, 102.44, 115.32, 123.82, 126.54, 129.12, 129.34, 130.35, 131.54, 134.73, 134.80, 140.38, 162.40, 165.12, 173.07; MALDI-MS m/z 438 ([M$^+$+1], 100); ESI-HRMS calcd for $C_{25}H_{28}NO_6$ (M$^+$+1) 438.1917, found 438.1921.

1-(5-Carboxypentyl)-2-methylbenz[c,d]Indolium Iodide (6)

Ester 5 (1 g, 2.9 mmol) was dissolved in acetic acid (4 mL) and the mixture was refluxed for 20 min. Concentrated HCl (4 mL) was added dropwise to the refluxing mixture until the color changed from red to green. The mixture was cooled to room temperature, and saturated KI solution was added until the product started to precipitate. The product was filtered off, washed with ether, and dried in vacuo affording 1 g (2.4 mmol, 83%); mp 218° C. (dec.); $^1$H NMR δ 1.34-1.59 (m, 4H), 1.89-1.96 (m, 2H), 2.22 (t, J=8.0 Hz, 2H), 3.25 (s, 3H), 4.67 (t, J=8.0 Hz, 2H), 8.02 (t, J=8.7 Hz, 1H), 8.18 (t, J=8.3 Hz, 1H), 8.46 (d, J=8.7 Hz, 1H), 8.56 (d, J=8.0 Hz, 1H), 8.82 (d, J=8.7 Hz, 1H), 8.98 (d, J=8.0 Hz, 1H); $^{13}$C NMR δ 15.03, 24.49, 26.14, 29.51, 33.91, 47.29, 115.12, 121.69, 122.41, 128.62, 129.61, 130.20, 131.38, 135.73, 138.92, 139.10, 173.07, 174.93; MALDI-MS m/z 282 ([M$^+$-I], 100); ESI-HRMS calcd for $C_{18}H_{20}NO_2$ (M$^+$-I) 282.1494, found 282.1497.

A solution of salt 6 (500 mg, 1.22 mmol), Vilsmeier-Haack reagent 7[5] (220 mg, 0.61 mmol) and anhydrous sodium acetate (200 mg, 2.44 mmol) in acetic anhydride (15 mL) was heated to 70° C. for 1 h under a nitrogen atmosphere. The reaction progress was monitored by Vis/NIR spectroscopy. The green solution was cooled to room temperature, then poured into saturated solution of sodium iodide. The crude product was filtered off, washed with ether and recrystallized from methanol/ether providing 240 mg (0.29 mmol, 24%); mp 145-147° C.; $^1$H NMR δ 1.42 (m, 6H), 1.57 (m, 6H), 1.75 (m, 4H), 2.19-2.21 (m, 6H), 2.84 (m, 2H), 4.26 (m, 2H), 6.74 (d, J=7.7 Hz, 2H), 7.51-7.57 (m, 4H), 7.64-7.67 (m, 2H), 7.89 (t, J=8.3 Hz, 2H), 8.16 (d, J=8.3 Hz, 2H), 8.28 (d, J=7.7 Hz, 2H), 8.56 (d, J=7.7 Hz, 2H), 12.0 (bs, 2H-exchangeable with $D_2O$); MALDI-MS m/z 699 ([M$^+$-I], 100); ESI-HRMS calcd for $C_{44}H_{44}N_2O_4Cl$ (M$^+$-I) 699.2990, found 699.2972; Vis/NIR $\lambda_{max}$=1013 nm ($\varepsilon$=1.2×10$^5$ Cm$^{-1}$ M$^{-1}$, methanol).

Example 2

Preparation of MHI-148 (Compound 10)

As shown in Scheme 2, a solution of salt 9 (1.00 g, 2.82 mmol), Vilsmeier-Haack reagent 7[5] (507 mg, 1.4 mmol) and anhydrous sodium acetate (925 mg, 11.28 mmol) in acetic anhydride (30 mL) was heated to 70° C. for 1 h under a nitrogen atmosphere. The reaction progress was monitored by Vis/NIR spectroscopy. The green solution was cooled to room temperature, then poured into saturated solution of sodium iodide. The crude product was filtered off, washed with ether and recrystallized from methanol/ether providing 0.8 g (1.0 mmol, 71%); $^1$H NMR, δ 1.42 (m, 6H), 1.57 (m, 6H), 1.75 (m, 4H), 2.19-2.21 (m, 6H), 2.84 (m, 2H), 4.26 (m, 2H) 6.30-6.37 (m, 2H), 7.28-7.32 (m, 4H), 7.40-7.51 (m, 4H), 7.64 (m, 2H), 8.28 (d, J=8.3 Hz, 2H), ESI-MS m/z 742 ([M$^+$], 100); ESI-HRMS calcd for $C_{42}H_{52}N_2O_4Cl$ (M$^+$-$CH_3COO^-$) 683.3616, found 683.3608. $\lambda_{max}$ Abs=780 nm and $\lambda_{max}$ FL=800 nm.

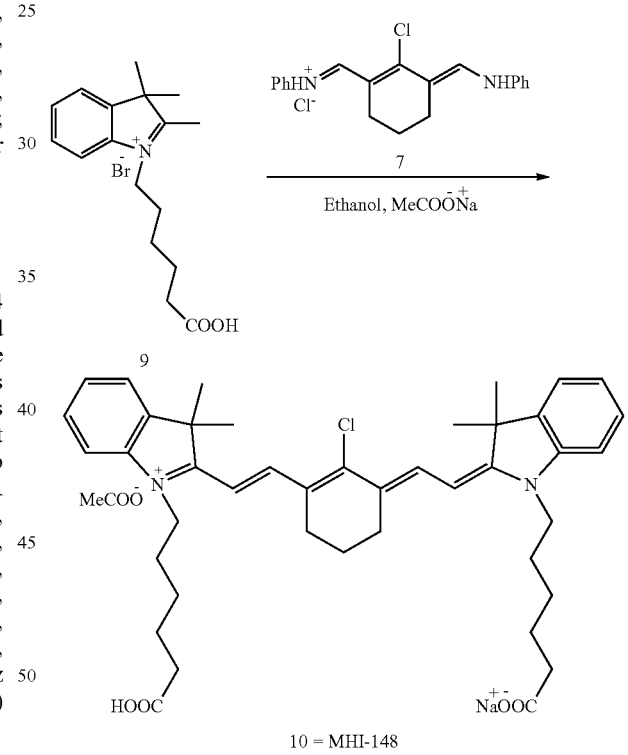

10 = MHI-148

Synthesis of cyclopentene ring-containing structures can be carried out using methods known in the art (see Nagao, et al., Dyes and Pigments, 2007, 73, 344-352, for example) and modifications provided here.

Example 3

Evaluation of Organic Cyanine-Containing Compounds as Imaging Agents

FIG. 1 shows imaging of human cancer cells including prostate (LNCaP, ARCaP$_E$, ARCaP$_M$, C4-2, PC-3), liver (HepG2), osteosarcoma (MG63), breast (MCF-7), kidney (RCC), bladder (T-24), cervical (HeLa), leukemia (K562)

and lung (H358) with MHI-148. Cancer cells show a significant uptake of MHI-148 (dark color), while corresponding normal human or mouse cells (e.g. normal prostate fibroblasts, NPE; marrow stromal cells, BMC; normal vascular endothelial cells, VEC; or mouse macrophage RAW cells) failed to yield any time- or concentration-dependent uptake of MHI-148 in culture. Normal epithelial cells (e.g. normal prostate epithelial cells, NPE and normal human skin epithelial cells, HaCaT) showed a low uptake of MHI-148. All the cells were cultured with 100 µM MHI-148 in basal media (T-medium with 5% fetal bovine serum and 1% antibiotics) for two hours and were imaged under an inverted microscope. These conditions are the usual conditions used here unless otherwise specified.

Figures 1, 2:
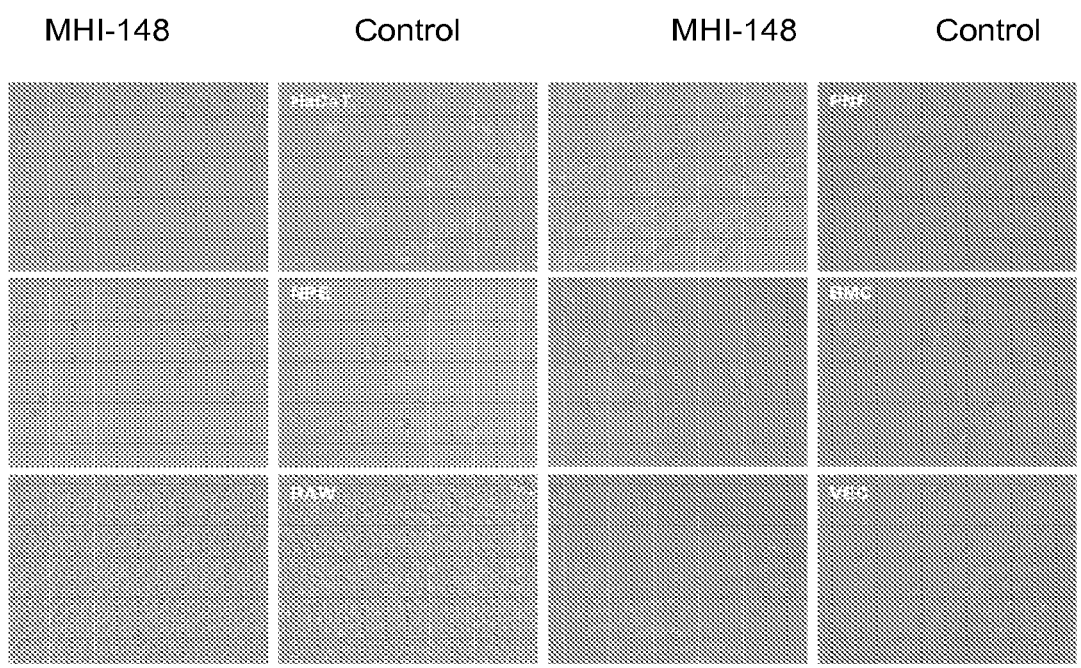
Figure 2:
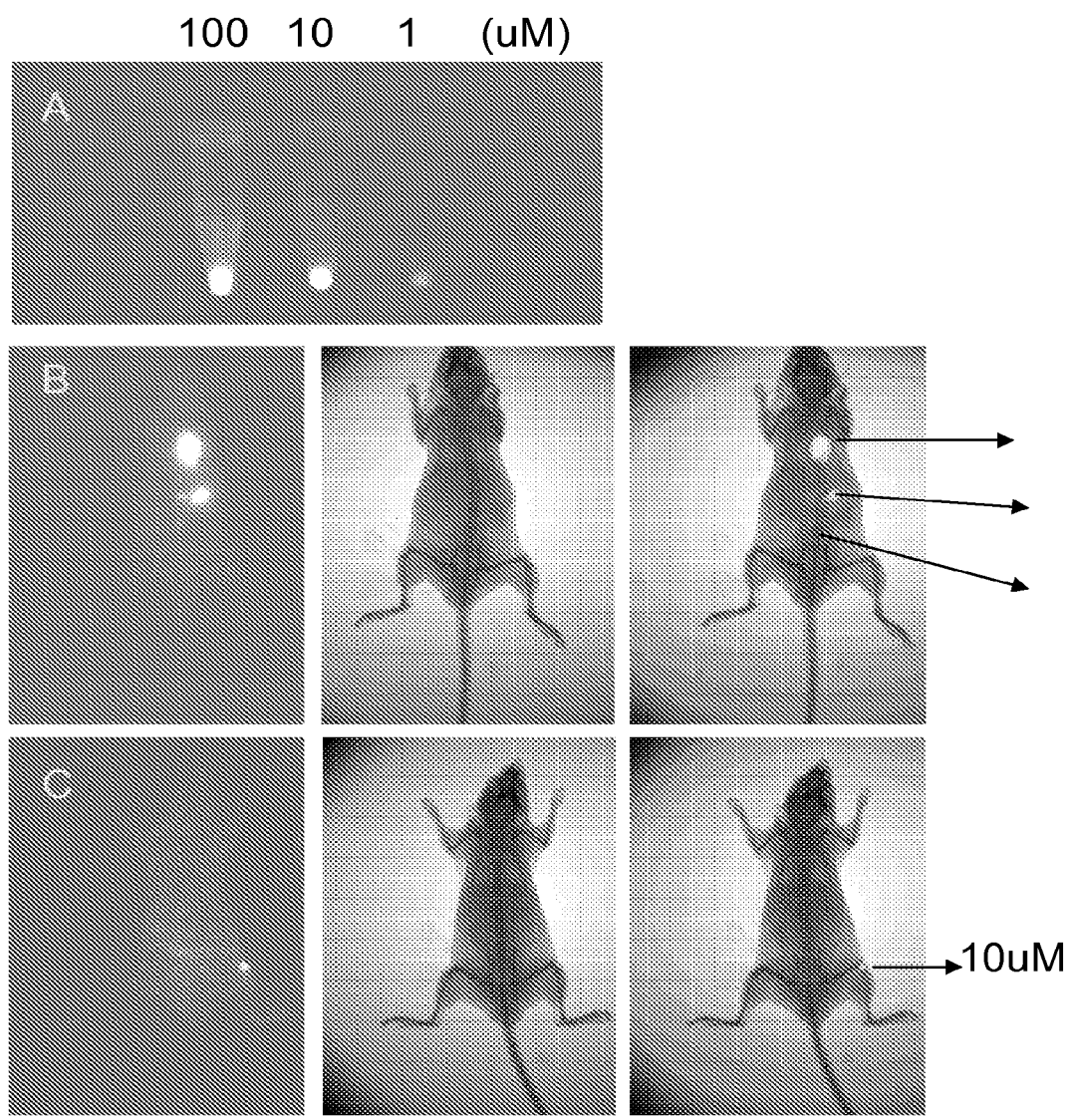

FIG. 2(A) shows human ARCaP$_M$ prostate cancer cells incubated with 100 uM, 10 uM and 1 uM concentrations of MHI-148, respectively. After incubation for 2 hours, cells were washed 3 times with PBS, harvested by centrifuge and imaged. One million of the MHI-148 tagged ARCaP$_M$ cells with different concentrations were injected subcutaneously in the back of the mouse and imaged at the same time (B). One million of the MHI-148 tagged ARCaP$_M$ cells with concentration of 10 uM were also injected directly into mouse tibia and can be seen in the intratibial space (C). All the in vitro and in vivo imaging was performed using a Kodak multimodal-imaging system IS2000MM (Kodak) equipped with an excitation bandpass filter at 720 nm and an emission at 850 nm. Exposure time was 30 s per image. The images were analyzed using the imaging station IS2000MM software (Kodak 1D Image Analysis Software; Kodak). At all concentration ranges (1, 10 and 100 µM), intense images can be readily detected in test tubes of MHI-148 tagged ARCaP$_M$ cells (FIG. 2, top panel).

Figure 3:
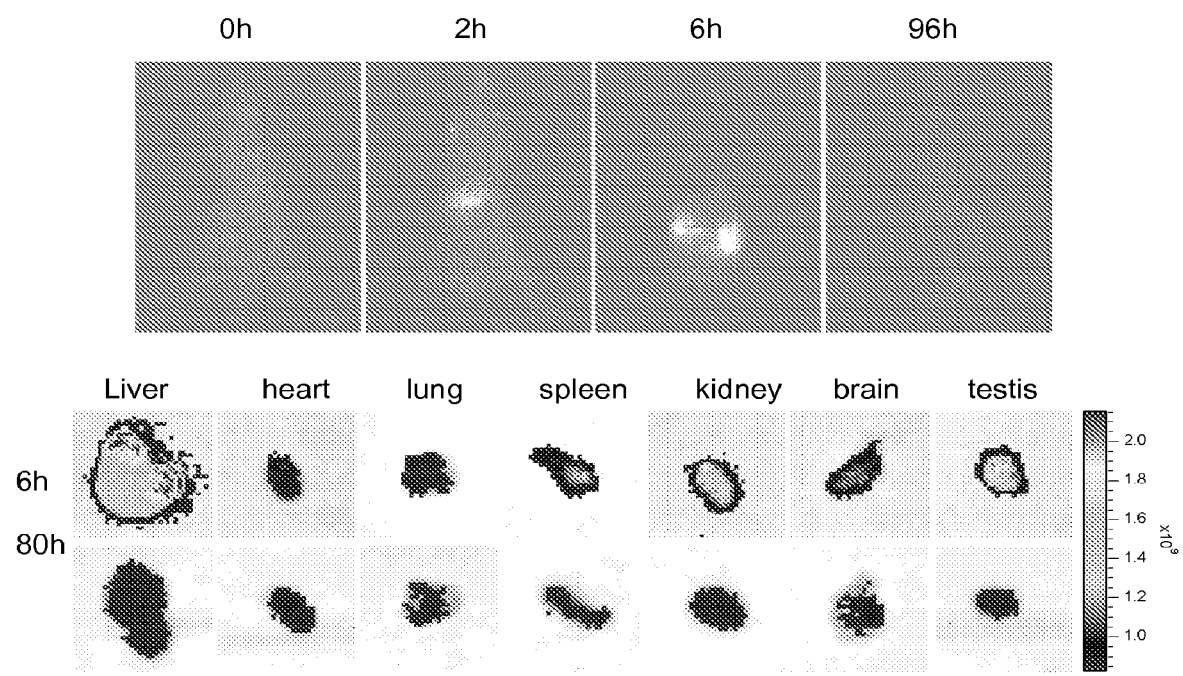
FIG. 3 shows ex vivo imaging of organs that were excised from normal mice treated with MHI-148.

FIG. 3 shows ex vivo imaging of organs excised from normal mice treated with MHI-148. MHI-148 (5 nmol) was given by tail vein injection and the MHI-148 distribution followed at 2, 6, and 96 hrs. At the end of this study, mice were sacrificed at 6 or 80 hrs after MHI-148 tail vein administration. MHI-148 uptake by the liver and kidney can be detected at 2 and 6 hrs after tail vein administration of MHI-148. By 96 hrs, no detectable MHI-148 can be found in live mice and dissected mouse tissues. The isolated tissues and organs excised from mice at 6 hours and 80 hours after receiving 5 nmol MHI-148 were also imaged by the Xenogen machine and the signals were compared by fluorescence intensity. As shown in the bottom panel of FIG. 3, the isolated mouse tissues imaged by a Xenogen machine agreed with the images acquired in mice liver, kidney and testis, which were shown to be positive at 6 hrs post MHI-148 administration but were void of any fluorescence signaling when examined at 80 hrs post MHI-148 administration.

Figure 4:
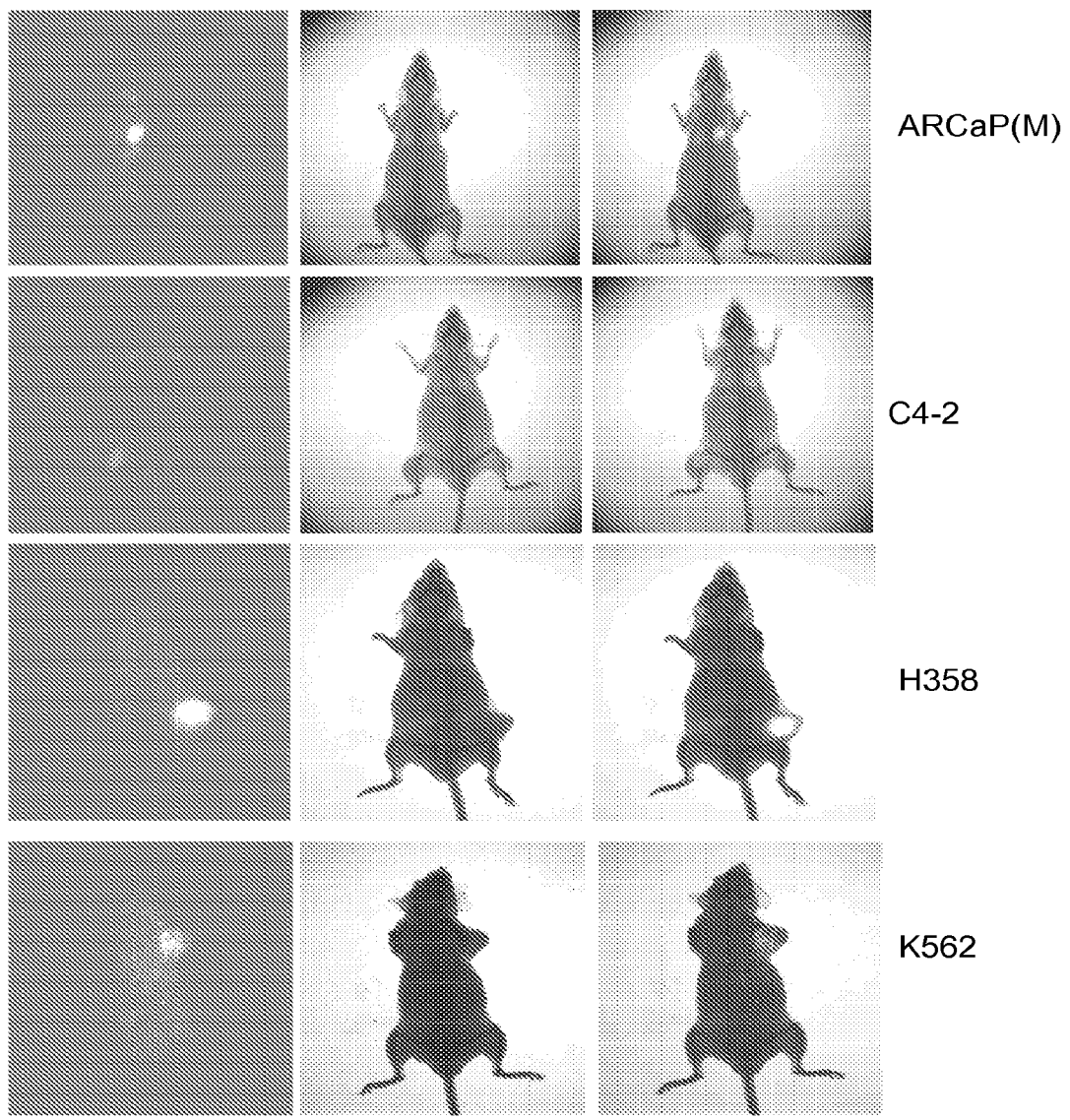
FIG. 4 shows the in vivo imaging of subcutaneous prostate ARCaP$_M$ and intratibial C4-2 tumors in live mice using MHI-148. In addition, MHI-148 also can image human lung cancer (H358) and lymphoma (K562).

FIG. 4 shows imaging of pre-established subcutaneous tumors in live mice. Subcutaneous ARCaP$_M$ and intratibial C4-2 tumors were established in live mice prior to the administration of MHI-148. The tumors measured about 0.5-1.0 cm in diameter at the time of imaging. 10 nmol of MHI-148 was given to mice through tail vein and imaged using Kodak multimodal-imaging system. Human lung (H358) and leukemia (K562) cancer cells were injected subcutaneously into one side of the shoulder of mice. When the tumors were about 1-2 cm in diameter, 10 nmol MHI-148 was given through tail vein and tumor images were taken at 96 hrs after MHI-148 administration. Clear tumor associated images are seen.

Figure 5:
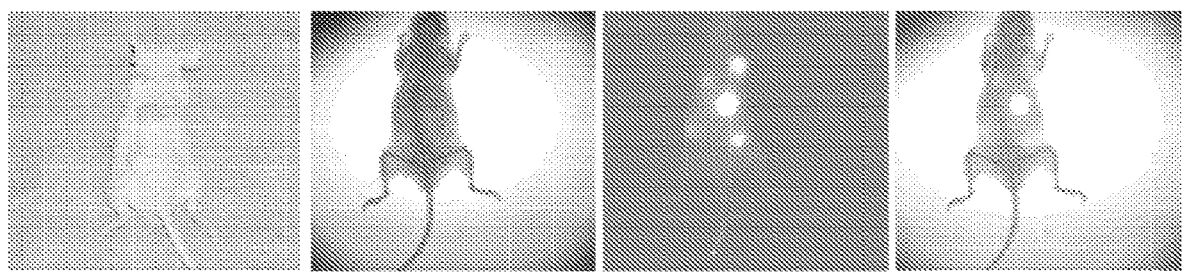
FIG. 5 shows the ability to detect multiple tumors of different sizes in one mouse following in vivo administration of MHI-148.

As shown in FIG. 5, MHI-148 can be used to detect multiple tumors in one mouse following in vivo administration of MHI-148. A mouse had 5 pre-established human ARCaP$_E$, ARCaP$_M$, and C4-2 tumors in the back by subcutaneous injection of tumor cells. Four tumors were measured with 0.2-1.0 cm in diameter and one tumor was not detectable by visualization at the time of NHI-148 administration. All five tumors were imaged at 96 hrs after 10 nmol MHI-148 was given through the tail vein. Visual and palpation techniques could only detect four tumors, while MHI-148 (10 nmol), after tail vein administration, clearly gained access to all tumors in the live mouse and allowed tumor images to be detected in all five tumors. One of the smallest of these tumors with a diameter of <2 mm$^3$ (see arrow) could be imaged only by MHI-148 and was difficult to visualize or palpate without prior knowledge of where the tumor was located.

Figure 6:
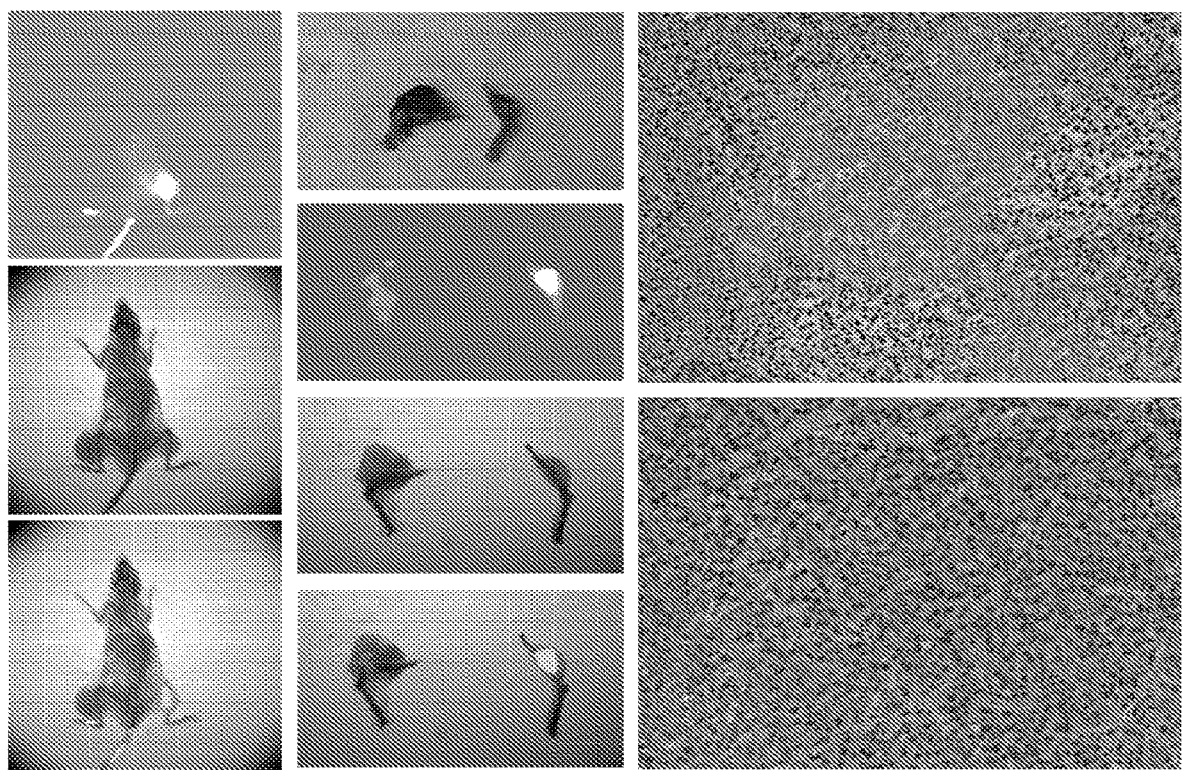
FIG. 6 shows the ability to identify necrotic areas which gave no signal within active tumors (positive signal) through imaging with MHI-148.

FIG. 6 shows the ability to identify necrotic areas within tumors through imaging with MHI-148. C4-2 cells were injected into both sides of tibia of one mouse. When one tumor was developed to size with visible necrosis and the other tumor still in the fast growing phase, 10 nmol MHI-148 was given through tail vein. After 48 hrs, the mouse was imaged. As shown, the live C4-2 tumor at the right tibia of the mouse was shown to uptake MHI-148, while necrotic or dead tumor cells shown on the left side of the mouse failed to uptake MHI-148. The histopathology of the tumors was confirmed by the H/E stain (see upper right panel).

Figure 7:
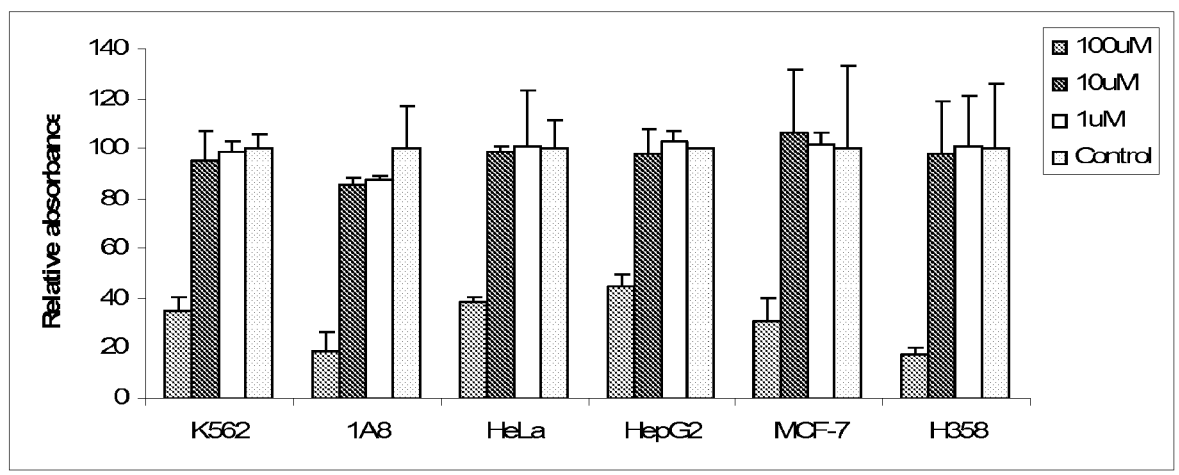
FIG. 7 graphically illustrates the inhibition of cancer growth in vitro following treatment with MHI-148.

FIG. 7 illustrates the inhibition of cancer growth in vitro following treatment with MHI-148. Cancer cell were plated in 96-well plates in T-medium containing 5% FBS with different concentrations of MHI-148 for 48 hrs of incubation. Cell numbers were measured using CellTiter 96 Aqueous One Solution Cell Proliferation Assay (Promega, Madison, Wis.).

Figure 8:
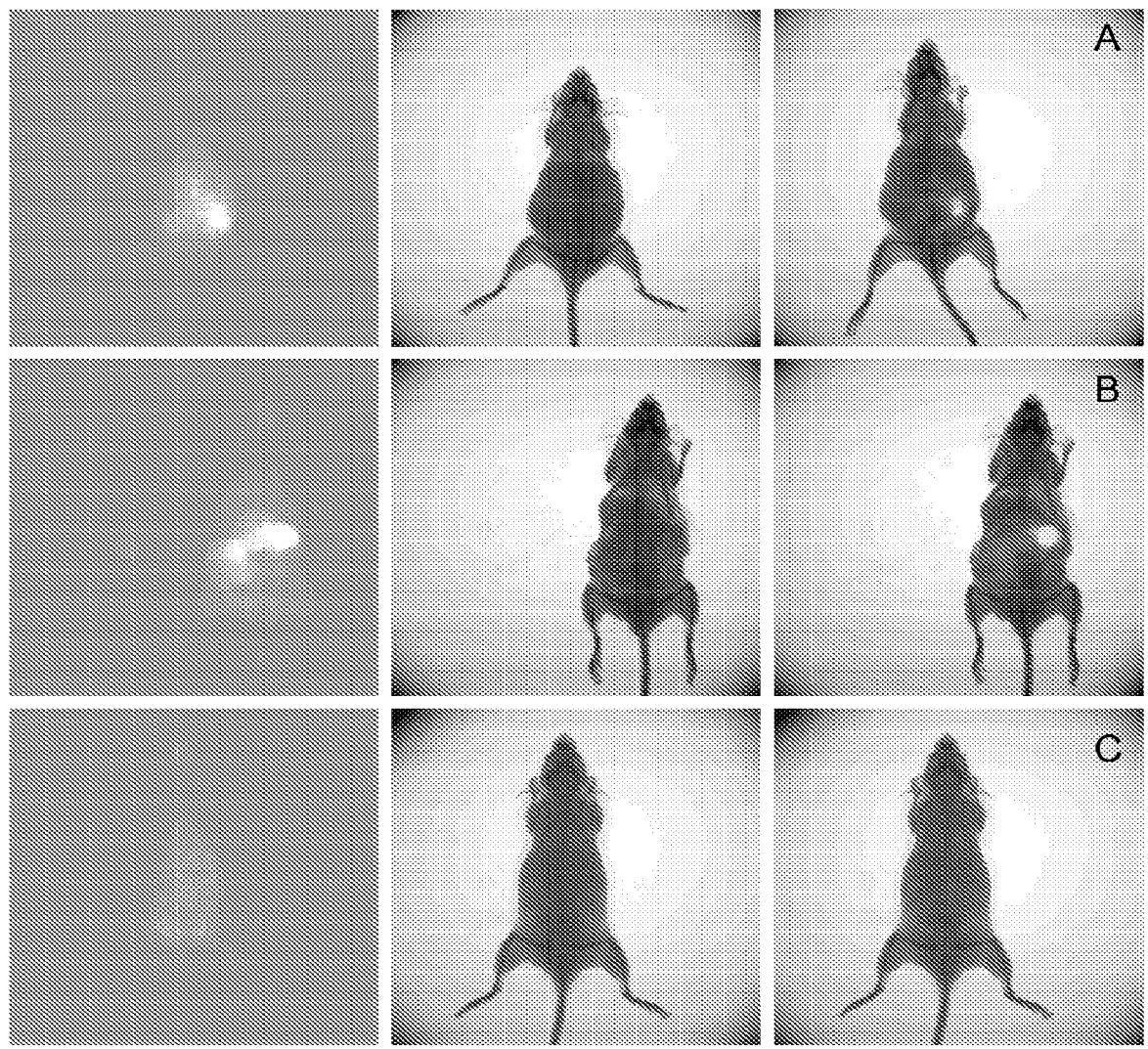
FIG. 8 shows the ability to detect spontaneous tumor development using MHI-148 in mice predisposed to develop prostate tumors.

FIG. 8 shows the ability to detect spontaneous tumor development using MHI-148 in mice predisposed to develop prostate tumors. 10 nmol of MHI-148 was given to a 46 week-old TRAMP transgenic mouse with spontaneously developed prostate tumor mass and imaged after 4 hrs after MHI-148 injection (panel A). The tumor mass was exposed and confirmed of prostate origin and showed clear tumor in situ (panel B). This study was repeated in a young age TRAMP mouse which harbored no tumor and no signal was detected. Surgical dissection of this mouse confirmed no solid tumor mass was present (panel C).

Similar data was obtained using MHI-78 (data not shown).

MHI-148 can be used effectively for imaging a broad spectrum of human tumor cells and solid tumors in live mice. Although MHI-148 can be taken by some normal mouse tissues, such as liver, kidney, testis and seminal vesicles, the compound was observed to be cleared from these organs within a 96-hr time period in live animals. Because of the attractive pharmacokinetic properties of this compound (excreted or metabolized by host mice but accumulated in tumors when examined at 96 hrs after MHI-148 administration), its near-infrared fluorescence emission with little interference from mouse hair, skin and internal organs and its high fluorescence intensity due to a large extinction coefficient of the dye and its analogs, MHI-148 and its analogs are suitable for imaging both surface (subcutaneous) and deep (intratibia) tumors. MHI-148 was also found to be relatively photostable, and can be used to image tumors approximately 2 mm$^3$ or 2 mg in size in mice.

Example 4

Evaluation of Organic Cyanine-Containing Compounds as Effectors of Cancer Cell Growth To confirm the ability of other compounds to exert cytotoxicity against the growth of human tumors in vitro and in vivo, the effect of MHI-25 on the growth of C4-2 tumors in vitro (FIG. 9 top panel) and in mice (FIG. 9 bottom panel) was studied. 100 uM of MHI-25 treatment for 24 hrs induced a significant cell death in culture, while 10 uM did not induce cell death with marked cell morphologic change (upper panel). As revealed by this study, MHI-25 exposure for 24 hrs clearly induced apoptosis when the concentration of MHI-25 was increased to 100 μM.

Figure 9:
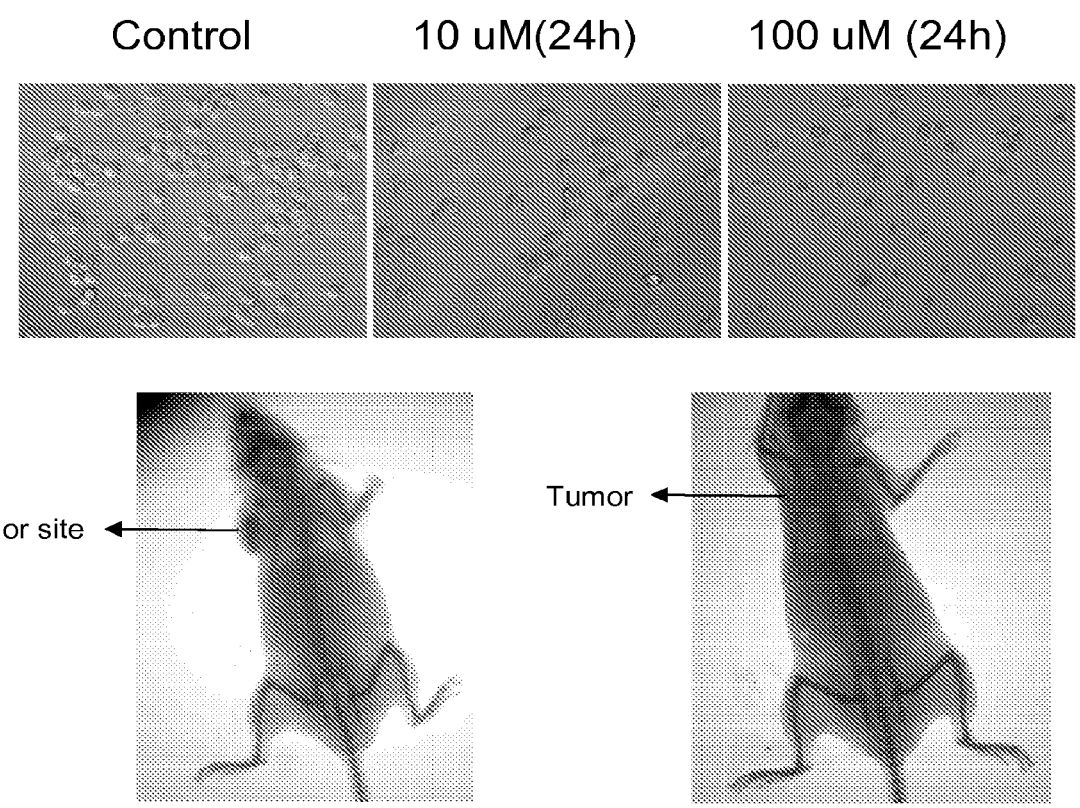
FIG. 9 shows the growth inhibitory effects of MHI-25 on the growth of C4-2 tumors in vitro and in vivo.

FIG. 9 bottom panels, shows that administration of 100 nmols of MHI-25 to mice with pre-established C4-2 tumors induced marked cell death, with tumors almost eliminated at Day 5 after MHI-25 administration.

Example 5

IR780 Studies

Figure 10:
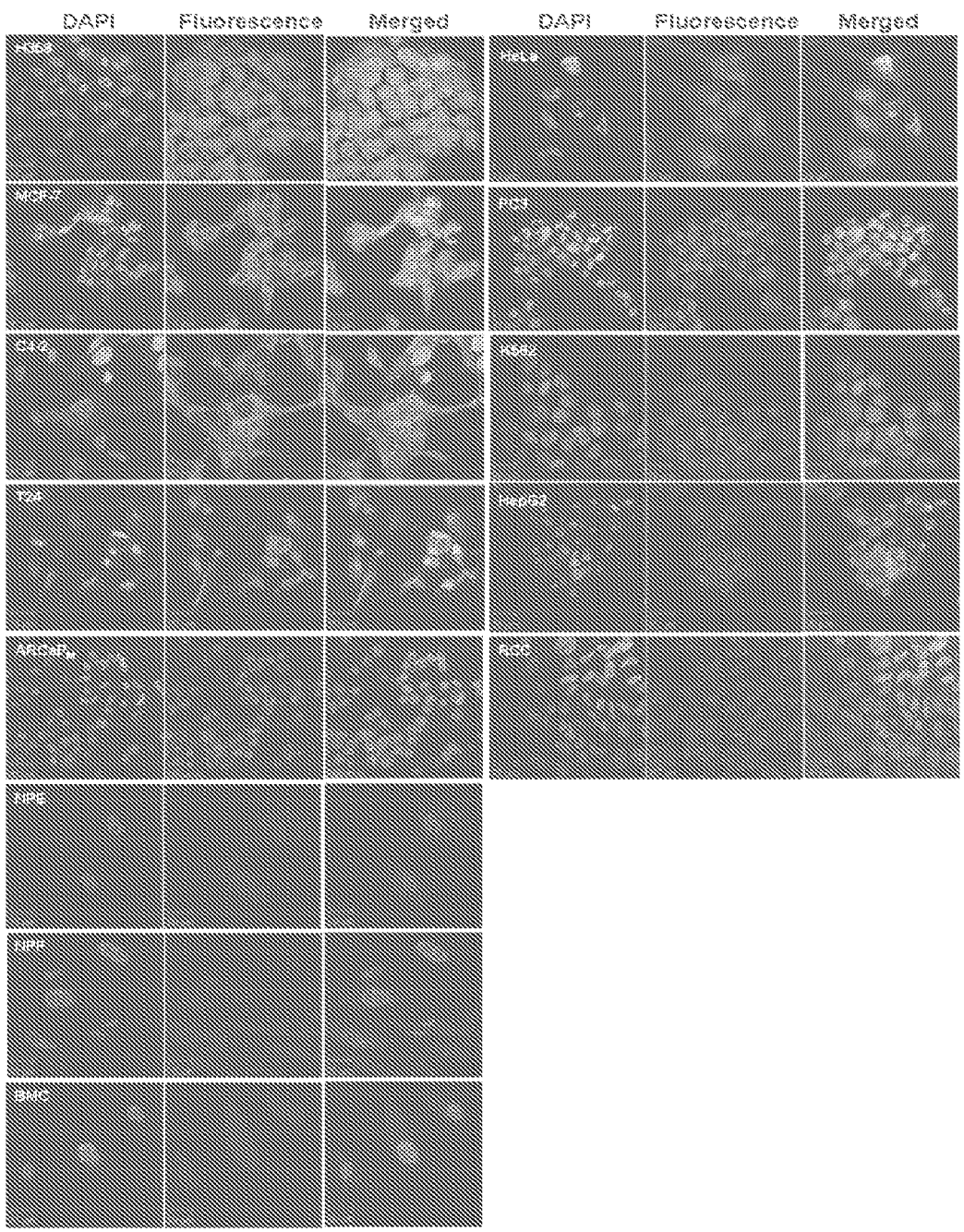
FIG. 10 shows the positive uptake of IR780 in various human cell lines.

The uptake of IR780 by human cancer cells in culture was also studied. Human cancer cells including prostate (AR-CaP$_M$, C4-2, PC-3), liver (HepG2), breast (MCF-7), kidney (RCC), bladder (T-24), cervical (HeLa), leukemia (K562) and lung (H358) cancer cells showed a significant uptake of IR-780, while normal human cells (e.g. normal prostate fibroblasts (NPF), normal prostate epithelial cells (NPE), marrow stromal cells, BMC) showed a very low uptake of this organic cyanine-containing dye in culture (see FIG. 10). All the cells were cultured with 20 uM IR-780 in basal media (T-medium with 5% fetal bovine serum and 1% antibiotics) for 30 minutes and were imaged under confocal microscope.

Figure 11:
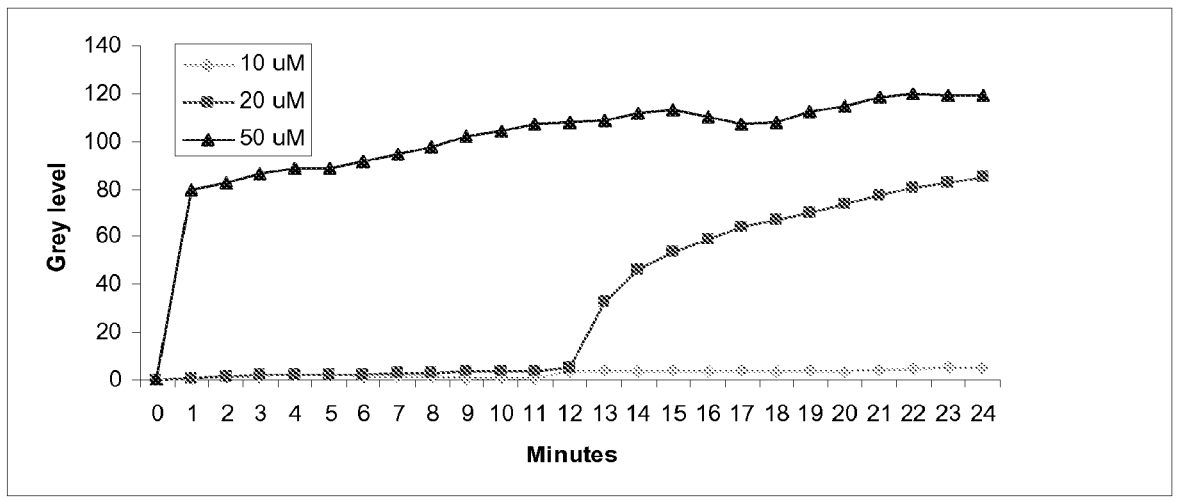
FIG. 11 shows time- and concentration-dependent uptake of IR780.

As shown in FIG. 11, ARCaP$_M$ cells show a time- and concentration-dependent uptake of IR780. In FIG. 11, ARCaP$_M$ Cells were plated on live-cell imaging chambers from World Precision Instrument (Sarasota, Fla.) overnight. Cells were treated with IR-780 with different concentrations and were imaged using a Perkin-Elmer Ultraview ERS spinning disc confocal microscope. This system was mounted on a Zeiss Axiovert 200 m inverted microscope equipped with a 37° C. stage warmer, incubator, and CO2 perfusion. A x63 or x100 Zeiss oil objective (numerical aperture, 1.4) was used for all images and a Z-stack was created using the attached piezoelectric z-stepper motor. The 633 nm laser line of an argon ion laser (set at 60% power) was used to excite the IR-780 organic dye. For each comparison, the exposure time and laser intensity was kept identical for accurate intensity measurement. Pixel intensity was quantitated using Metamorph 6.1 (Universal Imaging, Downingtown, Pa.) and the mean pixel intensity was generated as grey level using the Region Statistics feature on the software.

Normal prostate epithelial cells did not take up the dye (data not shown). The uptake of IR780 by ARCaP$_M$ cells was also blocked by BSP, an organic anion transporter inhibitor (data not shown). A normal mouse was injected with IR780 through the tail vein, and isolated tissues and organs excised from mice were cut into frozen slides and imaged under confocal microscope. All mouse tissues failed to uptake IR780. (data not shown).

Figure 12:
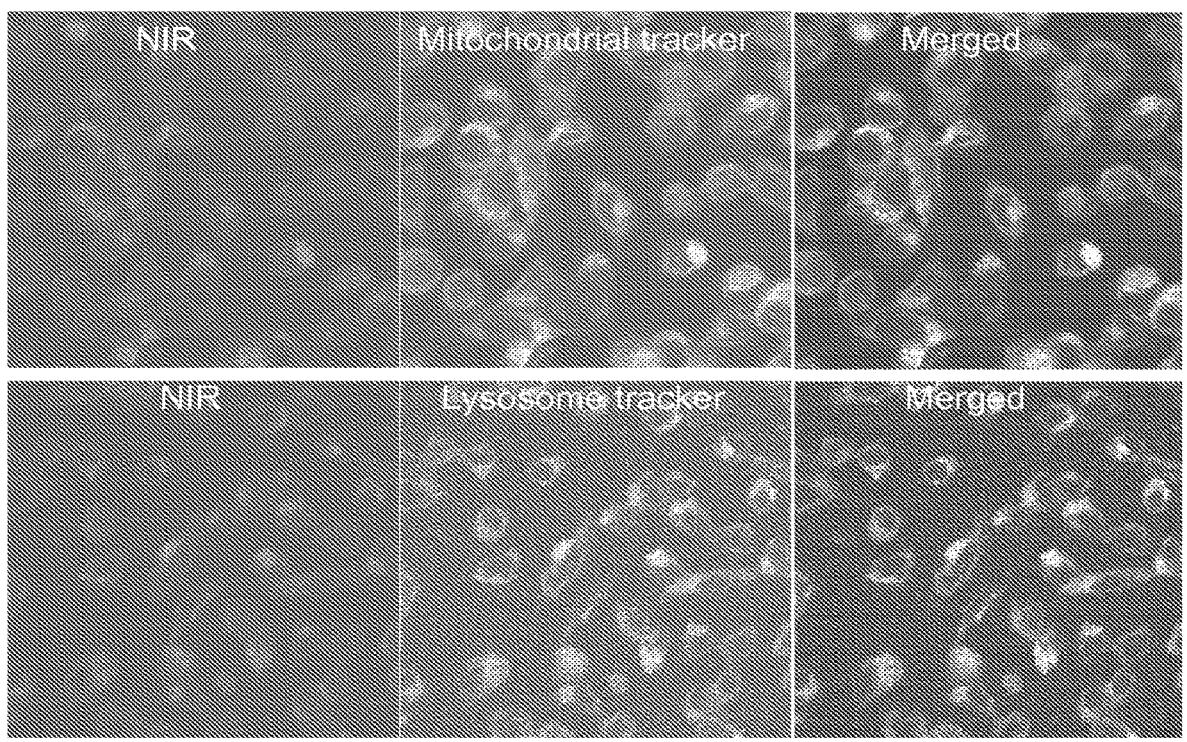
FIG. 12 shows IR780 co-localized with mitochondrial, lysomomal and cytoplasmic compartments.

As shown in FIG. 12, IR780 co-localized with mitochondrial, lysomomal and cytoplasmic compartments. FIG. 12 shows ARCaP$_M$ cells co-stained with IR780 and mitochondrial tracker or lysosome tracker and imaged under a confocal microscope.

Intratibial ARCaP$_M$ tumors were also established in live mice prior to administration of IR783. 5 nmol of IR783 was given through the tail vein and imaged using a Kodak multimodal imaging system. Clear tumor images were detected (data not shown).

Figure 13:
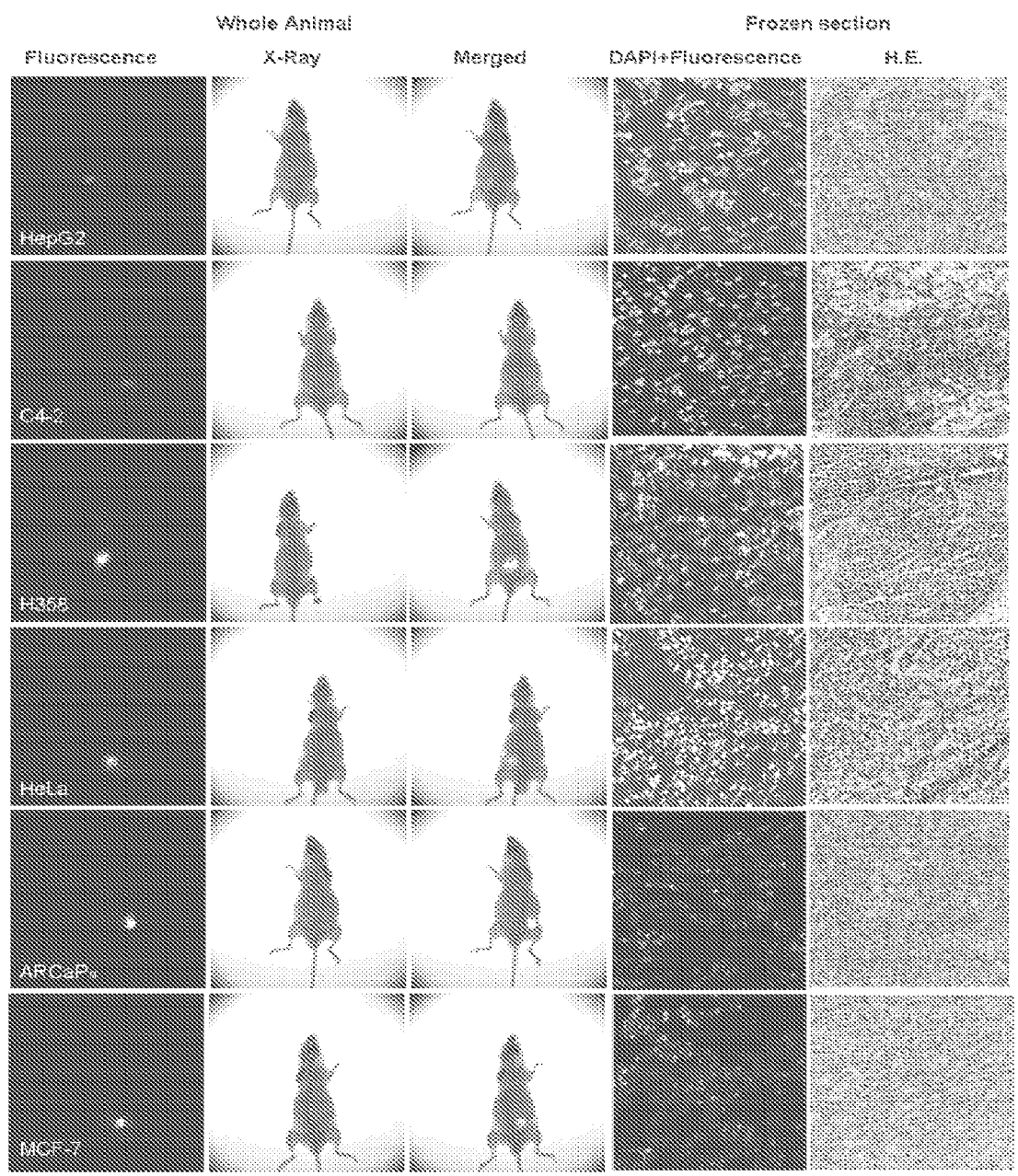
FIG. 13 shows images of subcutaneous human tumors with IR780.

As shown in FIG. 13, clear tumor images can be detected in subcutaneous tumors with little or no background autofluorescence. Subcutaneous HepG2 (human liver cancer), C4-2 (human prostate androgen-independent and metastatic cancer), H358 (human lung cancer), HeLa (human cervical cancer), MCF-7 (human breast cancer) and ARCaP$_M$ (a highly bone and soft tissue metastatic human prostate cancer) cancers were established in live mice prior to the administration of IR-780. The tumor xenografts were measured about 0.5-1.0 cm in diameter at the time of imaging. 5 n mol of IR-780 were given to mice through tail vein and imaged using Kodak multimodal-imaging system. The distribution of IR-780 in tumor tissues was conformed by imaging of frozen sections under confocal microscope. The histopathology of the tumor was confirmed by H/E staining of the frozen tissue specimens and DAPI stained cell nuclei.

Example 6

IR783 Studies

The uptake of IR783 was studied and confirmed in a variety of human cell lines as shown below:

| Cell line | Type of Cell | Uptake |
| --- | --- | --- |
| SN12C, ACHN | Renal | Strong |
| PDAC-2.3, PDAC-3.3, BTC-3, BTC-5 | Pancreatic | Strong |
| RT-4, T24, 253J, TCC | Bladder | Strong |
| HEK293 | Human embryonic kidney epithelial normal cells | Low |
| ARCaP$_M$, LNCaP, ARCaP$_E$, C4-2, PC-3 | Prostate | Strong |
| HepG2 | Liver | Strong |
| MCF-7 | Breast | Strong |
| RCC | Kidney | Strong |
| HeLa | Cervical | Strong |
| H358 | Lung | Strong |
| K562 | Leukemia | Strong |
| P69 | Human prostate epithelia | Very low or no |
| NPF | Prostate fibroblasts | Very low or no |
| HaCaT | Skin | Very low or no |
| BMC | Bone marrow stroma | Very low or no |
| VEC | Vascular endothelia | Very low or no |
| RAW | Mouse macrophages | Very low or no |

Figure 14:
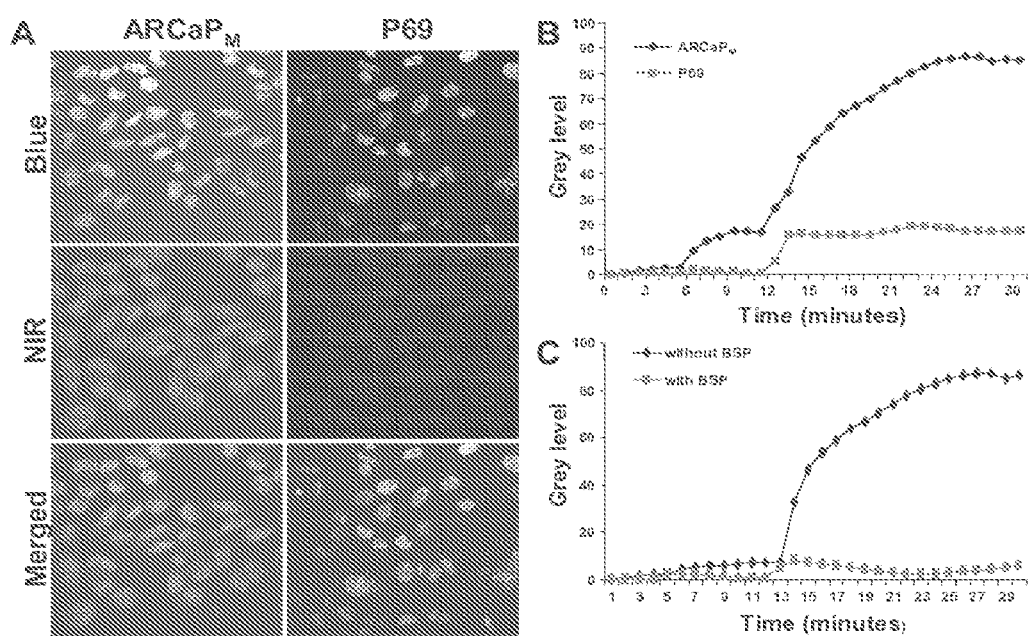
FIG. 14 shows preferential uptake of IR783 by cancerous (ARCaP$_M$) but not normal (P69) cells in culture. This uptake is completely abolished by bromosulfophthalein (BSP) (an inhibitor of organic anion transporters).

There was no uptake of the IR783 by cancer cells at 0° C., suggesting that the uptake was an active process (data not shown). By comparing the ARCaP$_M$ prostate cancer cells and the P69 normal prostate epithelial cells, IR783 uptake was determined to occur only in the cancer cells and the uptake was in a time-dependent fashion (FIG. 14), as well as in a dose-dependent fashion (data not shown). FIG. 14A shows ARCaP$_M$ prostate cancer cells incubated in 50 μM of IR783 at 37° C. for 30 min. After being washed in PBS to remove free dyes, the cells were subject to confocal fluorescence imaging. DAPI, added together with IR783, was used as a positive control for the staining of the cell nucleus. P69, representing normal human prostate epithelial cells, was stained in parallel. Images were acquired by Zeiss LSM 510 META confocal microscopy. FIG. 14B shows that IR783 was taken up only by cancer cells, and the uptake was in a time-dependent manner. FIG. 14C shows the specific uptake by ARCaP$_M$ cells was inhibited by BSP, a competitive inhibitor of the OATP transporters. 100 μM BSP was used to pre-incubate with ARCaP$_M$, before 50 μM IR783 was added.

Figure 15:
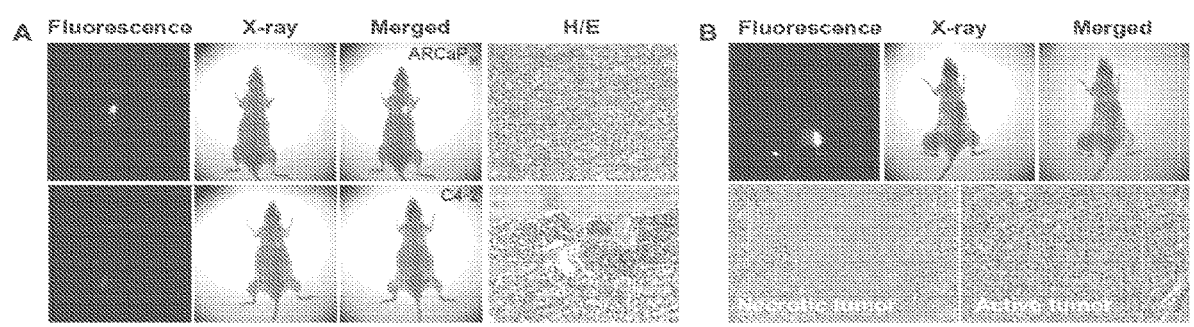
FIG. 15 shows imaging pre-established human prostate tumor xenografts grown subcutaneously and intraosseously in mice using IR783. The active tumors took the dye.

IR783 was also preferentially taken up by human prostate cancer xenografts in subcutaneous and intra-tibial sites of nude mice, and by metastatic bone lesions (FIG. 15). Metabolically active androgen-independent C4-2 tumors in mouse tibia retained the dye, whereas necrotic tumors on the contralateral side of the animal did not (FIG. 15). FIG. 15A shows a mouse bearing a subcutaneous ARCaP$_M$ tumor (top panels) and another with an intratibial C4-2 tumor (bottom panels). The mice were injected i.p with IR783 at 0.2 μg/kg. Imaging was performed 24 hours later with the Kodak multimodal-imaging system. Histopathological analysis (H/E) confirmed the presence of tumors. FIG. 15B shows a mouse with C4-2 tumors in both tibias. This mouse had a necrotic tumor in the left leg by visual inspection. The mouse was subjected to IR783 imaging and only the healthy C4-2 tumor on right leg could be imaged. Histopathology confirmed the necrotic status of the tumors. The lack of uptake of the dye in normal organs was confirmed by fluorescence imaging of all organs surgically removed from hosts following the imaging (data not shown). With the current instrumental setting, tumors as small as ~2 mm³ can be detected in mice, either as orthotopic or bone metastatic lesions (data not shown).

Figure 16:
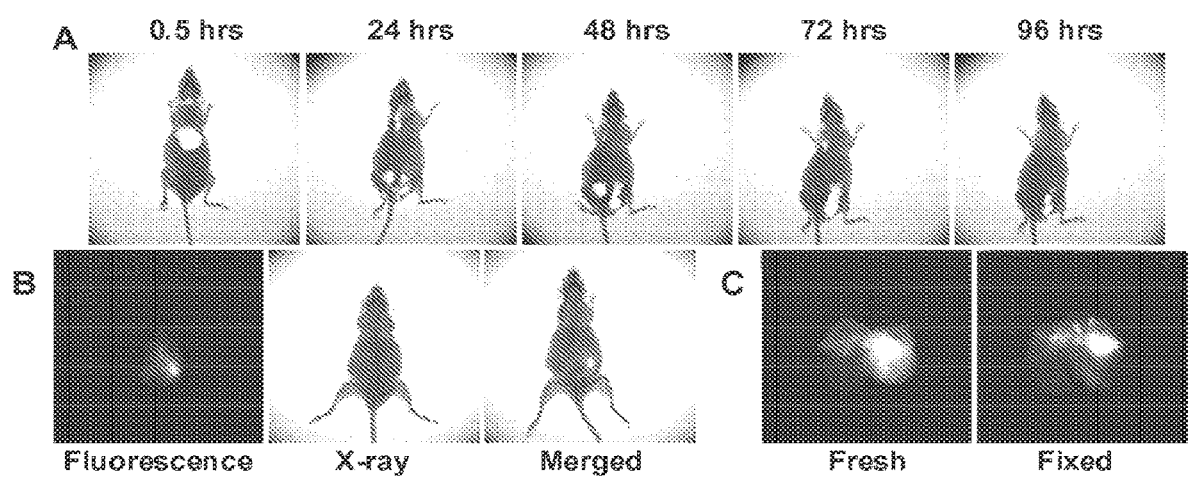
FIG. 16 shows NIR imaging of orthotopic xenograft ARCaP$_m$ tumor with IR783 and spontaneous prostate tumors of the TRAMP mouse using MHI148. Note the IR783 dye accumulated in tumor and metastases at 24-96 hours. The MHI148 dye was found stable in formalin fixation for weeks.

NIR imaging studies were performed to assess pharmacokinetics of the IR783 in vivo. Upon i.v or i.p administration, IR783 (0.2 μg/kg) initially accumulated in liver, lung and spleen then appeared in tumor at 24 hrs (FIG. 16). FIG. 16 shows the time-dependent uptake and accumulation of this dye in an orthotopic prostate ARCaP$_M$ tumor grown in a nude mouse (A) and in a spontaneous model of TRAMP mouse (B). This dye was shown to image locally invasive TRAMP tumors even after formalin fixation (C); mice without tumors yield background activity (data not shown). FIG. 16A shows a mouse bearing a 3.4 cm³ orthotopic tumor of the ARCaP$_M$ cells. This mouse was injected i.p with 0.2 μg/kg IR783 at 0 hrs. Successive imaging was performed to demonstrate preferential accumulation and prolonged retention of IR783 in tumor tissues; in these studies, non-specific imaging can be seen in the first 24 hrs, predominantly in the liver. IR783 was shown to accumulate in tumors and retained therein for more than 4 days. FIG. 16B shows spontaneous prostate tumor in a TRAMP mouse could be imaged 24 hours after IR783 administration. FIG. 16C shows the tumor detected in B dissected freshly and subjected to ex vivo imaging before (Fresh) and after fixation in formalin for 3 days (Fixed). The dye retention in formalin fixed tissues can be as long as several weeks (data not shown).

In these studies, IR783 accumulation was not detected in gall bladder or urinary bladder, suggesting other route of dye metabolism and clearance. NIR signals were found to be associated with tumors for at least 5 to 14 days after dye administration (FIG. 16). Stability of IR783 accumulation in tumors was further demonstrated in that this dye can tolerate fixation with both paraformaldehyde and glutaraldehyde (FIG. 16).

Figure 20:
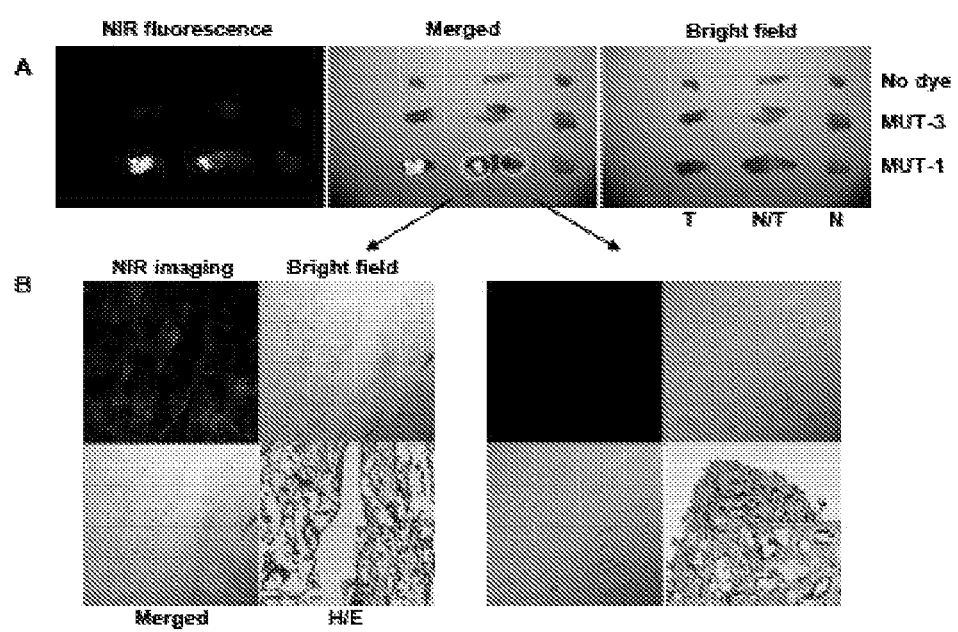
FIG. 20 shows NIR imaging of fresh human renal tumors.

The compounds of the invention can also be used to detect cancer in fresh (or frozen or preserved) cells. In one embodiment of this aspect of the invention, cells are obtained from small needle biopsy, needle aspiration, or other methods as known in the art. The cells after dye uptake is completed can be minced, sliced, smeared onto a slide, or any other preparation. An amount of one or more compound of the invention can be dropped onto the cells or otherwise contacted with the cells (shaken in a tube, for example). The cancer cells take up the dye and the normal cells do not. The cells can be imaged under a fluorescence microscope equipped with a NIR filter, for example. As an example, human renal tissues freshly obtained from surgery were incubated with IR783, washed, and imaged Confocal microscopic evidence demonstrated that IR783 was concentrated in renal cancer but not normal kidney cells. The results show that IR783 could be used to detect tumor cells in freshly obtained clinical specimens with cancer cells identified under a fluorescence microscope equipped with a NIR filter. FIG. 20(A) shows one fresh human renal tumor specimen dissected into three sections based on histopathological diagnosis: tumor section (T), transitional section containing both tumor and normal tissues (N/T), and normal region without tumor cells (N). Each section was then split into three pieces to be stained with IR783 (MUT-1), an inactive dye (MUT-3) and the remaining piece served as control, subjected to the staining process without addition of dyes (No dye). Fluorescence imaging revealed intense uptake and retention of IR783 by the tumor regions. FIG. 20B shows the fluorescence imaging of the sections after preparation into frozen section. This shows selective staining of cancer cells but not normal cells confirmed with confocal and H/E staining.

Figure 17:
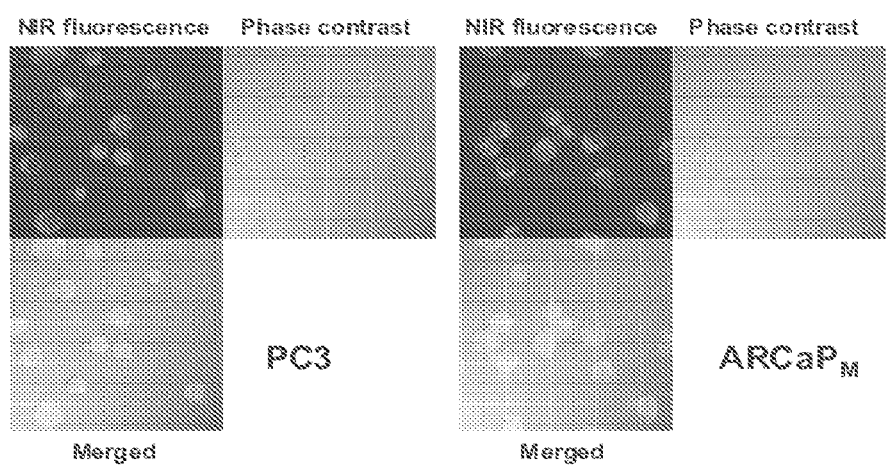
FIG. 17 shows NIR imaging to detect cancer cells in human blood using IR783.

IR783 can be used to detect and enrich disseminating cancer cells in the blood (FIG. 17). Specific detection of circulating tumor cells (CTC) in the blood is possible because prostate cancer cells have the ability to uptake and retain IR783, whereas normal mononuclear cells in periphery blood do not. 5×10³ human prostate cancer cells PC3 and ARCaP$_M$ were used to spike a 0.5 ml heparinized whole blood from a healthy donor. After incubation at 37° C. for 30 minutes, a gradient centrifugation (Histopaque-1077, Sigma) was applied to remove red blood cells. The remaining cells were washed 5 times in PBS, cells in 50 μl of the 250 μl total volume were smeared on a glass slide for NIR fluorescence detection. Cancer cells are large and yield strong fluorescence signals in the cytoplasm, but normal periphery mononucleated cells showed very low to background NIR fluorescence. This method can detect as few as 10 human prostate cancer cells/ml of human blood, a concentration close to that of the estimated numbers of CTC as reported by previous investigators.

Figure 18:
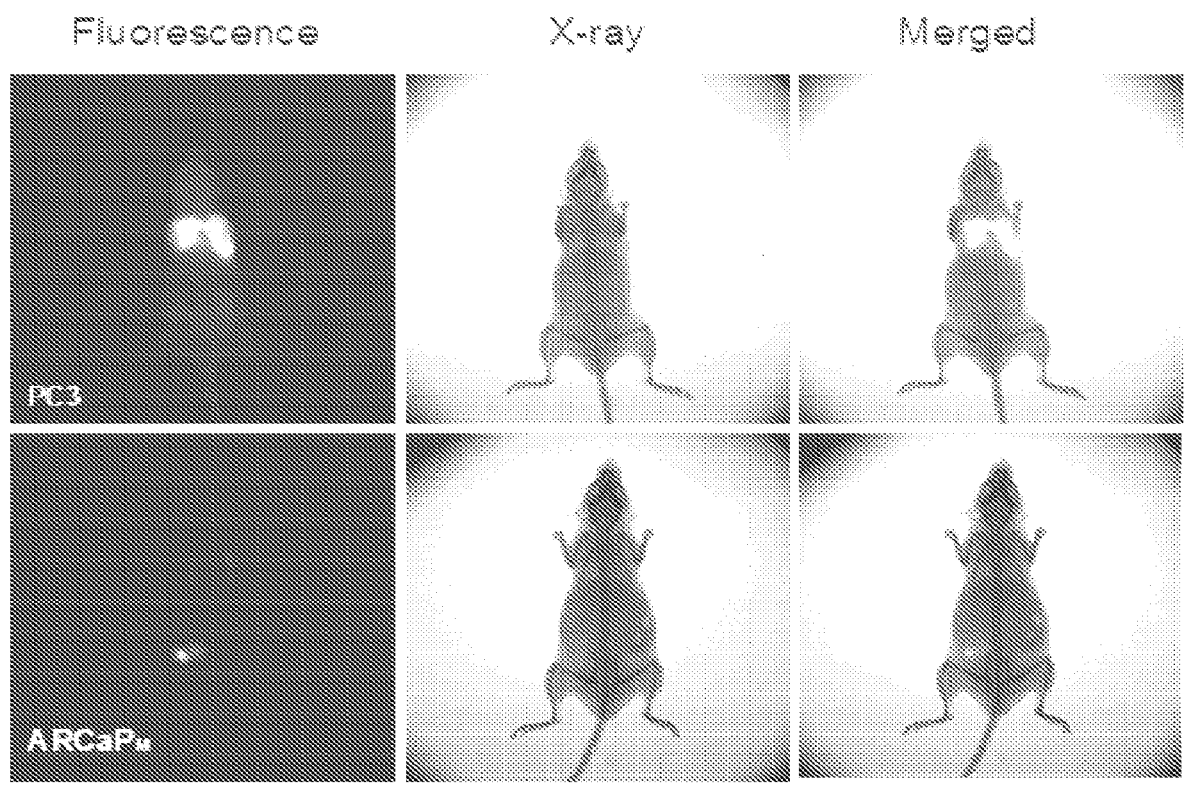
FIG. 18 shows tumor imaging in preestablished human prostate tumors, PC03 and ARCaP$_M$ using IR783.

FIG. 18 shows tumor imaging using IR783 in preestablished tumors. Subcutaneous ARCaP$_M$ and PC3 (four tumors with different sizes) tumors were established in live mice prior to the administration of IR-783. 5 nmol of IR783 were given to mice through tail vein and imaged using Kodak multimodal-imaging system. As shown, clear tumor images can be detected in both subcutaneous ARCaP$_M$ and PC3 tumors following intravenous administration of IR-783.

Figure 19:
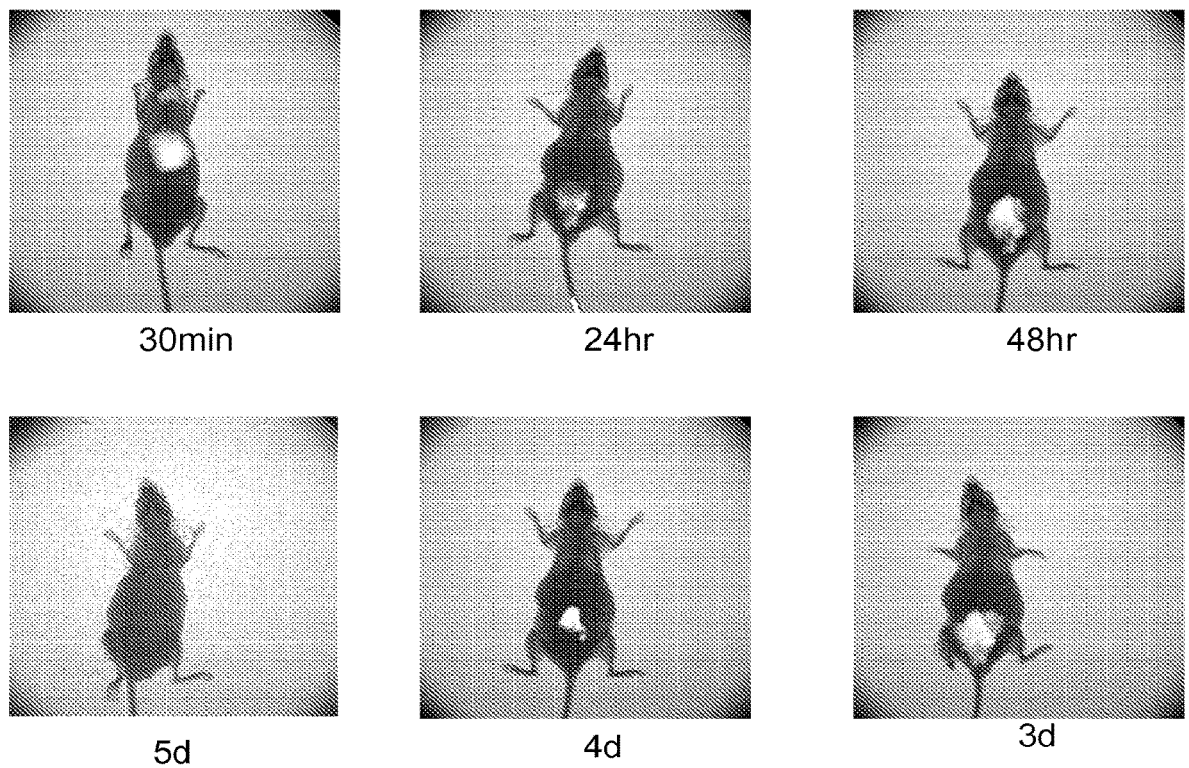
FIG. 19 shows the time-course of IR783 uptake by ARCaP orthotopic tumors.

FIG. 19 shows the time-course of IR783 uptake by ARCaP orthotopic tumors. Note 24-48 hrs after dye uptake, tumors and metastases can be readily identified.

Toxicity of IR783 and IR780 were compared as shown in the following table which records the weight of the mice. Mice were injected with 20 μg/Kg of IR783 and IR780 (which was 100× of the imaging dose which was 0.2 μg/Kg)

and results were compared for a 28 day period. Note IR783 was not toxic (mice gained weight like the controls which had PBS injected) during this observation period. Zero grams means the mouse died. ICG is a FDA approved dye used for several diagnostic purposes. ICG is considered to be nontoxic. ICG is used here as a measure of the toxicity of the tested compounds. If the mice treated with the tested compounds gain a similar amount of weight as mice treated with ICG, the toxicity of the tested compounds should be similar to ICG.

Toxicity test of dye based on body weight gained during the treatment period from 0 to 14 days.

|  | PBS | IR783 | | | IR780 | | | ICG |
| --- | --- | --- | --- | --- | --- | --- | --- | --- |
|  | 1X | 1X | 10X | 100X | 1X | 10X | 100X | 1X |
| 0 day | 20.57 g | 20.29 g | 20.57 g | 19.85 g | 19.00 g | 20.71 g | 20.14 g | 20.43 g |
| 1 day | 20.59 g | 20.20 g | 20.61 g | 19.74 g | 19.02 g | 20.69 g | 0 | 20.49 g |
| 2 day | 21.00 g | 20.23 g | 20.59 g | 20.01 g | 19.71 g | 20.70 g | 0 | 20.51 g |
| 3 day | 21.12 g | 20.32 g | 20.98 g | 20.39 g | 20.01 g | 21.03 g | 0 | 21.01 g |
| 4 day | 21.13 g | 20.34 g | 21.02 g | 20.43 g | 20.32 g | 21.24 g | 0 | 21.43 g |
| 5 day | 21.43 g | 21.00 g | 21.34 g | 21.01 g | 20.56 g | 21.89 g | 0 | 22.00 g |
| 6 day | 22.00 g | 21.87 g | 21.76 g | 21.23 g | 20.97 g | 22.00 g | 0 | 22.34 g |
| 7 day | 22.45 g | 22.32 g | 22.54 g | 22.00 g | 21.81 g | 22.56 g | 0 | 22.96 g |
| 14 day | 23.98 g | 23.91 g | 24.01 g | 23.76 g | 23.56 g | 24.00 g | 0 | 23.87 g |
| 28 day | 25.05 g | 24.86 g | 24.87 g | 24.61 g | 24.44 g | 24.56 g | 0 | 25.00 g |

REFERENCES

1). Ficken, G. E.; Kendall, J. D. The reactivity of the alkylthio group in nitrogen ring compounds. III. 2-Methylthiobenz[cd]indole and its methiodide. *J. Chem. Soc.*, 1960, 1537-41.
2). Lakshmikantham, M. V.; Chen, Wha; Cava, Michael P. Thioanhydrides. 3. Synthesis, properties, and Diels-Alder reactions of sulfur analogues of 1,8-naphthalic anhydride *J. Org. Chem.;* 1989, 54; 20 4746-4750
3). Deligeorgiev, T. G., Gadjev, N. I. Styryl dyes containing the benz[c,d]indolium heterocycle. *Dyes and Pigments,* 1991, 15, 215-23.
4). Vasilenko, N. P.; Mikhailenko, F. A.; Rozhinskii, Yu. I. 2-Methylbenz[c,d]indole and its derivatives. *Dyes and Pigments,* 1981, 2(3), 231-7.
5). Makin, S. M.; Boiko, I. I.; Shavrygina, O. A. Study of the aminoformylation of unsaturated aldehydes, 2-alkoxy aldehydes, and their alicyclic acetals and ketones. *Zh. Org. Khim.* 1977, 13(6), 1189-92.
WO96/17628; WO97/13490; WO03/082988; WO2008/025000; WO2007/134236; U.S. Pat. Nos. 6,217,848; 7,011,817; WO07/136996; US2005/0249668; WO03/074091; 7201892; 6180085; 6180086; Pham, Bioconjugate Chem 2005, 16, 735-740; GB 2020975; 5861424; Patent Abstracts of Japan 03090025; EP0286252; Japan Kokai SHO 55[1980]-100318; US2006/0099712; U.S. Pat. Nos. 5,360,803; 5,491,151; Near-infrared cyanine dye, Topics in Heterocyclic chemistry, Editor: Strekowski (2008).

DEFINITIONS

It is to be understood that this invention is not limited to the particular compounds, synthetic techniques, concentrations and other specificities provided as such may vary. It is also to be understood that the terminology used herein is for describing particular embodiments only, and is not intended to be limiting.

It is noted that, as used in this specification, the singular forms "a," "an," and "the" include plural referents unless the context clearly dictates otherwise. Thus, for example, reference to an "excipient" includes a single excipient as well as two or more of the same or different excipients, reference to a "compound" includes a single compound as well as two or more compounds, and the like.

"Alkyl" refers to a hydrocarbon chain, typically ranging from about 1 to 20 atoms in length. Such hydrocarbon chains are preferably but not necessarily saturated and may be branched or straight chain. Exemplary alkyl groups include ethyl, propyl, butyl, pentyl, 2-methylbutyl, 2-methylpropyl (isobutyl), 3-methylpentyl, and the like. As used herein, "alkyl" includes cycloalkyl when three or more carbon atoms are included. In one embodiment, alkyl has from 1-3 carbon atoms. In one embodiment, alkyl has from 1-6 carbon atoms.

"Alkoxy" refers to an —OR group, wherein R is alkyl or substituted alkyl, preferably CI-C20 alkyl (e.g., methoxy, ethoxy, propyloxy, benzyloxy, etc.). In one embodiment, alkoxy has from 1-7 carbon atoms.

"Non-interfering substituents" are those groups that, when present in a molecule, are typically non-reactive with other functional groups contained within the molecule. The term "substituted" as in, for example, "substituted alkyl," refers to a moiety (e.g., an alkyl group) substituted with one or more non-interfering substituents, such as, but not limited to: C3-C8 cycloalkyl, e.g., cyclopropyl, cyclobutyl, and the like; halo, e.g., fluoro, chloro, bromo, and iodo; cyano; alkoxy; phenyl; substituted phenyl; and the like.

"Aryl" means one or more aromatic rings, each having 5 or 6 core carbon atoms. Aryl includes multiple rings that may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as a substituent. For substitutions on a phenyl ring, the substituents may be in any orientation (i.e., ortho, meta, or para).

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen. Multiple rings may be fused, as in quinoline or benzofuran. In an embodiment, heterocycle groups are 5-10 membered rings with 1-3 heteroatoms selected from O, S, and N. "Substituted heterocycle" is a heterocycle having one or more side chains formed from non-interfering substituents. "Heteroaryl" is an aryl group containing from one to four N, O, or S atoms(s) or a combination thereof, which heteroaryl group is optionally substituted at carbon or nitrogen atom(s) with C1-6 alkyl, —CF3, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. In an embodiment, heteroaryl groups are 5-10-membered rings with 1-3 heteroatoms selected from O, S, and N.

"Substituted heteroaryl" is a heteroaryl having one or more non-interfering groups as substituents.

Each of the terms "drug," "biologically active molecule," "biologically active moiety," "active agent" and "biologically active agent", when used herein, means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, non-organic molecules such as metallic compounds, peptides, proteins, toxins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, antiviral agents, anti-inflammatory agents, anti-tumor agents, cardiovascular agents, anti-anxiety agents, hormones, growth factors, steroidal agents, and the like.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a compound or composition in a pharmaceutical preparation that is needed to provide a desired level of active agent and/or conjugate in the bloodstream or in the target tissue. The precise amount will depend upon numerous factors, e.g., the particular active agent, the components and physical characteristics of the pharmaceutical preparation, intended patient population, patient considerations, and the like, and can readily be determined by one skilled in the art, based upon the information provided herein and available in the relevant literature.

A "prodrug" includes any compound which, when administered to a patient, is converted in whole or in part to an active compound.

An "active metabolite" is a physiologically active compound which results from the metabolism of a compound of the invention, or a prodrug thereof, when such compound or prodrug is administered to a mammal.

"Polypeptide" or "poly(amino acid)" refers to any molecule comprising a series of amino acid residues, typically at least about 5-20 residues, linked through amide linkages (also referred to as peptide linkages) along the alpha carbon backbone. While in some cases the terms may be used synonymously herein, a polypeptide is a peptide typically having a molecular weight up to about 10,000 Da, while peptides having a molecular weight above that are commonly referred to as proteins. Modifications of the peptide side chains may be present, along with glycosylations, hydroxylations, and the like. Additionally, other non-peptidic molecules, including lipids and small drug molecules, may be attached to the polypeptide. The polypeptide may comprise any combination or sequence of amino acid residues.

"Amino acid" refers to organic acids containing both a basic mine group and an acidic carboxyl group. The term encompasses essential and non-essential amino acids and both naturally occurring and synthetic or modified amino acids. The most common amino acids are listed herein by either their name or by the three letter or single letter abbreviations: Glycine (Gly, G), Alanine (Ala, A), Valine (Val, V), Leucine (Leu, L), Isoleucine (Ile, I), Methionine (Met, M), Proline (Pro, P), Phenylalanine (Phe, F), Tryptophan (Trp, W), Serine (Ser, S), Threonine (Thr, T), Asparagine (Asn, N), Glutamine (Gln, Q), Tyrosine, (Tyr, Y), Cysteine (Cys, C), Lysine (Lys, K), Arginine (Arg, R), Histidine (His, H), Aspartic Acid (Asp, D), and Glutarnic acid (Glu, E).

By "residue" is meant the portion of a molecule remaining after reaction with one or more molecules. For example, an amino acid residue in a polypeptide chain is the portion of an amino acid remaining after forming peptide linkages with adjacent amino acid residues.

"Electron withdrawing group" or EWG refers to functional groups that remove electron density from the ring by making it less nucleophilic. In an embodiment, this class can be recognized by the atom adjacent to a 7 system having several bonds to more electronegative atoms or the presence of a formal charge. Examples of these groups include halogens, aldehydes, ketones, esters, carboxylic acids, acid chlorides, nitriles, nitrosos, and sulfonic acids.

"Electron donating group" or EDG refers to functional groups that add electron density to the ring by making it more nucleophilic. In an embodiment, this class can be recognized by lone pairs on the atom adjacent to the 7 system. Examples of these groups include alkyl, alkenyl, alkynyl, amides, ethers, alkoxides, alcohols, and amines.

The term "patient," refers to a living organism suffering from or prone to a condition that can be prevented or treated by administration of a compound or composition described herein, and includes both humans and animals. Patients which can be treated using the methods described herein include animals, vertebrates, mammals, human, cat, dog, cow, horse, sheep, pig, monkey, ape, other mammals, and avian (chicken, turkey, duck, goose, quail, pheasant, etc.).

"Optional" or "optionally" means that the subsequently described circumstance may or may not occur, so that the description includes instances where the circumstance occurs and instances where it does not.

Examples of pharmaceutically acceptable salts of the compounds and compositions according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfiuie, phosphoric, citric, tartaric, lactic, pyruvic, acetic, succinic, fumaric, maleic, oxaloacetic, methanesulfonic, ethanesulfonic, toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-I, 4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-l-sulfonates, naphthalene-2-sulfonates, and mandelates.

An acid addition salt may be reconverted to the free base by treatment with a suitable base. Preparation of basic salts of acid moieties which may be present on a compound of the present invention may be prepared in a similar manner using a pharmaceutically acceptable inorganic or organic base, such as an amine (primary, secondary or tertiary), an alkali metal or alkaline earth metal hydroxide or the like.

Illustrative examples of suitable salts include organic salts derived from amino acids such as glycine and arginine, ammonia, primary, secondary and tertiary mines, and cyclic amines such as piperidine, morpholine and piperazine, and inorganic salts derived from sodium, calcium, potassium, magnesium, manganese, iron, copper, zinc, aluminum and lithium. Exemplary bases include sodium hydroxide, potassium hydroxide, ammonium hydroxide, calcium hydroxide, triethylamine, or the like.

Esters of the compounds of the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable mine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl) chloride, benzoyl chloride, methyl isocyanate, ethyl chloroformate, methanesulfonyl chloride) and a suitable base (e.g., 4-dimethylarninopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C.

Examples of pharmaceutically acceptable solvents include, but are not limited to, compounds according to the invention in combination with water, isopropanol, ethanol, methanol, DMSO, ethyl acetate, acetic acid, or ethanolamine.

In the case of solid formulations, it is understood that the compounds of the invention may exist in different forms, such as stable and metastable crystalline forms and isotropic and amorphous forms, all of which are intended to be within the scope of the present invention. The present invention also includes stereoisomers of the compounds described herein, where applicable, either individually or admixed in any proportions.

Stereoisomers may include, but are not limited to, enantiomers, diastereomers, racemic mixtures and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in a mixture with other isomers of the compounds described herein.

The present invention also provides pharmaceutical formulations or compositions, both for veterinary and for human medical use, which comprise the compounds of the invention (or ester, amide, salt, solvate, metabolite, or derivative thereof) with one or more pharmaceutically acceptable carriers thereof, and optionally any other therapeutic ingredients, such as other chemotherapeutic agents. The carrier(s) must be pharmaceutically acceptable in the sense of being compatible with the other ingredients of the formulation and not unduly deleterious to the recipient thereof. Such carriers are known in the art. See, Wang et al. (1980) *J Parent. Drug Assn.* 34(6):452-462, herein incorporated by reference in its entirety. Formulations of the present invention may include short-term, rapid-onset, rapid-offset, controlled release, sustained release, delayed release, and pulsatile release formulations, providing the formulations achieve administration of a compound as described herein. See *Remington's Pharmaceutical Sciences* (1 8" ed.; Mack Publishing Company, Eaton, Pa., 1990), herein incorporated by reference in its entirety.

Pharmaceutical formulations according to the present invention are suitable for various modes of delivery, including oral, parenteral (including intravenous, intramuscular, subcutaneous, intrademal, and transdermal), topical (including dermal, buccal, and sublingual), and rectal administration. The most useful and/or beneficial mode of administration can vary, especially depending upon the condition of the recipient and the disorder being treated.

The pharmaceutical formulations may be conveniently made available in a unit dosage form, whereby such formulations may be prepared by any of the methods generally known in the pharmaceutical arts. Generally speaking, such methods of preparation comprise combining (by various methods) an active agent, such as the compounds according to the present invention (or a pharmaceutically acceptable ester, amide, salt, or solvate thereof) with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

Adjuvants or accessory ingredients for use in the formulations of the present invention can include any pharmaceutical ingredient commonly deemed acceptable in the art, such as binders, fillers, lubricants, disintegrants, diluents, surfactants, stabilizers, preservatives, flavoring and coloring agents, and the like. Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluloses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the formulation according to the present invention may be anionic, cationic, amphoteric, or nonionic surface active agents. Stabilizers may be included in the formulations to inhibit or lessen reactions leading to decomposition of the active agent, such as oxidative reactions.

Pharmaceutical formulations according to the present invention suitable as oral dosage may take various forms, such as tablets, capsules, caplets, and wafers (including rapidly dissolving or effervescing), each containing a predetermined amount of the active agent. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of the above dosage forms are generally known in the art, and any such method would be suitable for the preparation of the respective dosage forms for use in delivery of the compounds according to the present invention.

A tablet containing a compound according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agent.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Solid dosage forms may be formulated so as to provide a delayed release of the active agent, such as by application of a coating. Delayed release coatings are known in the art, and dosage forms containing such may be prepared by any known suitable method. Such methods generally include that, after preparation of the solid dosage form (e.g. a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agent over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents.

Such formulations for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described. The compounds according to the present invention may also be administered transdermally, wherein the active agent is incorporated into a laminated structure (generally referred to as a "patch") that is adapted to remain in intimate contact with the epidermis of the recipient for a prolonged period of time. Typically, such patches are available as single layer "drug-in-adhesive" patches or as multilayer patches where the active agent is contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis. Formulations for rectal delivery of the compounds of the present invention include rectal suppositories, creams, ointments, and liquids. Suppositories may be presented as the active agent in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

Topical formulations may be in any form suitable and readily known in the art for delivery of an active agent to the body surface, including dermally, buccally, and sublingually. Typical examples of topical formulations include ointments, creams, gels, pastes, and solutions. Formulations for topical administration in the mouth also include lozenges.

Nasal spray formulations comprise purified aqueous solutions of the active agent with preservative agents and isotonic agents. Such formulations are preferably adjusted to a pH and isotonic state compatible with the nasal mucous membranes.

Ophthalmic formulations are prepared by a similar method to the nasal spray, except that the pH and isotonic factors are preferably adjusted to match that of the eye. Further, the present invention provides liposomal formulations of the compounds of the invention and salts thereof. The technology for forming liposomal suspensions is well known in the art. When the compound of the invention is an aqueous-soluble salt, using conventional liposome technology, the same may be incorporated into lipid vesicles. In such an instance, due to the water solubility of the compound, the compound will be substantially entrained within the hydrophilic center or core of the liposomes. The lipid layer employed may be of any conventional composition and may either contain cholesterol or may be cholesterol-free. When the compound of interest is water-insoluble, again employing conventional liposome formation technology, the compound may be substantially entrained within the hydrophobic lipid bilayer that forms the structure of the liposome. In either instance, the liposomes that are produced may be reduced in size, as through the use of standard sonication and homogenization techniques.

The liposomal formulations containing the compounds of the invention may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of the invention or a plurality of solid particles of the compound. The desired formulation may be placed in a small chamber and nebulized. Nebulization may be accomplished by compressed air or by ultrasonic energy to form a plurality of liquid droplets or solid particles comprising the compounds or salts.

By "treatment or prevention" is intended the alleviation of the signs, symptoms, or causes of a disease, or any other desired alteration of a biological system. Accordingly, the method of the invention "prevents" (i.e., delays or inhibits) and/or "reduces" (i.e., decrease, slows, or ameliorates) the detrimental effects of the cancer, or neoplastic disease or disorder, in the mammal receiving the therapy. As used herein, a "neoplastic disease or disorder" is characterized by one or more of the following properties: cell growth that is not regulated by the normal biochemical and physical influences in the environment; anaplasia (i.e., lack of normal coordinated cell differentiation); and in some instances, metastasis. Further, as used herein, the term "cancer" is understood to mean a disease characterized by abnormal growth of cells that is not regulated by the normal biochemical and physical influences in the environment. Accordingly, as used herein, the terms cancer and neoplasia are intended to be interchangeable.

Neoplastic diseases capable of treatment according to the invention include, for example, anal carcinoma, bladder carcinoma, breast carcinoma, cervix carcinoma, chronic lymphocytic leukemia, chronic myelogenous leukemia, endometrial carcinoma, hairy cell leukemia, head and neck carcinoma, lung (small cell) carcinoma, multiple myeloma, non-Hodgkin's lymphoma, follicular lymphoma, ovarian carcinoma, brain tumors, colorectal carcinoma, hepatocellular carcinoma, Kaposi's sarcoma, lung (non-small cell carcinoma), melanoma, pancreatic carcinoma, prostate carcinoma, renal cell carcinoma, ductal carcinoma, gastric carcinoma, squamous cell carcinoma, basal cell carcinoma, and soft tissue sarcoma. Additional neoplastic disorders can be found in, for example, Isselbacher et al. (1994) Harrison Principles of Internal Medicine 1814-1877, which is herein incorporated by reference.

As used herein, "therapeutic effect" means reducing the signs, symptoms, or causes of a disease, or other desired alteration of a biological system such as delay of disease progression by prevention or eliminating circulating cancer cells from the blood or facilitating the death of cancer cells in lymph node, bone marrow and/or soft tissues. Delivery of a therapeutically effective amount of a compound of the invention may be obtained via administration of a pharmaceutical composition comprising a therapeutically effective dose of this agent. By "therapeutically effective amount" or "dose" or "cytotoxic amount" is meant a concentration of a conjugate of the invention that is sufficient to elicit the desired therapeutic effect according to the various methods of treatment described herein. Accordingly, in one embodiment, a therapeutically effective amount is an amount effective to treat cancer, such as inhibiting or slowing growth of cancerous tissue. According to another embodiment, a therapeutically effective amount is an amount effective to treat an inflammatory disease. Preferably, for purposes of cancer therapy, a compound of any of the above formulas is administered to the subject in an amount sufficient to inhibit production of TF or VEGF, thereby inhibiting angiogenesis. However, the therapeutically effective dosage of any specific compound will vary somewhat from compound to compound, patient to patient, and will depend upon the condition of the patient and the route of delivery. The effective amount of any particular compound would be expected to vary according to the weight, sex, age, and medical history of the subject. Other factors which influence the effective amount may include, but are not limited to, the severity of the patient's condition, the disease or disorder being treated, the stability of the compound according to the invention, and, if appropriate, any additional antineoplastic therapeutic agent being administered with the compound of the invention. Methods to determine efficacy and dosage are known to those skilled in the art. See, for example, Isselbacher et al. (1996) Harrison Principles of Internal Medicine 13 ed., 1814-1882, herein incorporated by reference. As a general proposition, a dosage from about 0.5 to about 20 mg/kg body weight, preferably from about 1.0 to about 5.0 mg/kg, will have therapeutic efficacy. When administered conjointly with other pharmaceutically active agents, even less of the compounds of the invention may be therapeutically effective. The compounds of the invention may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

As used herein, "cancer" means a disease characterized by abnormal growth of cells that is not regulated by the normal biochemical, physiological and physical influences from the host micro environment. Cancer which is capable of responding to treatment according to the compounds, compositions and methods disclosed herein include, for example, those listed in Isselbacher et al. (1994), Harrison Principles of Internal Medicine, 1814-1877. The compounds, compositions and methods disclosed herein are useful in the treatment of cancers such as, carcinomas, lymphomas, leukemias, neuroendocrine tumors, and sarcomas. A representative but non-limiting list of cancers is lymphoma, Hodgkin's Disease, myeloid leukemia, bladder cancer, brain cancer, head and neck cancer, kidney cancer, lung cancers such as small cell lung cancer and non-small cell lung cancer, myeloma, neuroblastoma/glioblastoma, ovarian cancer, thyroid and adrenal gland cancers, pancreatic cancer, prostate cancer, skin cancer, liver cancer, melanoma, colon cancer, cervical cancer, breast cancer, and other epithelial and mesenchymal cancers with unknown origin. The compounds, compositions and methods disclosed herein may be used for the treatment of cancers through direct cytotoxic effects on localized and disseminated cancers but also can exert cytotoxicity to circulating cancer cells thus preventing the disseminated cancer cells from reaching metastatic sites. "Cancer" and "tumor" are used interchangeably herein.

Methods to determine if the neoplastic disorder has been treated are well known to those skilled in the art and include, for example, a decrease in the number of neoplastic cells (i.e., a decrease in cell proliferation or a decrease in tumor size). It is recognized that the treatment of the present invention may be a lasting and complete response or can encompass a partial or transient clinical response. See for example, Isselbacher et al. (1996) Harrison's Principles of Internal Medicine 13 ed., 18 14-1 882, herein incorporated by reference.

Assays to test for the death of neoplastic cells are well known in the art, including, for example, standard dose response assays that assess cell viability; agarose gel electrophoresis of DNA extractions or flow cytometry to determine DNA fragmentation, a characteristic of cell death; assays that measure the activity of polypeptides involved in apoptosis; and assay for morphological signs of cell death. The details regarding such assays are described elsewhere. Other assays include, chromatin assays (i.e., counting the frequency of condensed nuclear chromatin) or drug resistance assays as described in, for example, Lowe et al. (1993) Cell 74:957-697, herein incorporated by reference. See also U.S. Pat. No. 5,821,072, also herein incorporated by reference.

In addition, assays to test for the effectiveness of the compounds of the invention can be preliminarily evaluated by using a tumor growth regression assay which assesses the ability of tested compounds to inhibit the growth of established solid tumors in mice. The assay can be performed by implanting tumor cells into the subcutaneous, orthotopic and intraosseous sites or the fat pads of nude mice.

Tumor cells are then allowed to grow to a certain size before the agents are administered. The volumes of tumors are monitored for a set number of weeks, e.g., three weeks. General health of the tested animals is also monitored during the course of the assay. The compounds of the invention can be used in combination with other antineoplastic therapeutic agents. When a compound of the invention is administered in combination with an antineoplastic therapeutic agent (i.e., co-administration), it is recognized that a compound of the invention and the antineoplastic therapeutic agent can be administered in a fixed combination (i.e., a single pharmaceutical formulation that contains both active materials). Alternatively, a compound of the invention may be administered simultaneously with the antineoplastic therapeutic agent. In another embodiment, the compound of the invention and the antineoplastic therapeutic agent are administered sequentially (i.e., administration of the compound of the invention begins shortly after the end of the antineoplastic therapeutic agent regime or, alternatively, administration of the inventive compound precedes the administration of the antineoplastic therapeutic agent). One of skill in the art will recognized that the most preferred method of administration will allow the desired therapeutic effect, ie., the enhanced cell death of a neoplastic cell.

Any additional antineoplastic agent (i.e., chemotherapeutic, radiation, or biological response modifiers) can be used in the methods of the present invention. It is understood that the antineoplastic agent may affect neoplastic cells by a variety of mechanisms, including killing or decreasing viability, by apoptosis, or by various other cellular mechanisms. In any particular embodiment of the invention, the antineoplastic therapeutic agent will be selected with reference to factors such as the type of neoplastic disorder and the efficacy of the antineoplastic agent for treating the desired neoplastic disorder.

Chemotherapeutic agents include, but are not limited to, Aminoglutethimide; Asparaginase; Bleomycin; Busulfan; Carboplatin; Carmustine (BCNU); Chlorambucil; Cisplatin (cis-DDP); Cyclophosphamide; Cytarabine HCl; Dacarbazine; Dactinomycin; Daunorubicin HCl; Doxorubicin HCl; Estramustine phosphate sodium; Etoposide (VP-16); Floxuridine; Fluorouracil (5-FU); Flutamide; Hydroxyurea ('hydroxycarbamide); Ifosfamide; Interferon a-2a, a-2b, Lueprolide acetate (LHRH-releasing factor analogue); Lomustine (CCNU); Mechlorethamine HCl (nitrogen mustard); Melphatan; Mercaptopurine; Mesna; Methotrexate (MTX); Mitomycin; Mitotane (0.p'-DDD); Mitoxantrone HCl; Octreotide; Paclitaxel; Plicamycin; Procarbazine HCl; Streptozocin, Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bis-guanylhydrazone; MGBG); Pentostatin; Semustine (methyl-CCNU); Teniposide (VM-26); paclitaxel and other taxanes; and Vindesine sulfate.

Additional antineoplastic therapeutic agents which find use in the methods of the present invention include biological response modifiers. As used herein "biological response modifiers" comprise any agent that functions by altering the host response to cancer, rather than by direct cytotoxicity. Biological response modifiers include, for example, monoclonal antibodies and cytokines. See, for example, Isselbacher et al. (1994) Harrison's Principles of Internal Medicine, 1834-1841, which is herein incorporated by reference. Cytokines are a group of intercellular messenger proteins that are key immunoregulatory compounds. They comprise the largest group of biologic therapeutics in clinical trials and include interferons (i.e., Type 1 interferons such as INF-u and INF-P and Type I1 interferons such as INF-y), interleukins, and hematopoeitic growth factors (i.e., erythropoietin, granulocyte-macrophage colony stimulating factor (GM-CSF) and granulocyte colony stimulating factor (G-CSF)).

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, elements, starting materials, synthetic methods, and components other than those specifically exemplified can be employed in the practice of the invention without resort to undue experimentation. All art-known functional equivalents, of any such methods, elements, starting materials, synthetic methods, and components are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In general the terms and phrases used herein have their art-recognized meaning, which can be found by reference to standard texts, journal references and contexts known to those skilled in the art. The definitions are provided to clarify their specific use in the context of the invention.

One skilled in the art readily appreciates that the present invention is well adapted to carry out the objects and obtain the ends and advantages mentioned, as well as those inherent in the present invention. The methods, components, materials and concentrations described herein as currently representative of preferred embodiments are provided as examples and are not intended as limitations on the scope of the invention. Changes therein and other uses which are encompassed within the spirit of the invention will occur to those skilled in the art, are included within the scope of the claims.

Although the description herein contains certain specific information and examples, these should not be construed as limiting the scope of the invention, but as merely providing illustrations of some of the embodiments of the invention. Thus, additional embodiments are within the scope of the invention and within the claims.

The exact formulation, route of administration and dosage can be chosen by the individual physician in view of the patient's condition (see e.g. Fingl et. al., in The Pharmacological Basis of Therapeutics, 1975, Ch. 1 p. 1).

It should be noted that the attending physician would know how to and when to terminate, interrupt, or adjust administration due to toxicity, or to organ dysfunctions, or for other reasons. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995). Suitable routes may include, for example, oral, rectal, transdermal, vaginal, transmucosal, or intestinal administration; parenteral delivery, including intramuscular, subcutaneous, or intramedullary injections, as well as intrathecal, intravenous, or intraperitoneal injections.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

We claim:

1. A method of imaging cancer cells, wherein the method comprises introducing to the cancer cells an imaging amount of a compound of the formula shown below

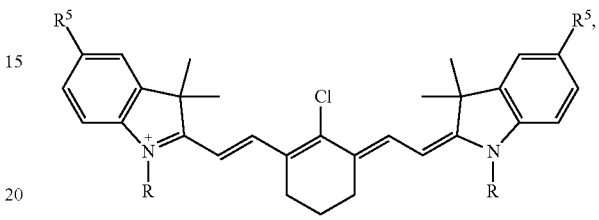

wherein each of $R^5$ is H; and
wherein the R substituents are the same, or are not the same; and
wherein the R substituents are independently selected from the group consisting of: $(CH_2)_3COOH$, or an ester or amide thereof, $(CH_2)_4COOH$, or an ester or amide thereof, $(CH_2)_5COOH$, or an ester or amide thereof, $(CH_2)_6COOH$, or an ester or amide thereof, $(CH_2)_7COOH$, or an ester or amide thereof, $(CH_2)_8COOH$, or an ester or amide thereof, $(CH_2)_9COOH$, or an ester or amide thereof, $(CH_2)_3SO_3H$, $(CH_2)_4SO_3H$, $(CH_2)_5SO_3H$, $(CH_2)_6SO_3H$, $(CH_2)_7SO_3H$, $(CH_2)_8SO_3H$, and $CH_2)_9SO_3H$;
exposing the cancer cells to electromagnetic radiation; and
detecting light emission from the compound; and
wherein the compound is introduced to one or more cancer cells without a targeting agent; and
wherein the amide of the R substituent is not tagged with a radioactive group; and
wherein if the compound is used in combination with a therapeutic agent or radioactive agent, the agent is co-administered with the compound simultaneously or sequentially, and is not linked to the compound.

2. The method of claim 1, wherein the R substituents are independently selected from the group consisting of: $(CH_2)_3COOH$, $(CH_2)_4COOH$, $(CH_2)_5COOH$, $(CH_2)_6COOH$, $(CH_2)_7COOH$, $(CH_2)_8COOH$, $(CH_2)_9COOH$, $(CH_2)_3SO_3H$, $(CH_2)_4SO_3H$, $(CH_2)_5SO_3H$, $(CH_2)_6SO_3H$, $(CH_2)_7SO_3H$, $(CH_2)_8SO_3H$, and $(CH_2)_9SO_3H$.

3. The method of claim 1, wherein the R substituents are independently selected from the group consisting of: $(CH_2)_5COOH$, or an ester or amide thereof, $(CH_2)_4COOH$, or an ester or amide thereof, $(CH_2)_3COOH$, or an ester or amide thereof, and $(CH_2)_4SO_3H$.

4. The method of claim 1, wherein the R substituents are independently selected from the group consisting of: $(CH_2)_5COOH$, $(CH_2)_4COOH$, $(CH_2)_3COOH$, and $(CH_2)_4SO_3H$.

5. The method of claim 1, wherein the R substituents are selected from two acid groups, one acid and one ester group, and two ester groups.

6. The method of claim 1, wherein the R substituents are independently selected from the group consisting of: $(CH_2)_5COOH$, and $(CH_2)_4SO_3H$.

7. A method of claim 1, wherein the method comprises introducing to the cancer cells an imaging amount of a compound selected from the group consisting of: MHI-148, MHI-25 (also known as IR783), MHI-160, and MHI-161, an ester of each thereof, or an amide of each thereof.

8. The method of claim 1, wherein the method comprises introducing to the cancer cells an imaging amount of MHI-25 (also known as IR783), or an ester or amide thereof.

9. The method of claim 1, wherein the cancer cells are imaged in vivo.

10. The method of claim 1, wherein the cancer cells comprise lymphoma, myeloid leukemia, bladder cancer, brain cancer, head and neck cancer, kidney cancer, lung cancer, myeloma, ovarian cancer, cervical cancer, bone cancer, thyroid cancer, adrenal gland cancer, cholangiocarcinoma, pancreatic cancer, prostate cancer, skin cancer, liver cancer, testicular cancer, colon cancer, or breast cancer cells.

11. A method of treating cancer, the method comprising administering to a patient in need thereof a therapeutically effective amount of a compound of the formula shown below

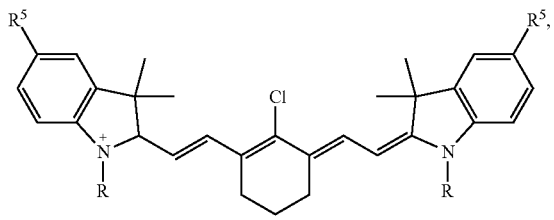

wherein each of $R^5$ is H; and wherein the R substituents are the same, or are not the same; and wherein the R substituents are independently selected from the group consisting of: $(CH_2)_3COOH$, or an ester or amide thereof, $(CH_2)_4COOH$, or an ester or amide thereof, $(CH_2)_5COOH$, or an ester or amide thereof, $(CH_2)_6COOH$, or an ester or amide thereof, $(CH_2)_7COOH$, or an ester or amide thereof, $(CH_2)_8COOH$, or an ester or amide thereof, $(CH_2)_9COOH$, or an ester or amide thereof, $(CH_2)_3SO_3H$, $(CH_2)_4SO_3H$, $(CH_2)_5SO_3H$, $(CH_2)_6SO_3H$, $(CH_2)_7SO_3H$, $(CH_2)_8SO_3H$, and $CH_2)_9SO_3H$; and wherein the compound is introduced to one or more cancer cells of the patient without a targeting agent; and wherein if the compound is used in combination with a therapeutic agent or radioactive agent, the agent is co-administered with the compound simultaneously or sequentially, and is not linked to the compound.

12. The method of claim 11, wherein the R substituents are independently selected from the group consisting of: $(CH_2)_3COOH$, $(CH_2)_4COOH$, $(CH_2)_5COOH$, $(CH_2)_6COOH$, $(CH_2)_7COOH$, $(CH_2)_8COOH$, $(CH_2)_9COOH$, $(CH_2)_3SO_3H$, $(CH_2)_4SO_3H$, $(CH_2)_5SO_3H$, $(CH_2)_6SO_3H$, $(CH_2)_7SO_3H$, $(CH_2)_8SO_3H$, and $CH_2)_9SO_3H$.

13. The method of claim 11, wherein the R substituents are independently selected from the group consisting of: $(CH_2)_5COOH$, or an ester or amide thereof, $(CH_2)_4COOH$, or an ester or amide thereof, $(CH_2)_3COOH$, or an ester or amide thereof, $(CH_2)_2COOH$, or an ester or amide thereof, and $(CH_2)_4SO_3H$.

14. The method of claim 11, wherein the R substituents are selected from wherein the R substituents are independently selected from the group consisting of: $(CH_2)_5COOH$, $(CH_2)_4COOH$, $(CH_2)_3COOH$, and $(CH_2)_4SO_3H$.

15. The method of claim 11, wherein the R substituents are selected from two acid groups, one acid and one ester group, and two ester groups.

16. The method of claim 11, wherein the R substituents are independently selected from the group consisting of: $(CH_2)_5COOH$, and $(CH_2)_4SO_3H$.

17. The method of claim 11, wherein the method comprises administering a therapeutically effective amount of a compound selected from the group consisting of: MHI-148, MHI-25 (also known as IR783), MHI-160, MHI-161, an ester of each thereof, or an amide of each thereof.

18. The method of claim 11, wherein the method comprises administering a therapeutically effective amount of MHI-25 (also known as IR783), or an ester or amide thereof.

19. The method of claim 11, wherein the cancer cells are tracked during or after therapy by monitoring the accumulation of the compound in one or more cells or tissues of the patient by imaging.

20. The method of claim 11, wherein the cancer cells comprise lymphoma, myeloid leukemia, bladder cancer, brain cancer, head and neck cancer, kidney cancer, lung cancer, myeloma, ovarian cancer, cervical cancer, bone cancer, thyroid cancer, adrenal gland cancer, cholangiocarcinoma, pancreatic cancer, prostate cancer, skin cancer, liver cancer, testicular cancer, colon cancer, or breast cancer cells.

21. The method of claim 1, wherein an additional antineoplastic agent is used in the method, and the additional antineoplastic agent comprises a chemotherapeutic, radiation or biological response modifier.

22. The method of claim 11, wherein an additional antineoplastic agent is used in the method, and the additional antineoplastic agent comprises a chemotherapeutic, radiation or biological response modifier.

* * * * *